(12) United States Patent
Wong et al.

(10) Patent No.: US 10,905,879 B2
(45) Date of Patent: *Feb. 2, 2021

(54) METHODS FOR PERIPHERAL NERVE STIMULATION

(71) Applicant: Cala Health, Inc., Burlingame, CA (US)

(72) Inventors: Serena HanYing Wong, Palo Alto, CA (US); Kathryn H. Rosenbluth, San Francisco, CA (US); Samuel Richard Hamner, San Francisco, CA (US); Paula Chidester, Menlo Park, CA (US); Scott L. Delp, Stanford, CA (US); Terence D. Sanger, Los Angeles, CA (US); David Klein, Palo Alto, CA (US)

(73) Assignee: Cala Health, Inc., Burlingame, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/780,758

(22) Filed: Feb. 3, 2020

(65) Prior Publication Data
US 2020/0254251 A1  Aug. 13, 2020

Related U.S. Application Data

(60) Continuation of application No. 16/242,983, filed on Jan. 8, 2019, now Pat. No. 10,549,093, which is a
(Continued)

(51) Int. Cl.
*A61N 1/36* (2006.01)
*A61N 1/04* (2006.01)
(Continued)

(52) U.S. Cl.
CPC ........ *A61N 1/36031* (2017.08); *A61B 5/1101* (2013.01); *A61B 5/6824* (2013.01);
(Continued)

(58) Field of Classification Search
CPC ............ A61N 1/36014; A61N 1/36067; A61N 1/0456
See application file for complete search history.

(56) References Cited

U.S. PATENT DOCUMENTS 3,204,637 A  9/1965  Frank et al.
3,870,051 A  3/1975  Brindley
(Continued)

FOREIGN PATENT DOCUMENTS

DE   102008042373   4/2010
DE   102009004011   7/2010
(Continued)

OTHER PUBLICATIONS

U.S. Appl. No. 16/071,056, filed Jul. 18, 2018, Wong et al.
(Continued)

*Primary Examiner* — Paula J Stice
(74) *Attorney, Agent, or Firm* — Knobbe, Martens, Olson & Bear LLP

(57) ABSTRACT

A peripheral nerve stimulator can be used to stimulate a peripheral nerve to treat essential tremor, Parkinsonian tremor, and other forms of tremor. The stimulator can have electrodes that are placed circumferentially around the patient's wrist or arm. Specific nerves in the wrist or arm can be targeted by appropriate spacing of the electrodes. Positioning the electrodes on generally opposing sides of the target nerve can result in improved stimulation of the nerve. The stimulation pattern may alternate between the nerves.
(Continued)

Improved stimulation algorithms can incorporate tremor feedback, external data, predictive adaptation, and long-term monitoring data.

19 Claims, 31 Drawing Sheets

Related U.S. Application Data continuation of application No. 15/721,480, filed on Sep. 29, 2017, now Pat. No. 10,173,060, which is a division of application No. 15/354,943, filed on Nov. 17, 2016, now Pat. No. 9,802,041, which is a continuation of application No. PCT/US2015/033809, filed on Jun. 2, 2015.

(60) Provisional application No. 62/157,116, filed on May 5, 2015, provisional application No. 62/083,424, filed on Nov. 24, 2014, provisional application No. 62/006,555, filed on Jun. 2, 2014, provisional application No. 62/006,565, filed on Jun. 2, 2014.

(51) Int. Cl.
*A61B 5/11* (2006.01)
*A61B 5/00* (2006.01)

(52) U.S. Cl.
CPC ......... *A61N 1/0456* (2013.01); *A61N 1/0476* (2013.01); *A61N 1/0484* (2013.01); *A61N 1/36* (2013.01); *A61N 1/36014* (2013.01); *A61N 1/36034* (2017.08); *A61N 1/0496* (2013.01); *A61N 1/36025* (2013.01)

(56) References Cited

U.S. PATENT DOCUMENTS

| | | | |
|---|---|---|---|
| 4,300,575 A | 11/1981 | Wilson |
| 4,458,696 A | 7/1984 | Larimore |
| 4,461,075 A | 7/1984 | Bailey |
| 4,539,996 A | 9/1985 | Engel |
| 4,569,351 A | 2/1986 | Tang |
| 4,582,049 A | 4/1986 | Ylvisaker |
| 4,729,377 A | 3/1988 | Granek et al. |
| 4,739,764 A | 4/1988 | Lue et al. |
| 4,763,659 A | 8/1988 | Dunseath, Jr. |
| 4,771,779 A | 9/1988 | Tanagho et al. |
| 4,981,146 A | 1/1991 | Bertolucci |
| 4,982,432 A | 1/1991 | Clark et al. |
| 5,003,978 A | 4/1991 | Dunseath, Jr. |
| 5,052,391 A | 10/1991 | Silverstone et al. |
| 5,070,862 A | 12/1991 | Berlant |
| 5,137,507 A | 8/1992 | Park |
| 5,330,516 A | 7/1994 | Nathan |
| 5,397,338 A | 3/1995 | Grey et al. |
| 5,514,175 A | 5/1996 | Kim et al. |
| 5,540,235 A | 7/1996 | Wilson |
| 5,562,707 A | 10/1996 | Prochazka et al. |
| 5,562,717 A | 10/1996 | Tippey et al. |
| 5,573,011 A | 11/1996 | Felsing |
| 5,575,294 A | 11/1996 | Perry et al. |
| 5,606,968 A | 3/1997 | Mang |
| 5,643,173 A | 7/1997 | Welles |
| 5,775,331 A | 7/1998 | Raymond et al. |
| 5,833,709 A | 11/1998 | Rise et al. |
| 5,833,716 A | 11/1998 | Bar-Or et al. |
| 5,899,922 A | 5/1999 | Loos |
| 6,016,449 A | 1/2000 | Fischell et al. |
| 6,081,744 A | 6/2000 | Loos |
| 6,161,044 A | 12/2000 | Silverstone |
| 6,178,352 B1 | 1/2001 | Gruzdowich et al. |
| 6,351,674 B2 | 2/2002 | Silverstone |
| 6,366,813 B1 | 4/2002 | DiLorenzo |
| 6,445,955 B1 | 9/2002 | Michelson et al. |
| 6,449,512 B1 | 9/2002 | Boveja |
| 6,505,074 B2 | 1/2003 | Boveja et al. |
| 6,546,290 B1 | 4/2003 | Shloznikov |
| 6,564,103 B2 | 5/2003 | Fischer et al. |
| 6,579,270 B2 | 6/2003 | Sussman et al. |
| 6,652,449 B1 | 11/2003 | Gross et al. |
| 6,704,603 B1 | 3/2004 | Gesotti |
| 6,731,987 B1 | 5/2004 | McAdams et al. |
| 6,735,474 B1 | 5/2004 | Loeb et al. |
| 6,735,480 B2 | 5/2004 | Giuntoli et al. |
| 6,788,976 B2 | 9/2004 | Gesotti |
| 6,819,956 B2 | 11/2004 | DiLorenzo |
| 6,829,510 B2 | 12/2004 | Nathan et al. |
| 6,836,684 B1 | 12/2004 | Rijkhoff et al. |
| 6,862,480 B2 | 3/2005 | Cohen et al. |
| 6,892,098 B2 | 5/2005 | Ayal et al. |
| 6,937,905 B2 | 8/2005 | Carroll et al. |
| 6,959,215 B2 | 10/2005 | Gliner et al. |
| 6,959,216 B2 | 10/2005 | Faghri |
| 6,988,005 B2 | 1/2006 | McGraw et al. |
| 7,010,352 B2 | 3/2006 | Hogan |
| 7,089,061 B2 | 8/2006 | Grey |
| 7,146,220 B2 | 12/2006 | Dar et al. |
| 7,162,305 B2 | 1/2007 | Tong et al. |
| 7,171,266 B2 | 1/2007 | Gruzdowich et al. |
| 7,177,694 B2 | 2/2007 | Elbaum |
| 7,177,703 B2 | 2/2007 | Boveja et al. |
| 7,209,787 B2 | 4/2007 | DiLorenzo |
| 7,228,178 B2 | 6/2007 | Carroll et al. |
| 7,231,254 B2 | 6/2007 | DiLorenzo |
| 7,236,830 B2 | 6/2007 | Gliner |
| 7,254,444 B2 | 8/2007 | Moore et al. |
| 7,277,758 B2 | 10/2007 | DiLorenzo |
| 7,324,851 B1 | 1/2008 | DiLorenzo |
| 7,326,235 B2 | 2/2008 | Edwards |
| 7,328,068 B2 | 2/2008 | Spinelli et al. |
| 7,349,739 B2 | 3/2008 | Harry et al. |
| 7,353,064 B2 | 4/2008 | Gliner et al. |
| 7,369,896 B2 | 5/2008 | Gesotti |
| 7,499,747 B2 | 3/2009 | Kieval et al. |
| 7,529,582 B1 | 5/2009 | DiLorenzo |
| 7,558,610 B1 | 7/2009 | Odderson |
| 7,636,602 B2 | 12/2009 | Baru Fassio et al. |
| 7,643,880 B2 | 1/2010 | Tanagho et al. |
| 7,643,882 B2 | 1/2010 | Boston |
| 7,647,112 B2 | 1/2010 | Tracey et al. |
| 7,650,190 B2 | 1/2010 | Zhou et al. |
| 7,742,820 B2 | 6/2010 | Wyler et al. |
| 7,761,166 B2 | 7/2010 | Giftakis et al. |
| 7,769,464 B2 | 8/2010 | Gerber et al. |
| 7,857,771 B2 | 12/2010 | Alwan et al. |
| 7,899,556 B2 | 3/2011 | Nathan et al. |
| 7,917,201 B2 | 3/2011 | Gozani et al. |
| 7,930,034 B2 | 4/2011 | Gerber |
| 7,949,403 B2 | 5/2011 | Palermo et al. |
| 7,957,814 B2 | 6/2011 | Goetz et al. |
| 7,974,696 B1 | 7/2011 | DiLorenzo |
| 7,974,698 B2 | 7/2011 | Tass et al. |
| 7,996,088 B2 | 8/2011 | Marrosu et al. |
| 7,998,092 B2 | 8/2011 | Avni et al. |
| 8,000,796 B2 | 8/2011 | Tass et al. |
| 8,025,632 B2 | 9/2011 | Einarsson |
| 8,046,083 B2 | 10/2011 | Teganthoff et al. |
| 8,075,499 B2 | 12/2011 | Nathan et al. |
| 8,086,318 B2 | 12/2011 | Strother et al. |
| 8,121,694 B2 | 2/2012 | Molnar et al. |
| 8,145,316 B2 | 3/2012 | Deem et al. |
| 8,165,668 B2 | 4/2012 | Dacey, Jr. et al. |
| 8,175,718 B2 | 5/2012 | Wahlgren et al. |
| 8,187,209 B1 | 5/2012 | Guiffrida et al. |
| 8,219,188 B2 | 7/2012 | Craig |
| 8,233,988 B2 | 7/2012 | Errico et al. |
| 8,260,439 B2 | 9/2012 | Diubaldi et al. |
| 8,301,215 B2 | 10/2012 | Lee |
| 8,306,624 B2 | 11/2012 | Gerber et al. |
| 8,313,443 B2 | 11/2012 | Tom |
| 8,343,026 B2 | 1/2013 | Gardiner et al. |
| 8,364,257 B2 | 1/2013 | Van Den Eerenbeemd et al. |

(56) References Cited

U.S. PATENT DOCUMENTS

| | | |
|---|---|---|
| 8,374,701 B2 | 2/2013 | Hyde et al. |
| 8,380,314 B2 | 2/2013 | Panken et al. |
| 8,382,688 B2 | 2/2013 | Dar et al. |
| 8,391,970 B2 | 3/2013 | Tracey et al. |
| 8,396,556 B2 | 3/2013 | Libbus et al. |
| 8,409,116 B2 | 4/2013 | Wang et al. |
| 8,412,338 B2 | 4/2013 | Faltys |
| 8,414,507 B2 | 4/2013 | Asada |
| 8,428,719 B2 | 4/2013 | Napadow |
| 8,435,166 B2 | 5/2013 | Burnett et al. |
| 8,447,411 B2 | 5/2013 | Skelton et al. |
| 8,452,410 B2 | 5/2013 | Emborg et al. |
| 8,463,374 B2 | 6/2013 | Hudson et al. |
| 8,473,064 B2 | 6/2013 | Castel et al. |
| 8,548,594 B2 | 10/2013 | Thimineur et al. |
| 8,571,687 B2 | 10/2013 | Libbus et al. |
| 8,581,731 B2 | 11/2013 | Purks et al. |
| 8,583,238 B1 | 11/2013 | Heldman et al. |
| 8,588,884 B2 | 11/2013 | Hegde et al. |
| 8,588,917 B2 | 11/2013 | Whitehurst et al. |
| 8,608,671 B2 | 12/2013 | Kinoshita et al. |
| 8,626,305 B2 | 1/2014 | Nielsen et al. |
| 8,639,342 B2 | 1/2014 | Possover |
| 8,644,904 B2 | 2/2014 | Chang et al. |
| 8,644,938 B2 | 2/2014 | Craggs |
| 8,660,656 B2 | 2/2014 | Moser et al. |
| 8,666,496 B2 | 3/2014 | Simon et al. |
| 8,679,038 B1 | 3/2014 | Giuffrida |
| 8,682,441 B2 | 3/2014 | De Ridder |
| 8,688,220 B2 | 4/2014 | Degiorgio et al. |
| 8,694,104 B2 | 4/2014 | Libbus et al. |
| 8,694,110 B2 | 4/2014 | Nathan et al. |
| 8,702,584 B2 | 4/2014 | Rigaux et al. |
| 8,702,629 B2 | 4/2014 | Giuffrida et al. |
| 8,706,241 B2 | 4/2014 | Firlik et al. |
| 8,718,780 B2 | 5/2014 | Lee |
| 8,740,825 B2 | 6/2014 | Ehrenreich et al. |
| 8,744,587 B2 | 6/2014 | Miesel et al. |
| 8,755,892 B2 | 6/2014 | Amurthur et al. |
| 8,768,452 B2 | 7/2014 | Gerber |
| 8,788,045 B2 | 7/2014 | Gross et al. |
| 8,788,049 B2 | 7/2014 | Lasko et al. |
| 8,792,977 B2 | 7/2014 | Kakei et al. |
| 8,798,698 B2 | 8/2014 | Kim et al. |
| 8,821,416 B2 | 9/2014 | Johansson et al. |
| 8,825,163 B2 | 9/2014 | Grill et al. |
| 8,825,165 B2 | 9/2014 | Possover |
| 8,843,201 B1 | 9/2014 | Heldman et al. |
| 8,845,494 B2 | 9/2014 | Whitall et al. |
| 8,845,557 B1 | 9/2014 | Giuffrida et al. |
| 8,855,775 B2 | 10/2014 | Leyde |
| 8,862,238 B2 | 10/2014 | Rahimi et al. |
| 8,862,247 B2 | 10/2014 | Schoendorf et al. |
| 8,868,177 B2 | 10/2014 | Simon et al. |
| 8,874,227 B2 | 10/2014 | Simon et al. |
| 8,880,175 B2 | 11/2014 | Simon |
| 8,886,321 B2 | 11/2014 | Rohrer et al. |
| 8,892,200 B2 | 11/2014 | Wagner et al. |
| 8,897,870 B2 | 11/2014 | De Ridder |
| 8,903,494 B2 | 12/2014 | Goldwasser et al. |
| 8,920,345 B2 | 12/2014 | Greenberg et al. |
| 8,923,970 B2 | 12/2014 | Bar-Yoseph et al. |
| 8,948,876 B2 | 2/2015 | Gozani et al. |
| 8,961,439 B2 | 2/2015 | Yang et al. |
| 8,972,017 B2 | 3/2015 | Dar et al. |
| 8,989,861 B2 | 3/2015 | Su et al. |
| 9,002,477 B2 | 4/2015 | Burnett |
| 9,005,102 B2 | 4/2015 | Burnett et al. |
| 9,008,781 B2 | 4/2015 | Ahmed |
| 9,011,310 B2 | 4/2015 | Ahmed |
| 9,017,273 B2 | 4/2015 | Burbank et al. |
| 9,026,216 B2 | 5/2015 | Rossi et al. |
| 9,042,988 B2 | 5/2015 | Dilorenzo |
| 9,060,747 B2 | 6/2015 | Salorio |
| 9,089,691 B2 | 7/2015 | Libbus et al. |
| 9,095,351 B2 | 8/2015 | Sachs et al. |
| 9,095,417 B2 | 8/2015 | Dar et al. |
| 9,107,614 B2 | 8/2015 | Halkias et al. |
| 9,119,964 B2 | 9/2015 | Marnfeldt |
| 9,155,885 B2 | 10/2015 | Wei et al. |
| 9,155,890 B2 | 10/2015 | Guntinas-Lichius et al. |
| 9,162,059 B1 | 10/2015 | Lindenthaler |
| 9,168,374 B2 | 10/2015 | Su |
| 9,174,045 B2 | 11/2015 | Simon et al. |
| 9,186,095 B2 | 11/2015 | Machado et al. |
| 9,192,763 B2 | 11/2015 | Gerber et al. |
| 9,220,895 B2 | 12/2015 | Siff et al. |
| 9,227,056 B1 | 1/2016 | Heldman et al. |
| 9,238,142 B2 | 1/2016 | Heldman et al. |
| 9,242,085 B2 | 1/2016 | Hershey et al. |
| 9,248,285 B2 | 2/2016 | Haessler |
| 9,248,286 B2 | 2/2016 | Simon et al. |
| 9,248,297 B2 | 2/2016 | Hoyer et al. |
| 9,254,382 B2 | 2/2016 | Ahmad et al. |
| 9,259,577 B2 | 2/2016 | Kaula et al. |
| 9,265,927 B2 | 2/2016 | Yonce et al. |
| 9,282,928 B1 | 3/2016 | Giffrida |
| 9,289,607 B2 | 3/2016 | Su et al. |
| 9,301,712 B2 | 4/2016 | McNames et al. |
| 9,302,046 B1 | 4/2016 | Giuffrida et al. |
| 9,314,190 B1 | 4/2016 | Giuffrida et al. |
| 9,314,622 B2 | 4/2016 | Embrey et al. |
| 9,332,918 B1 | 5/2016 | Buckley et al. |
| 9,339,641 B2 | 5/2016 | Rajguru et al. |
| 9,345,872 B2 | 5/2016 | Groteke |
| 9,364,657 B2 | 6/2016 | Kiani et al. |
| 9,364,672 B2 | 6/2016 | Marnfeldt |
| 9,375,570 B2 | 6/2016 | Kiani et al. |
| 9,408,683 B2 | 8/2016 | St. Anne et al. |
| 9,414,776 B2 | 8/2016 | Sillay et al. |
| 9,452,287 B2 | 9/2016 | Rosenbluth et al. |
| 9,468,753 B2 | 10/2016 | Fisher et al. |
| 9,474,898 B2 | 10/2016 | Gozani et al. |
| 9,549,872 B2 | 1/2017 | Chen et al. |
| 9,586,038 B1 | 3/2017 | Kosierkiewicz |
| 9,597,509 B2 | 3/2017 | Hoffer et al. |
| 9,675,800 B2 | 6/2017 | Li et al. |
| 9,782,584 B2 | 10/2017 | Cartledge et al. |
| 9,802,041 B2 | 10/2017 | Wong et al. |
| 9,861,283 B1 | 1/2018 | Giuffrida |
| 9,877,679 B1 | 1/2018 | Giuffrida |
| 9,877,680 B1 | 1/2018 | Giuffrida et al. |
| 9,924,899 B2 | 3/2018 | Pracar et al. |
| 9,974,478 B1 | 5/2018 | Brokaw et al. |
| 9,980,659 B2 | 5/2018 | Sadeghian-Motahar et al. |
| 10,004,900 B2 | 6/2018 | Kent et al. |
| 10,022,545 B1 | 7/2018 | Giuffrida |
| 10,028,695 B2 | 7/2018 | Machado et al. |
| 10,130,809 B2 | 11/2018 | Cartledge et al. |
| 10,173,060 B2 | 1/2019 | Wong et al. |
| 10,179,238 B2 | 1/2019 | Wong et al. |
| 10,213,602 B2 | 2/2019 | Ironi et al. |
| 10,549,093 B2 | 2/2020 | Wong et al. |
| 10,561,839 B2 | 2/2020 | Wong et al. |
| 10,603,482 B2 | 3/2020 | Hamner et al. |
| 10,625,074 B2 | 4/2020 | Rosenbluth et al. |
| 2002/0161415 A1 | 10/2002 | Cohen et al. |
| 2002/0165586 A1 | 11/2002 | Hill et al. |
| 2002/0177882 A1 | 11/2002 | DiLorenzo |
| 2003/0032992 A1 | 2/2003 | Thacker et al. |
| 2003/0045922 A1 | 3/2003 | Northrop |
| 2003/0088294 A1 | 5/2003 | Gesotti |
| 2003/0093098 A1 | 5/2003 | Heitzmann et al. |
| 2003/0149457 A1 | 8/2003 | Tcheng et al. |
| 2003/0181959 A1 | 9/2003 | Dobak, III |
| 2003/0187483 A1 | 10/2003 | Grey et al. |
| 2003/0195583 A1 | 10/2003 | Gruzdowich et al. |
| 2004/0015094 A1 | 1/2004 | Manabe et al. |
| 2004/0088025 A1 | 5/2004 | Gessotti |
| 2004/0093093 A1 | 5/2004 | Andrews |
| 2004/0127939 A1 | 7/2004 | Grey et al. |
| 2004/0133249 A1 | 7/2004 | Gesotti |
| 2004/0167588 A1 | 8/2004 | Bertolucci |
| 2004/0249416 A1 | 12/2004 | Yun et al. |

(56) References Cited

U.S. PATENT DOCUMENTS

| | | |
|---|---|---|
| 2004/0267331 A1 | 12/2004 | Koeneman et al. |
| 2005/0021103 A1 | 1/2005 | DiLorenzo |
| 2005/0055063 A1 | 3/2005 | Loeb et al. |
| 2005/0065553 A1 | 3/2005 | Ben Ezra et al. |
| 2005/0075502 A1 | 4/2005 | Shafer |
| 2005/0171577 A1 | 8/2005 | Cohen et al. |
| 2005/0234309 A1 | 10/2005 | Klapper |
| 2006/0047326 A1 | 3/2006 | Wheeler |
| 2006/0052726 A1 | 3/2006 | Weisz et al. |
| 2006/0095088 A1 | 5/2006 | De Ridder |
| 2006/0161218 A1 | 7/2006 | Danilov |
| 2006/0173509 A1 | 8/2006 | Lee et al. |
| 2006/0184059 A1 | 8/2006 | Jadidi |
| 2006/0217781 A1 | 9/2006 | John |
| 2006/0224191 A1 | 10/2006 | DiLorenzo |
| 2006/0229678 A1 | 10/2006 | Lee |
| 2006/0253167 A1 | 11/2006 | Kurtz et al. |
| 2006/0276853 A1 | 12/2006 | Tass |
| 2006/0293723 A1 | 12/2006 | Whitehurst et al. |
| 2007/0027486 A1 | 2/2007 | Armstrong |
| 2007/0073361 A1 | 3/2007 | Goren et al. |
| 2007/0123951 A1 | 5/2007 | Boston |
| 2007/0123952 A1 | 5/2007 | Strother et al. |
| 2007/0142862 A1 | 6/2007 | DiLorenzo |
| 2007/0156179 A1 | 7/2007 | Karashurov |
| 2007/0156182 A1 | 7/2007 | Castel et al. |
| 2007/0156183 A1 | 7/2007 | Rhodes |
| 2007/0156200 A1 | 7/2007 | Kornet et al. |
| 2007/0173899 A1 | 7/2007 | Levin et al. |
| 2007/0173903 A1 | 7/2007 | Goren et al. |
| 2007/0203533 A1 | 8/2007 | Goren et al. |
| 2007/0207193 A1 | 9/2007 | Zasler et al. |
| 2007/0282228 A1 | 12/2007 | Einav et al. |
| 2008/0004672 A1 | 1/2008 | Dalal et al. |
| 2008/0009772 A1 | 1/2008 | Tyler et al. |
| 2008/0021505 A1 | 1/2008 | Hastings et al. |
| 2008/0027507 A1 | 1/2008 | Bijelic et al. |
| 2008/0033259 A1 | 2/2008 | Manto et al. |
| 2008/0033504 A1 | 2/2008 | Bertolucci |
| 2008/0051839 A1 | 2/2008 | Libbus et al. |
| 2008/0058773 A1 | 3/2008 | John |
| 2008/0058893 A1 | 3/2008 | Noujokat |
| 2008/0147146 A1 | 6/2008 | Wahlgren et al. |
| 2008/0177398 A1 | 7/2008 | Gross et al. |
| 2008/0195007 A1 | 8/2008 | Podrazhansky et al. |
| 2008/0208288 A1 | 8/2008 | Podrazhansky et al. |
| 2008/0216593 A1 | 9/2008 | Jacobsen et al. |
| 2008/0288016 A1 | 11/2008 | Amurthur et al. |
| 2008/0312520 A1 | 12/2008 | Rowlandson et al. |
| 2009/0018609 A1 | 1/2009 | DiLorenzo |
| 2009/0076565 A1 | 3/2009 | Surwit |
| 2009/0105785 A1 | 4/2009 | Wei et al. |
| 2009/0112133 A1 | 4/2009 | Deisseroth et al. |
| 2009/0157138 A1 | 6/2009 | Errico et al. |
| 2009/0187121 A1 | 7/2009 | Evans |
| 2009/0216294 A1 | 8/2009 | Ewing et al. |
| 2009/0247910 A1 | 10/2009 | Klapper |
| 2009/0299435 A1 | 12/2009 | Gliner et al. |
| 2009/0318986 A1 | 12/2009 | Alo et al. |
| 2009/0326595 A1 | 12/2009 | Brockway et al. |
| 2009/0326607 A1 | 12/2009 | Castel et al. |
| 2010/0010381 A1 | 1/2010 | Skelton et al. |
| 2010/0010572 A1 | 1/2010 | Skelton et al. |
| 2010/0057154 A1 | 3/2010 | Dietrich et al. |
| 2010/0099963 A1 | 4/2010 | Kilger |
| 2010/0107657 A1 | 5/2010 | Vistakula |
| 2010/0125220 A1 | 5/2010 | Seong |
| 2010/0152817 A1 | 6/2010 | Gillbe |
| 2010/0174342 A1 | 7/2010 | Boston et al. |
| 2010/0222630 A1 | 9/2010 | Mangrum et al. |
| 2010/0227330 A1 | 9/2010 | Fink et al. |
| 2010/0249637 A1 | 9/2010 | Walter et al. |
| 2010/0292527 A1 | 11/2010 | Schneider et al. |
| 2010/0298905 A1 | 11/2010 | Simon |
| 2010/0324611 A1 | 12/2010 | Deming et al. |
| 2011/0009920 A1 | 1/2011 | Whitehurst et al. |
| 2011/0021899 A1 | 1/2011 | Arps et al. |
| 2011/0040204 A1 | 2/2011 | Ivorra et al. |
| 2011/0054358 A1 | 3/2011 | Kim et al. |
| 2011/0071590 A1 | 3/2011 | Mounaim et al. |
| 2011/0098780 A1 | 4/2011 | Graupe et al. |
| 2011/0118805 A1 | 5/2011 | Wei et al. |
| 2011/0125212 A1 | 5/2011 | Tyler |
| 2011/0137375 A1 | 6/2011 | McBride |
| 2011/0184489 A1 | 7/2011 | Nicolelis et al. |
| 2011/0202107 A1 | 8/2011 | Sunagawa et al. |
| 2011/0213278 A1 | 9/2011 | Horak et al. |
| 2011/0224571 A1 | 9/2011 | Pascual-Leone et al. |
| 2011/0230701 A1 | 9/2011 | Simon et al. |
| 2011/0245734 A1 | 10/2011 | Wagner et al. |
| 2011/0250297 A1 | 10/2011 | Oronsky et al. |
| 2011/0282412 A1 | 11/2011 | Glukhovsky et al. |
| 2011/0301663 A1 | 12/2011 | Wang et al. |
| 2012/0010492 A1 | 1/2012 | Thramann et al. |
| 2012/0053491 A1 | 3/2012 | Nathan et al. |
| 2012/0078319 A1 | 3/2012 | De Ridder |
| 2012/0088986 A1 | 4/2012 | David et al. |
| 2012/0092178 A1 | 4/2012 | Callsen et al. |
| 2012/0109013 A1 | 5/2012 | Everett et al. |
| 2012/0136410 A1 | 5/2012 | Rezai et al. |
| 2012/0158094 A1 | 6/2012 | Kramer et al. |
| 2012/0184801 A1 | 7/2012 | Simon et al. |
| 2012/0185020 A1 | 7/2012 | Simon et al. |
| 2012/0220812 A1 | 8/2012 | Mishelevich |
| 2012/0239112 A1 | 9/2012 | Muraoka |
| 2012/0259255 A1 | 10/2012 | Tomlinson et al. |
| 2012/0277621 A1 | 11/2012 | Gerber et al. |
| 2012/0302821 A1 | 11/2012 | Burnett |
| 2012/0310298 A1 | 12/2012 | Besio et al. |
| 2012/0310303 A1 | 12/2012 | Popovic et al. |
| 2012/0330182 A1 | 12/2012 | Alberts et al. |
| 2013/0006322 A1 | 1/2013 | Tai |
| 2013/0060124 A1 | 3/2013 | Zietsma |
| 2013/0066388 A1 | 3/2013 | Bernhard et al. |
| 2013/0066395 A1 | 3/2013 | Simon et al. |
| 2013/0085317 A1 | 4/2013 | Feinstein |
| 2013/0090519 A1 | 4/2013 | Tass |
| 2013/0116606 A1 | 5/2013 | Cordo |
| 2013/0123568 A1 | 5/2013 | Hamilton et al. |
| 2013/0123666 A1 | 5/2013 | Giuffrida et al. |
| 2013/0131484 A1 | 5/2013 | Pernu |
| 2013/0158624 A1 | 6/2013 | Bain et al. |
| 2013/0158627 A1 | 6/2013 | Gozani et al. |
| 2013/0231713 A1 | 9/2013 | De Ridder et al. |
| 2013/0236867 A1 | 9/2013 | Avni et al. |
| 2013/0238049 A1 | 9/2013 | Simon et al. |
| 2013/0245486 A1 | 9/2013 | Simon et al. |
| 2013/0245713 A1 | 9/2013 | Tass |
| 2013/0253299 A1 | 9/2013 | Weber et al. |
| 2013/0267759 A1 | 10/2013 | Jin |
| 2013/0281890 A1 | 10/2013 | Mishelevich |
| 2013/0289647 A1 | 10/2013 | Bhadra et al. |
| 2013/0296967 A1 | 11/2013 | Skaribas et al. |
| 2013/0297022 A1 | 11/2013 | Pathak |
| 2013/0331907 A1 | 12/2013 | Sumners et al. |
| 2013/0333094 A1 | 12/2013 | Rogers et al. |
| 2013/0338726 A1 | 12/2013 | Machado |
| 2014/0025059 A1 | 1/2014 | Kerr |
| 2014/0031605 A1 | 1/2014 | Schneider |
| 2014/0039573 A1 | 2/2014 | Jindra |
| 2014/0039575 A1 | 2/2014 | Bradley |
| 2014/0046423 A1 | 2/2014 | Rajguru et al. |
| 2014/0058189 A1 | 2/2014 | Stubbeman |
| 2014/0067003 A1 | 3/2014 | Vase et al. |
| 2014/0078694 A1 | 3/2014 | Wissmar |
| 2014/0081345 A1 | 3/2014 | Hershey |
| 2014/0094675 A1 | 4/2014 | Luna et al. |
| 2014/0094873 A1 | 4/2014 | Emborg et al. |
| 2014/0128939 A1 | 5/2014 | Embrey et al. |
| 2014/0132410 A1 | 5/2014 | Chang |
| 2014/0142654 A1 | 5/2014 | Simon et al. |
| 2014/0148873 A1 | 5/2014 | Kirn |
| 2014/0163444 A1 | 6/2014 | Ingvarsson |
| 2014/0171834 A1 | 6/2014 | DeGoede et al. |

(56) References Cited

U.S. PATENT DOCUMENTS

| | | |
|---|---|---|
| 2014/0214119 A1 | 7/2014 | Greiner et al. |
| 2014/0228927 A1 | 8/2014 | Ahmad et al. |
| 2014/0236258 A1 | 8/2014 | Carroll et al. |
| 2014/0249452 A1 | 9/2014 | Marsh et al. |
| 2014/0257047 A1 | 9/2014 | Slliay et al. |
| 2014/0257129 A1 | 9/2014 | Choi et al. |
| 2014/0276194 A1 | 9/2014 | Osorio |
| 2014/0277220 A1 | 9/2014 | Brennan et al. |
| 2014/0296752 A1 | 10/2014 | Edgerton et al. |
| 2014/0296934 A1 | 10/2014 | Gozani et al. |
| 2014/0296935 A1 | 10/2014 | Ferree et al. |
| 2014/0300490 A1 | 10/2014 | Kotz et al. |
| 2014/0309709 A1 | 10/2014 | Gozanl et al. |
| 2014/0316484 A1 | 10/2014 | Edgerton et al. |
| 2014/0324118 A1 | 10/2014 | Simon et al. |
| 2014/0330068 A1 | 11/2014 | Partsch et al. |
| 2014/0330335 A1 | 11/2014 | Errico et al. |
| 2014/0336003 A1 | 11/2014 | Franz et al. |
| 2014/0336722 A1 | 11/2014 | Rocon De Lima et al. |
| 2014/0343462 A1 | 11/2014 | Burnet |
| 2014/0350436 A1 | 11/2014 | Nathan et al. |
| 2014/0358040 A1 | 12/2014 | Kim et al. |
| 2014/0364678 A1 | 12/2014 | Harry et al. |
| 2015/0004656 A1 | 1/2015 | Tang et al. |
| 2015/0005852 A1 | 1/2015 | Hershey et al. |
| 2015/0012067 A1 | 1/2015 | Bradley et al. |
| 2015/0038886 A1 | 2/2015 | Snow |
| 2015/0044656 A1 | 2/2015 | Eichhorn et al. |
| 2015/0057506 A1 | 2/2015 | Luna et al. |
| 2015/0073310 A1 | 3/2015 | Pracar et al. |
| 2015/0080979 A1 | 3/2015 | Lasko et al. |
| 2015/0100004 A1 | 4/2015 | Goldman et al. |
| 2015/0100104 A1 | 4/2015 | Kiani et al. |
| 2015/0100105 A1 | 4/2015 | Kiani et al. |
| 2015/0148866 A1 | 5/2015 | Bulsen et al. |
| 2015/0148878 A1 | 5/2015 | Yoo et al. |
| 2015/0157274 A1 | 6/2015 | Ghassemzadeh et al. |
| 2015/0164377 A1 | 6/2015 | Nathan et al. |
| 2015/0164401 A1 | 6/2015 | Toth et al. |
| 2015/0190085 A1 | 7/2015 | Nathan et al. |
| 2015/0190634 A1 | 7/2015 | Rezai et al. |
| 2015/0202444 A1 | 7/2015 | Franke et al. |
| 2015/0208955 A1 | 7/2015 | Smith |
| 2015/0216475 A1 | 8/2015 | Luna et al. |
| 2015/0230733 A1 | 8/2015 | Heo et al. |
| 2015/0230756 A1 | 8/2015 | Luna et al. |
| 2015/0277559 A1 | 10/2015 | Vescovi et al. |
| 2015/0321000 A1 | 11/2015 | Rosenbluth et al. |
| 2015/0335882 A1 | 11/2015 | Gross et al. |
| 2016/0001096 A1 | 1/2016 | Mishelevich |
| 2016/0008620 A1 | 1/2016 | Stubbeman |
| 2016/0016014 A1 | 1/2016 | Wagner et al. |
| 2016/0022987 A1 | 1/2016 | Zschaeck et al. |
| 2016/0022989 A1 | 1/2016 | Pfeifer |
| 2016/0038059 A1 | 2/2016 | Asada et al. |
| 2016/0045140 A1 | 2/2016 | Kitamura et al. |
| 2016/0089045 A1 | 3/2016 | Sadeghian-Motahar et al. |
| 2016/0106344 A1 | 4/2016 | Nazari |
| 2016/0121110 A1 | 5/2016 | Kent et al. |
| 2016/0128621 A1 | 5/2016 | Machado et al. |
| 2016/0129248 A1 | 5/2016 | Creasey et al. |
| 2016/0158542 A1 | 6/2016 | Ahmed |
| 2016/0158565 A1 | 6/2016 | Lee |
| 2016/0198998 A1 | 7/2016 | Rahimi et al. |
| 2016/0220836 A1 | 8/2016 | Parks |
| 2016/0262685 A1 | 9/2016 | Wagner et al. |
| 2016/0287879 A1 | 10/2016 | Denison et al. |
| 2016/0339239 A1 | 11/2016 | Yoo et al. |
| 2016/0339239 A1 | 11/2016 | Yoo et al. |
| 2017/0014625 A1 | 1/2017 | Rosenbluth et al. |
| 2017/0027812 A1 | 2/2017 | Hyde et al. |
| 2017/0056238 A1 | 3/2017 | Yi et al. |
| 2017/0079597 A1 | 3/2017 | Horne |
| 2017/0080207 A1 | 3/2017 | Perez et al. |
| 2017/0266443 A1 | 9/2017 | Rajguru et al. |
| 2017/0274208 A1 | 9/2017 | Nagel et al. |
| 2017/0287146 A1 | 10/2017 | Pathak et al. |
| 2017/0312505 A1 | 11/2017 | Ahmed |
| 2018/0049676 A1 | 2/2018 | Griffiths et al. |
| 2018/0064344 A1 | 3/2018 | Nguyen |
| 2018/0064944 A1 | 3/2018 | Grill et al. |
| 2018/0168905 A1 | 6/2018 | Goodall et al. |
| 2018/0169400 A1 | 6/2018 | Wong et al. |
| 2018/0214694 A1 | 8/2018 | Parramon |
| 2018/0221620 A1 | 8/2018 | Metzger |
| 2018/0235500 A1 | 8/2018 | Lee et al. |
| 2018/0264263 A1 | 9/2018 | Rosenbluth et al. |
| 2019/0001117 A1 | 1/2019 | Ben-David et al. |
| 2019/0001129 A1 | 1/2019 | Rosenbluth et al. |
| 2019/0134393 A1 | 5/2019 | Wong et al. |
| 2020/0093400 A1 | 3/2020 | Hamner et al. |

FOREIGN PATENT DOCUMENTS

| | | |
|---|---|---|
| EP | 0000759 | 2/1979 |
| EP | 0725665 | 1/1998 |
| EP | 1062988 | 12/2000 |
| EP | 1558333 | 5/2007 |
| EP | 2383014 | 11/2011 |
| EP | 2801389 | 11/2014 |
| EP | 3020448 | 5/2016 |
| ES | 2222819 | 3/2006 |
| ES | 2272137 | 6/2008 |
| GB | 2496449 | 5/2013 |
| JP | 2002/200178 | 7/2002 |
| JP | 2003-501207 | 1/2003 |
| JP | 2006-503658 | 2/2006 |
| JP | 2008/018235 | 1/2008 |
| JP | 2009/34328 | 2/2009 |
| JP | 2009/529352 | 8/2009 |
| JP | 2010/506618 | 3/2010 |
| JP | 2010/512926 | 4/2010 |
| JP | 2012/005596 | 1/2012 |
| JP | 2012/055650 | 3/2012 |
| JP | 2013/017609 | 1/2013 |
| JP | 2013/094305 | 5/2013 |
| JP | 54-39921 | 3/2014 |
| WO | WO1994/000187 | 1/1994 |
| WO | WO1994/017855 | 8/1994 |
| WO | WO1996/032909 | 10/1996 |
| WO | WO1998/043700 | 10/1998 |
| WO | WO1999/019019 | 4/1999 |
| WO | WO2000/015293 | 3/2000 |
| WO | WO2002/017987 | 3/2002 |
| WO | WO2005/122894 | 12/2005 |
| WO | WO2007/112092 | 10/2007 |
| WO | WO2009/153730 | 12/2009 |
| WO | WO2010/111321 | 9/2010 |
| WO | WO2010/141155 | 12/2010 |
| WO | WO2011/119224 | 9/2011 |
| WO | WO2011/144883 | 11/2011 |
| WO | WO2012/040243 | 3/2012 |
| WO | WO2013/071307 | 5/2013 |
| WO | WO2013/074809 | 5/2013 |
| WO | WO2014/043757 | 3/2014 |
| WO | WO2014/053041 | 4/2014 |
| WO | WO2014/113813 | 7/2014 |
| WO | WO2014/146082 | 9/2014 |
| WO | WO2014/151431 | 9/2014 |
| WO | WO2014/153201 | 9/2014 |
| WO | WO2014/207512 | 12/2014 |
| WO | WO2015/033152 | 3/2015 |
| WO | WO2015/039206 | 3/2015 |
| WO | WO2015/039244 | 3/2015 |
| WO | WO2015/042365 | 3/2015 |
| WO | WO2015/079319 | 6/2015 |
| WO | WO2015/095880 | 6/2015 |
| WO | WO2015/128090 | 9/2015 |
| WO | WO2015/164706 | 10/2015 |
| WO | WO2015/187712 | 12/2015 |
| WO | WO2016/007093 | 1/2016 |
| WO | WO2016/019250 | 2/2016 |
| WO | WO2016/094728 | 6/2016 |
| WO | WO2016/102958 | 6/2016 |

(56) References Cited

FOREIGN PATENT DOCUMENTS

| WO | WO2016/110804 | 7/2016 |
|---|---|---|
| WO | WO2016/128985 | 8/2016 |
| WO | WO2016/149751 | 9/2016 |
| WO | WO2016/166281 | 10/2016 |
| WO | WO2016/179407 | 11/2016 |
| WO | WO2016/189422 | 12/2016 |
| WO | WO2016/195587 | 12/2016 |
| WO | WO2016/201366 | 12/2016 |
| WO | WO2017/004021 | 1/2017 |
| WO | WO2017/010930 | 1/2017 |
| WO | WO2017/023864 | 2/2017 |
| WO | WO2017/053847 | 3/2017 |
| WO | WO2017/062994 | 4/2017 |
| WO | WO2017/086798 | 5/2017 |
| WO | WO2017/088573 | 6/2017 |
| WO | WO2017/132067 | 8/2017 |
| WO | WO2017/199026 | 11/2017 |
| WO | WO2017/208167 | 12/2017 |
| WO | WO2017/209673 | 12/2017 |
| WO | WO2017/210729 | 12/2017 |
| WO | WO2017/221037 | 12/2017 |
| WO | WO2018/009680 | 1/2018 |
| WO | WO2018/028170 | 2/2018 |
| WO | WO2018/028220 | 2/2018 |
| WO | WO2018/028221 | 2/2018 |
| WO | WO2018/039458 | 3/2018 |
| WO | WO2018/093765 | 5/2018 |
| WO | WO2018/112164 | 6/2018 |
| WO | WO2018/187241 | 10/2018 |
| WO | WO2019/005774 | 1/2019 |
| WO | WO2019/014250 | 1/2019 |
| WO | WO 2019/143790 | 7/2019 |
| WO | WO 2019/213433 | 11/2019 |
| WO | WO 2020/006048 | 1/2020 |
| WO | WO 2020/069219 | 4/2020 |
| WO | WO 2020/086726 | 4/2020 |

OTHER PUBLICATIONS

U.S. Appl. No. 16/327,780, filed Feb. 22, 2019, Hamner et al.
Apartis; Clinical neurophysiology in movement disorders. Handb Clin Neurol; 111; Pediatric Neurology Pt. 1; pp. 87-92;Apr. 2013.
Australian Office Action dated Apr. 9, 2019 in Australian Patent Application No. 2015271774 in 3 pages.
Australian Office Action dated Mar. 13, 2020 in Australian Patent Application No. 2015271774 in 3 pages.
Barbaud et al.; Improvement in essential tremor after pure sensory stroke due to thalamic infarction; European neurology; 46; pp. 57-59; Jul. 2001.
Barrios et al.: BCI algorithms for tremor identification, characterization and tracking; Seventh Framework Programme, EU; Contract No. FP7-ICT-2007-224051 (v3.0); 57 pgs.; Jul. 10, 2011.
Bartley et al.; Neuromodulation for overactive bladder; Nature Reviews Urology; 10; pp. 513-521; Sep. 2013.
Benabid et al.; A putative generalized model of the effects and mechanism of action of high frequency electrical stimulation of the central nervous system; Acta Neural Belg; 105(3); pp. 149-157; Sep. 2005.
Bergquist et al.: Motor unit recruitment when neuromuscular electrical stimulation is applied over a nerve trunk compared with a muscle belly: quadriceps femoris, Journal of Applied Physiology; vol. 113, No. 1, pp. 78-89; Jul. 2012.
Bergquist et al.; Motor unit recruitment when neuromuscular electrical stimulation is applied over a nerve trunk compared with a muscle belly: triceps surae, Journal of Applied Physiology; vol. 110, No. 3, pp. 627-637; Mar. 2011.
Bijelic et al.: E Actitrode®: The New Selective Stimulation Interface for Functional Movements in Hemiplegic Patients; Serbian Journal of Electrical Engineering; 1(3); pp. 21-28; Nov. 2004.
Birdno et al.; Pulse-to-pulse changes in the frequency of deep brain stimulation affect tremor and modeled neuronal activity.; Journal of Neurophysiology; 98; pp. 1675-1684; Jul. 2007.

Birdno et al.; Response of human thalamic neurons to high-frequency stimulation.; PloS One; 9(5); 10 pgs.; May 2014.
Birgersson et al.; Non-invasive bioimpedance of intact skin: mathematical modeling and experiments; Physiological Measurement; 32(1); pp. 1-18; Jan. 2011.
Bohling et al.; Comparison of the stratum corneum thickness measured in vivo with confocal Raman spectroscopy and confocal reflectance microscopy; Skin research and Technology; 20(1); pp. 50-47; Feb. 2014.
Bonaz, B., V. Sinniger, and S. Pellissier. "Vagus nerve stimulation: a new promising therapeutic tool in inflammatory bowel disease." Journal of internal medicine 282.1 (2017): 46-63.
Bowman et al.; Effects of waveform parameters on comfort during transcutaneous neuromuscular electrical stimulation; Annals of Biomedical Engineering; 13(1); pp. 59-74; Jan. 1985.
Bratton et al.; Neural regulation of inflammation: no neural connection from the vagus to splenic sympathetic neurons; Exp Physiol 97.11 (2012); pp. 1180-1185.
Brittain et al.; Tremor suppression by rhythmic transcranial current stimulation; Current Biology; 23; pp. 436-440; Mar. 2013.
Britton et al.; Modulation of postural tremors at the wrist by supramaximal electrical median nerve shocks in ET, PD, and normal subjects mimicking tremor; J Neurology, Neurosurgery, and Psychiatry; 56(10); pp. 1085-1089; Oct. 1993.
Buschbacher et al.; Manual of nerve conduction series; 2nd edition; Demos Medical Publishing, LLC; 2006—Part 1.
Buschbacher et al.; Manual of nerve conduction series; 2nd edition; Demos Medical Publishing, LLC; 2006—Part 2.
Cagnan et al.; Phase dependent modulation of tremor amplitude in essential tremor through thalamic stimulation; Brain; 136(10); pp. 3062-3075; Oct. 2013.
Campero et al.; Peripheral projections of sensory fasicles in the human superificial radial nerve; Brain; 128(Pt 4); pp. 892-895; Apr. 2005.
Chen et al.; A web-based system for home monitoring of patients with Parkinson's disease using wearable sensors; IEEE Trans on Bio-Medical Engineering; 58(3); pp. 831-836; Mar. 2011.
China Office Action and Search Report dated May 28, 2018 in Chinese Patent Application No. 201580029330.6 in 23 pages.
China Office Action dated Feb. 2, 2019 in Chinese Patent Application No. 201580029330.6 in 20 pages.
China Rejection dated Nov. 1, 2019 in Chinese Patent Application No. 201580029330.6 in 17 pages.
Choi, Jong Bo, et al. "Analysis of heart rate variability in female patients with overactive bladder." Urology 65.6 (2005): 1109-1112.
Clair et al.; Postactivation depression and recovery of reflex transmission during repetitive electrical stimulation of the human tibial nerve, Journal of Neurophysiology; vol. 106, No. 1; pp. 184-192; Jul. 2011.
Clar et al.; Skin impedance and moisturization; J. Soc. Cosmet. Chem.; 26; pp. 337-353; 1975; presented at IFSCC Vilith Int'l Congresson Cosmetics Quality and Safety in London on Aug. 26-30, 1974.
Constandinou et al.; A Partial-Current-Steering Biphasic Stimulation Driver for Vestibular Prostheses; IEEE Trans on Biomedical Circuits and Systems; 2(2); pp. 106-113; Jun. 2008.
Daneault et al.; Using a smart phone as a standalone platform for detection and monitoring of pathological tremors; Frontiers in Human Neuroscience; vol. 6, article 357; 12 pgs.; Jan. 2012.
Deuschl et at; Consensus statement of the Movement Disorder Society on Tremor. Ad Hoc Scientific Committee., Movement Disorders, vol. 13 Suppl 3, pp. 2-23; (year of pub. sufficiently earlier than effective US filing date and any foreign priority date)1998.
Di Giovangiulio et al.; The Neuromodulation of the intestinal immune system and its relevance in inflammatory bowel disease; Fronteir's in Immunology; vol. 6; Article 590; Nov. 2015.
Dideriksen et al.; EMG-based characterization of pathological tremor using the iterated Hilbert transform; IEEE transactions on Biomedical Engineering; 58(10); pp. 2911-2921; Oct. 2011.
Dosen et al.: Tremor suppression using electromyography and surface sensory electrical stimulation; Converging Clinical and Engineering Research on Neurorehabilitation; vol. 1 (Siosystems & Biorobotics Series); pp. 539-543; Feb. 2013.

(56) References Cited

OTHER PUBLICATIONS

Doucet et al.; Neuromuscular electrical stimulation for skeletal muscle function; The Yale Journal of Biology and Medicine; 85(2); pp. 201-215; Jun. 2012.
European Office Action dated Jan. 29, 2020 in European Patent Application No. 15802810.0 in 4 pages.
Extended European Search Report dated Jul. 25, 2016 in European Application No. 14740684.7 in 7 pages.
Extended European Search Report dated Oct. 12, 2017 in European Application No. 15802810.0 in 7 pages.
Fuentes et al.; Restoration of locomotive function in Parkinson's disease by spinal cord stimulation: mechanistic approach, Eur J Neurosci, vol. 32, pp. 1100-1108; Oct. 2010 (author manuscript; 19 pgs.).
Fuentes et al.; Spinal cord stimulation restores locomotion in animal models of Parkinson's disease; Science; 323; pp. 1578-1582; Mar. 2009.
Gallego et al.; A neuroprosthesis for tremor management through the control of muscle co-contraction; Journal of Neuroengineering and Rehabilitation; vol. 10; 36; (13 pgs); Apr. 2013.
Gallego et al; A soft wearable robot for tremor assessment and suppression; 2011 IEEE International Conference on Robotics and Automation; Shanghai International Conference Center; pp. 2249-2254; May 9-13, 2011.
Gallego et al.; Real-time estimation of pathological tremor parameters from gyroscope data.; Sensors; 10(3); pp. 2129-2149; Mar. 2010.
Gao; Analysis of amplitude and frequency variations of essential and Parkinsonian tremors; Medical & Biological Engineering & Computing; 42(3); pp. 345-349; May 2004.
Garcia et al.; Modulation of brainstem activity and connectivity by respiratory-gated auricular vagal afferent nerve stimulation in migraine patients; PAIN; International Association for the Study of Pain; 2017.
Garcia-Rill, E., et al. "Arousal, motor control, and Parkinson's disease." Translational neuroscience 6.1 pp. 198-207 (2015).
Giuffridda et al.; Clinically deployable Kinesia technology for automated tremor assessment.; Movement Disorders; 24(5); pp. 723-730; Apr. 2009.
Gracanin et al.; Optimal stimulus parameters for minimum pain in the chronic stimulatin of innervated muscle; Archives of Physical Medicine and Rehabilitation; 56(6); pp. 243-249; Jun. 1975.
Haeri et al.; Modeling the Parkinson's tremor and its treatments; Journal of Theoretical Biology; 236(3); pp. 311-322; Oct. 2005.
Halon En et al.; Contribution of cutaneous and muscle afferent fibres to cortical SEPs following median and radial nerve stimulation in man; Electroenceph. Clin. Neurophysiol.; 71(5); pp. 331-335; Sep.-Oct. 1988.
Hao et al.; Effects of electrical stimulation of cutaneous afferents on corticospinal transmission of tremor signals in patients with Parkinson's disease; 6th International Conference on Neural Engineering; San Diego, CA; pp. 355-358; Nov. 2013.
Hauptmann et al.; External trial deep brain stimulation device for the application of desynchronizing stimulation techniques; Journal of Neural Engineering; 6; 12 pgs.; Oct. 2009.
Heller et al.; Automated setup of functional electrical stimulation for drop foot using a novel 64 channel prototype stimulator and electrode array: Results from a gait-lab based study; Medical Engineering & Physic; 35(1); pp. 74-81; Jan. 2013.
Henry Dreyfuss Associates; The Measure of Man and Woman: Human Factors in Design (Revised Edition); John Wiley & Sons, New York; pp. 10-11 and 22-25; Dec. 2001.
Hernan, Miguel, et al. "Alcohol Consumption and the Incidence of Parkinson's Disease." May 15, 2003. Annals of Neurology. Volume 54. pp. 170•175.
Hua et al.; Posture-related oscillations in human cerebellar thalamus in essential tremor are enabled by voluntary motor circuits; J Neurophysiol; 93(1); pp. 117-127; Jan. 2005.
Huang, et al.; Theta burst stimulation report of the human motor cortex; Neuron, vol. 45, 201-206, Jan. 20, 2005.
Hubeaux, Katelyne, et al. "Autonomic nervous system activity during bladder filling assessed by heart rate variability analysis in women with idiopathic overactive bladder syndrome or stress urinary incontinence." The Journal of urology 178.6 (2007): 2483-2487.
Hubeaux, Katelyne, et al. "Evidence for autonomic nervous system dysfunction in females with idiopathic overactive bladder syndrome." Neurourology and urodynamics 30.8 (2011): 1467-1472.
Inoue, Masahiro, Katsuaki Suganuma, and Hiroshi Ishiguro. "Stretchable human interface using a conductive silicone elastomer containing silver fillers." Consumer Electronics, 2009. ISCE'09. IEEE 13th International Symposium on. IEEE, 2009.
Jacks et al.; Instability in human forearm movements studied with feed-back-controlled electrical stimulation of muscles; Journal of Physiology; 402; pp. 443-461; Aug. 1988.
Jobges et al.; Vibratory proprioceptive stimulation affects Parkinsonian tremor; Parkinsonism & Related Disorders; 8(3); pp. 171-176; Jan. 2002.
Joundi et al.; Rapid tremor frequency assessment with the iPhone accelerometer.; Parkinsonism & Related Disorders; 17(4); pp. 288-290; May 2011.
Kim et al.: Adaptive control of movement for neuromuscular stimulation-assisted therapy in a rodent model; IEEE Trans on Biomedical Engineering,; 56(2); pp. 452-461; Feb. 2009.
Krauss et al.; Chronic spinal cord stimulation in medically intractable orthostatic tremor; J Neurol Neurosurg Psychiatry; 77(9); pp. 1013-1016; Sep. 2006.
Kuhn et al.; Array electrode design for transcutaneous electrical stimulation a simulation study; Medical Engineering & Physics; 31 (8); pp. 945-951; Oct. 2009.
Kuhn et al.; The Influence of Electrode Size on Selectivity and Comfort in Transcutaneous Electrical Stimulation of the Forearm; Neural Systems and Rehabilitation Engineering, IEEE Transactions on; 18(3); pp. 255-262; Jun. 2010.
Kunz, Patrik, et al. "5 kHz transcranial alternating current stimulation: lack of cortical excitability changes when grouped in a theta burst pattern." Frontiers in Human Neuroscience 10 (2016): 683.
Lagerquist et al.: Influence of stimulus pulse width on M-waves, H-reflexes, and torque during tetanic low-intensity neuromuscular stimulation, Muscle & Nerve, 42(6), pp. 886-893; Dec. 2010.
Laroy et al.; The sensory innervation pattern of the fingers; J. Neurol.; 245 (5); pp. 294-298; May 1998.
Lee et al.; Resetting of tremor by mechanical perturbations: A comparison of essential tremor and parkinsonian tremor; Annals of Nuerology; 10(6); pp. 523-531; Dec. 1981.
Legon et al.; Pulsed ultrasound differentially stimulates somatosensory circuits in humans as indicated by EEG and fMRI; PLoS One; 7(12); e51177; 14 pgs.; Dec. 2012.
Liao, Wen ☐Chien, et al. "A noninvasive evaluation of autonomic nervous system dysfunction in women with an overactive bladder." International Journal of Gynecology & Obstetrics 110.1 (2010): 12-17.
Lourenco et al.; Effects produced in human arm and forearm motoneurones after electrical stimulation of ulnar and median nerves at wrist level; Experimental Brain Research; 178(2); pp. 267-284; Apr. 2007.
Malek et al.; The utility of electromyography and mechanomyography for assessing neuromuscular function: a noninvasive approach; Phys Med Rehabil in N Am; 23(1); pp. 23-32; Feb. 2012.
Mamorita et al.; Development of a system for measurement and analysis of tremor using a three-axis accelerometer; Methods Inf Med; 48(6); pp. 589-594; epub Nov. 2009.
Maneski et al.; Electrical Stimulation for suppression of pathological tremor; Med Biol Eng Comput; 49(10); pp. 1187-1193; Oct. 2011.
Marsden et al.; Coherence between cerebellar thalamus, cortex and muscle in man; Brain; 123; pp. 1459-1470; Jul. 2000.
Marshall, Ryan, et al. "Bioelectrical stimulation for the reduction of inflammation in inflammatory bowel disease." Clinical Medicine Insights: Gastroenterology 8 (2015): CGast-S31779.
McAuley et al.; Physiological and pathological tremors and rhythmic central motor control; Brain; 123(Pt 8); pp. 1545-1567; Aug. 2000.

(56) References Cited

OTHER PUBLICATIONS

McIntyre et al.; Finite element analysis of current-density and electric field generated by metal microelectrodes; Annals of Biomedical Engineering; 29(3); pp. 227-235; Mar. 2001.
Meekins et al.; American Association of Neuromuscular & Electrodiagnostic Medicine evidenced-based review: use of surface electromyography in the diagnosis and study of neuromuscular disorders; Muscle Nerve 38(4); pp. 1219-1224; Oct. 2008.
Mehnert, Ulrich, et al. "Heart rate variability: an objective measure of autonomic activity and bladder sensations during urodynamics." Neurourology and urodynamics 28.4 (2009): 313-319.
Miguel et al.; Alcohol consumption and the incidence of Parkinson's disease; Ann. Neurol.; 54(2); pp. 170-175; May 15, 2003.
Miller et al.; Multiplexed microneedle-based biosensor array for characterization of metabolic acidosis; Talanta; 88; pp. 739-742; Jan. 2012 (author manuscript; 13 pgs.).
Miller et al.; Neurostimulation in the treatment of primary headaches; Pract Neurol; Apr. 11, 2016;16:pp. 362-375.
Milne et al.; Habituation to repeated in painful and non-painful cutaneous stimuli: A quantitative psychophysical study; Experimental Brain Research; 87(2); pp. 438-444; Nov. 1991.
Mommaerts et al.; Excitation and nerve conduction; in Comprehensive Human Physiology; Springer Berlin Heidelberg; Chap. 13; pp. 283-294; Mar. 1996.
Mones et al.; The response of the tremor of patients with Parkinsonism to peripheral nerve stimulation; J Neurology, Neurosurgery, and Psychiatry; 32(6); pp. 512-518; Dec. 1969.
Morgante et al.: How many parkinsonian patients are suitable candidates for deep brain stimulation of subthalamic nucleus?; Results of a Questionnaire, Partkinsonism Relat Disord; 13; pp. 528-531; Dec. 2007.
Munhoz et al; Acute effect of transcutaneous electrical nerve stimulation on tremor; Movement Disorders; 18(2); pp. 191-194; Feb. 2003.
Nardone et al.; Influences of transcutaneous electrical stimulation of cutaneous and mixed nerves on subcortical somatosensory evoked potentials; Electroenceph. Clin. Neurophysiol.; 74(1); pp. 24-35; Jan.-Feb. 1989.
Nonis et al.; Evidence of activation of vagal afferents by non-invasive vagus nerve stimulation: An electrophysiological study in healthy volunteers; Cephalalgia; pp. 1285-1293; vol. 37(13); Mar. 28, 2017.
Japan Office Action dated Mar. 19, 2019 in Japanese Application No. 2016-570786 in 17 pages.
PCT Search Report and Written Opinion in PCT Application No. PCT/US2015/033809 dated Apr. 10, 2014 in 15 pages.
Perez et al.; Patterned Sensory Stimulation Induces Plasticity in Reciprocal Ia Inhibition in Humans; The Journal of Neuroscience; 23(6); pp. 2014-2018; Mar. 2003.
Perlmutter et al.; Deep brain stimulation; Ann Rev Neurosci; 29; pp. 229-257; Jul. 2006.
Popović Bijelić, Ana, et al. "Multi field surface electrode for selective electrical stimulation." Artificial organs 29.6 (2005): 448-452.
Popovi Maneski et al.; Electrical stimulation for the suppression of pathological tremor; Medical & Biological Engineering & Computing; 49(10); pp. 1187-1193; Oct. 2011.
Prochazka et al.; Attenuation of pathological tremors by functional electrical stimulation I: Method; Annals of Biomedical Engineering; 20(2); pp. 205-224; Feb. 1992.
Pulliam et al.; Continuous in-home monitoring of essential tremor; Parkinsonism Relat Disord; 20(1); pp. 37-40; Jan. 2014.
Quattrini et al.; Understanding the impact of painful diabetic neuropathy; Diabetes/Metabolism Research and Reviews; 19, Suppl. 1; pp. S2-8; Jan.-Feb. 2003.
Rocon et al.; Design and validation of a rehabilitation robotic exoskeleton for tremor assessment and suppression; IEEE Trans Neural Sys and Rehab Eng.; 15(3); pp. 367-378; Sep. 2007.
Silverstone et al.; Non-Invasive Neurostimulation In The Control of Familial Essential Tremor Using The Synaptic Neuromodulator; Conference Proceedings, International Functional Electrical Stimulation Society (IFES); Ed. Paul Meadows; 3 pgs.; May 1999.
Singer et al.; The effect of EMG triggered electrical stimulation plus task practice on arm function in chronic stroke patients with moderate-severe arm deficits; Restor Neurol Neurosci; 31(6); pp. 681-691; Oct. 2013.
Straube et al.; Treatment of chronic migraine with transcutaneous stimulation of the auricular branch of the vagal nerve (auricular t-VNS): a randomized, monocentric clinical trial; The Journal of Headache and Pain (2015) 16:63.
Takanashi et al.; A functional MRI study of somatotopic representation of somatosensory stimulation in the cerebellum; Neuroradiology; 45(3); pp. 149-152; Mar. 2003.
Tass et al.; Coordinated reset has sustained aftereffects in Parkinsonian monkeys; Ann Neurol; 72(5); pp. 816-820; Nov. 2012.
Tass et al.; Counteracting tinnitus by acoustic coordinated reset neuromodulation; Restorative neurology and Neuroscience; 30(2); pp. 137-159; Apr. 2012.
Tass; A Model of desynchronizing deep brain stimulation with a demand-controlled coordinated reset of neural subpopulations; Bioi Cybern; 89(2); pp. 81-88; Aug. 2003.
Thomas et al.; A review of posterior tibial nerve stimulation for faecal incontinence; Colorectal Disease; 2012 The Association of Coloproctology of Great Britain and Ireland. 15, pp. 519-526; Jun. 25, 2012.
Toloso et al.; Essential tremor: treatment with propranolol; Neurology; 25(11); pp. 1041; Nov. 1975.
Tracey; The inflammatory reflex; NATURE; vol. 420; pp. 853-859; Dec. 19/26, 2002.
Treager; Interpretation of skin impedance measurements; Nature; 205; pp. 600-601; Feb. 1965.
Valente; Novel methods and circuits for field shaping in deep brain stimulation; Doctoral thesis, UCL (University College London); 222 pgs.; 2011.
Vitton et al.; Transcutaneous posterior tibial nerve stimulation for fecalIncontinence in inflammatory bowel disease patients: a therapeutic option?; Inflamm Bowel Dis; vol. 15, No. 3, Mar. 2009; pp. 402-405.
Von Lewinski et al.; Efficacy of EMG-triggered electrical arm stimulation in chronic hemiparetic stroke patients; Restor Neurol Neurosci; 27(3); pp. 189-197; Jun. 2009.
Wardman et al.; Subcortical, and cerebellar activation evoked by selective stimulation of muscle and cataneous afferents: an fMRI study; Physiol. Rep.; 2(4); pp. 1-16; Apr. 2014.
Wiestler et al.; Integration of sensory and motor representations of single fingers in the human; J. Neurophysiol.; 105(6); pp. 3042-3053; Jun. 2011.
Woldag et al.; Evidence-based physiotherapeutic concepts for improving arm and hand function in stroke patients R A review; J Neurol; 249(5); pp. 518-528; May 2002.
Woolf et al.; Peripheral nerve injury triggers central sprouting of myelinated afferents; Nature; 355(6355); pp. 75-78; Jan. 1992.
Yarnitsky et al.; Nonpainful remote electrical stimulation alleviates episodic migraine pain; Neurology 88; pp. 1250-1255; Mar. 28, 2017.
Yeh, Kuei-Lin, Po-Yu Fong, and Ying-Zu Huang. "Intensity sensitive modulation effect of theta burst form of median nerve stimulation on the monosynaptic spinal reflex." Neural plasticity 2015 (2015) in 8 pages.
Yilmaz, Ozlem O., et al. "Efficacy of EMG-biofeedback in knee osteoarthritis." Rheumatology international 30.7 (2010): 887-892.
Zhang et al.; Neural oscillator based control for pathological tremor suppression via functional electrical stimulation; Control Engineering Practice; 19(1); pp. 74-88; Jan. 2011.
Zorba et al.; Overactive bladder and the pons; Rize University, Medical Faculty, Department of Urology; 123-124; Undated.
Zwarts et al.; Multichannel surface EMG: basic aspects and clinical utility; Muscle Nerve; 28(1); pp. 1-17; Jul. 2003.

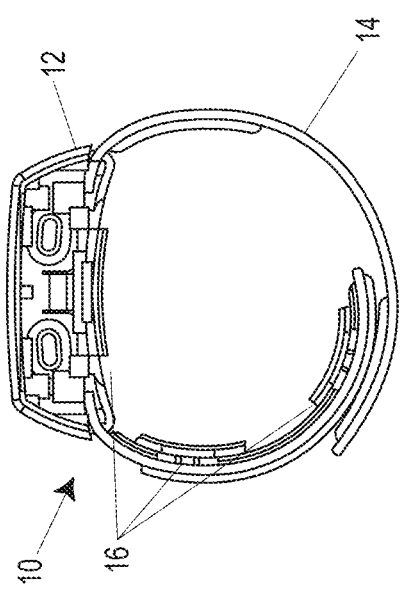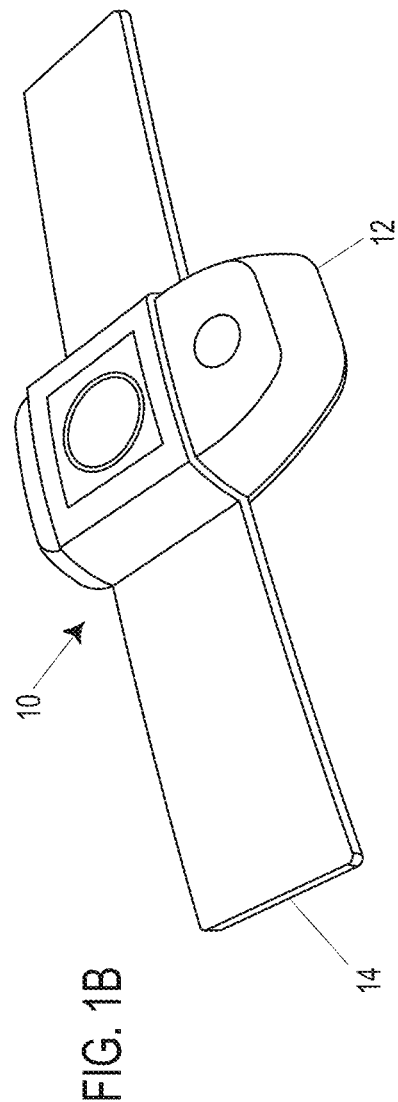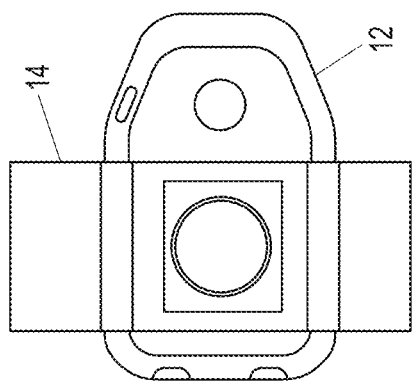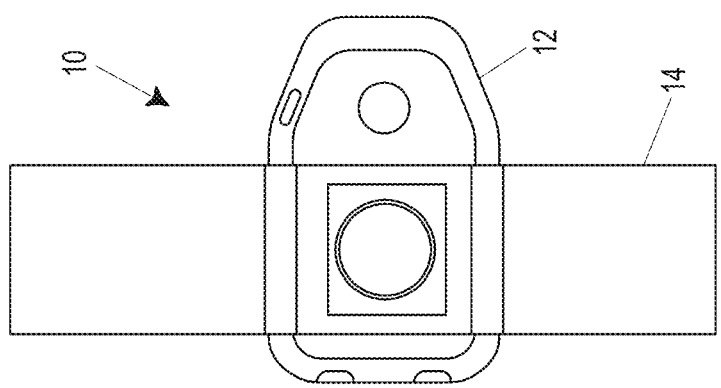

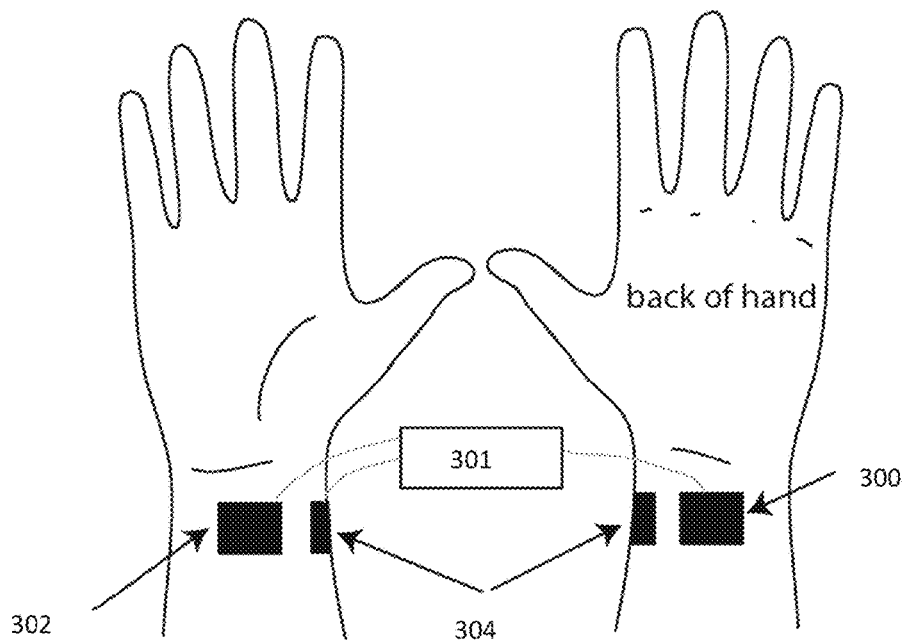
FIG. 3A
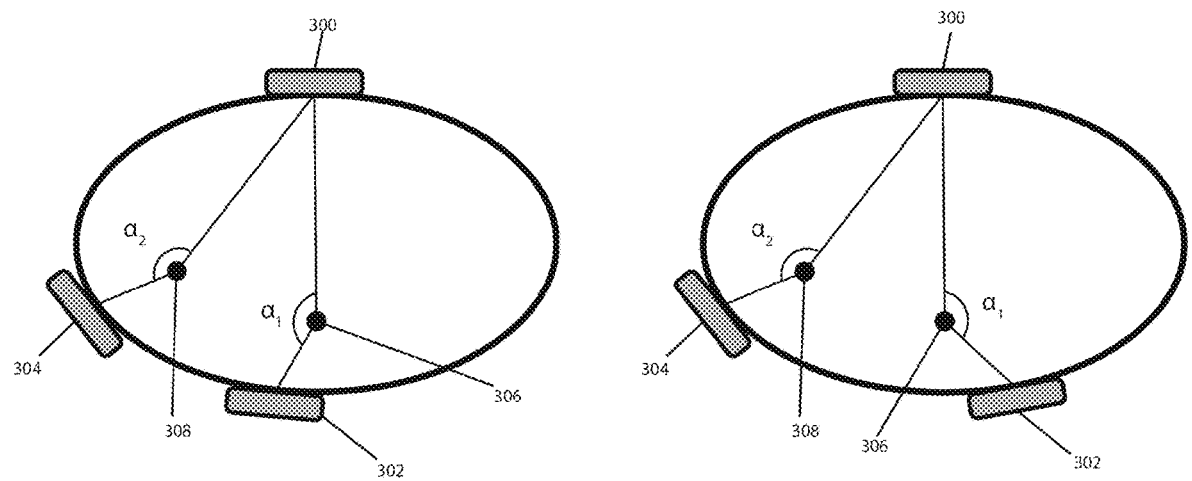
FIG. 3B
FIG. 3C

TREMOR PHASE FEEDBACK

TREMOR AMPLITUDE FEEDBACK

TREMOR FREQUENCY FEEDBACK

PREDICTIVE ADAPTATION

METHODS FOR PERIPHERAL NERVE STIMULATION

CROSS REFERENCE TO RELATED APPLICATIONS

This application is a continuation of U.S. patent application Ser. No. 16/242,983 filed on Jan. 8, 2019 and issued as U.S. Pat. No. 10,549,093, which is a continuation of U.S. patent application Ser. No. 15/721,480 filed on Sep. 29, 2017 and issued as U.S. Pat. No. 10,173,060, which is a divisional of U.S. patent application Ser. No. 15/354,943 filed on Nov. 17, 2016 and issued as U.S. Pat. No. 9,802,041, which is in turn a continuation of International Patent Application No. PCT/US2015/033809, filed Jun. 2, 2015, titled "SYSTEMS AND METHODS FOR PERIPHERAL NERVE STIMULATION TO TREAT TREMOR," now International Publication No. WO 2015/187712, which claims priority to U.S. Provisional Application No. 62/006,565, filed Jun. 2, 2014, U.S. Provisional Application No. 62/006,555, filed Jun. 2, 2014, U.S. Provisional Application No. 62/083,424, filed Nov. 24, 2014, and U.S. Provisional Application No. 62/157,116, filed May 5, 2015, each of the foregoing of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the invention relate generally to systems, devices, and methods for treating tremor, and more specifically relate to system, devices, and methods for treating tremor by stimulation of peripheral nerve(s).

BACKGROUND

Hand tremors are one of the most common movement disorders, affecting an estimated 10 million people in the U.S., with growing numbers due to the aging population. The prevalence increases with age, increasing from 5-10% of the population over 65, to above 20% over 95. Essential tremor is characterized by oscillatory movement, for example between 4-12 Hz, affecting distal limbs, like the hands. Unlike Parkinson's tremor, which exists at rest, essential tremor affects postural and kinetic activities, meaning tremor is invoked by holding a limb against gravity or during intentional movement, respectively. Tremor is also a significant problem for patients with other diseases, such as orthostatic tremor, multiple sclerosis and Parkinson's Disease. Treatment options for these conditions are limited, have undesirable side effects, or have high risk relative to the potential benefits, so alternative treatment is warranted. A number of conditions, such as tremors, can be treated through some form of transcutaneous peripheral nerve stimulation.

Designing a device to accomplish such a treatment is challenging. One difficulty in designing a product for patients with tremors is creating a device that is easy to position and configure for individuals whose hands are unsteady. People have a wide variation in wrist diameters, nerve locations, nerve depolarization characteristics, and skin conduction that leads to challenges in designing a device to comfortably, safely, and reliably target peripheral nerves for stimulation across a broad population. For instance, in a wrist-worn device targeting the median, ulnar, and radial nerves at the wrist, the band circumference for the adult population would have to vary from 13.5-19.8 cm to accommodate 5th percentile female to 95th percentile male. See Henry Dreyfus Associates, "The Measure of Man and Woman", Wiley, 2001. In addition to differences in size, there are variations in the location, depth, and branching of nerves. Thus, a system and method that can reliably stimulate one or more nerves in the wrist across a wide range of wrist sizes would be advantageous in treating hand tremors.

A second challenge to designing such a device is that tremors vary between different people. Even within the same person tremor can occur at variable times throughout the day, depending on multiple factors, including but not limited to the patient's stress level, fatigue, and diet. Thus, individually customized and responsive therapy capable of treating the tremor when it occurs or is likely to occur can provide a more effective, yet power efficient device.

SUMMARY OF THE DISCLOSURE

The present invention relates generally to systems, devices, and methods for treating tremor, and more specifically relate to system, devices, and methods for treating tremor by stimulation of peripheral nerve(s). It should be understood that some of the features described in connection with one embodiment may be combined with another embodiment.

In some embodiments, a system for treating a patient suffering from tremor is provided. The system can include a pulse generator; and a circumferential band adapted to be secured to the patient's arm or wrist, the band supporting a first and a second electrode in electrical communication with the pulse generator, the first and second electrodes being spaced on the band so as to deliver electrical stimuli from the pulse generator to the patient to preferentially excite a first nerve selected from the patient's median, radial or ulnar nerve, the first and second electrodes being arranged and configured such that in a transverse cross-sectional plane of the arm or wrist there is a 90 degree to 180 degree angle between a line connecting the first nerve and the first electrode and a line connecting the first nerve and the second electrode.

In some embodiments, the band supports a third electrode in electrical communication with the pulse generator, the first and third electrodes being spaced on the band so as to deliver electrical stimuli from the pulse generator to the patient to preferentially excite a second nerve selected from the patient's median, radial or ulnar nerve, the first and third electrodes being arranged and configured such that in a transverse cross-sectional plane of the arm or wrist there is a 90 degree to 180 degree angle between a line connecting the second nerve and the first electrode and a line connecting the second nerve and the third electrode, where the first nerve and the second nerve are different nerves.

In some embodiments, when the circumferential band is secured around the patient's arm or wrist, the first electrode is positioned on a dorsal side of the patient's arm or wrist, the second electrode is positioned on the ventral side of the patient's arm or wrist, and the third electrode is positioned on the patient's arm or wrist in between the first electrode and second electrode.

In some embodiments, the electrodes each have a center and the electrode centers are spaced about 5 mm to one quarter the circumference of the wrist or arm apart.

In some embodiments, the band comprises flexible circuitry, and the band is fastened to the housing through a riveted connector that also provides electrical communication between the flexible circuitry of the band and the pulse generator.

In some embodiments, the housing has a distal end configured to be oriented towards the patient's hand, and a proximal end configured to be oriented away from the patient's hand, such that the band, the first electrode, and the second electrode are closer to the distal end of the housing than to the proximal end of the housing.

In some embodiments, the pulse generator is the only pulse generator, and the system further includes a switch matrix configured to switch the pulse generator between at least one pair of electrodes.

In some embodiments, the switch matrix comprises a single high voltage source and ground.

In some embodiments, each electrode in the switch matrix is associated with its own set of protection circuitry.

In some embodiments, the system further includes a controller configured to deliver an alternating stimulation pattern from the pulse generator to the electrodes.

In some embodiments, the stimulation pattern includes an application of a plurality of alternating bursts of electrical stimulation delivered in a first pulse train to a first nerve selected from the patient's median, radial or ulnar nerve, and a second pulse train delivered to a different nerve selected from the patient's median, radial or ulnar nerve, wherein the first pulse train and the second pulse train are offset by about one half the tremor period.

In some embodiments, the stimulation pattern includes an application of a plurality of bursts of electrical stimulation, such that each burst includes a stimulation frequency between about 50 Hz and 2,000 Hz, and a pulse width between about 50 microsecond and 1 millisecond, and a pulse shape selected from the group consisting of monophasic rectangular, biphasic asymmetric rectangular, or biphasic symmetric rectangular.

In some embodiments, the stimulation pattern includes an application of a plurality of alternating bursts of electrical stimulation, such that each burst comprises a duration of about one half the tremor period.

In some embodiments, the system further includes a motion sensor configured to measure motion of the patient's arm or wrist.

In some embodiments, the motion sensor includes a 3-axis gyroscope or accelerometer.

In some embodiments, the system further includes a controller in communication with the pulse generator and the motion sensor, the controller programmed to determine one or more characteristics of the tremor based on a signal generated by the motion sensor.

In some embodiments, the one or more characteristics of the tremor is selected from the group consisting of the tremor frequency, the tremor amplitude, and the tremor phase.

In some embodiments, the controller is further programmed to adjust one or more parameters of the electrical stimuli based on the determined characteristics of the tremor.

In some embodiments, the first electrode, second electrode, and third electrode are fabricated on a disposable and replaceable flexible substrate with one or more electrical connectors for electrical communication with the pulse generator.

In some embodiments, each electrode further includes a pull tab to aid in fastening and removal.

In some embodiments, the housing and/or bands comprise a plurality of electrical snaps for removably receiving the first electrode, second electrode, and third electrode.

In some embodiments, the first electrode, second electrode, and third electrode are disposed on a thin liner with a spacing that corresponds to the position of the plurality of electrical snaps on the housing and/or band.

In some embodiments, the system further includes an adhesive disposed on the thin liner around the electrodes.

In some embodiments, the system further includes a cradle that securely supports the housing and the hands such that the first electrode, second electrode, and third electrode can be attached to the housing and/or band.

In some embodiments, the cradle has a cavity for securely receiving the housing such that the base of the housing is exposed.

In some embodiments, the first electrode, second electrode, and third electrode are recessed into the housing or band such that the electrodes extend a predetermined distance from the housing or hand.

In some embodiments, the first electrode and second electrode are disposable and replaceable.

In some embodiments, the hand includes moldable indentations configured to encompass the electrodes and protect them from dehydration.

In some embodiments, the first electrode and the second electrode are coated with an electrically conductive hydrogel.

In some embodiments, the first electrode and the second electrode are connected with a foam backing layer.

In some embodiments, the foam backing layer includes a serpentine shaped portion between the electrodes.

In some embodiments, the housing includes one or more depressible user input buttons, each button located on a side of the housing, and a broad bracing surface on the opposite side of the housing from each button.

In some embodiments, the housing has a skin contact side with a curved surface that follows the curvature of the patient's arm or wrist.

In some embodiments, the system further includes a rechargeable battery and an inductive coil configured to receive power from an external source to inductively charge the battery. The rechargeable battery and inductive coil can be enclosed in the housing.

In some embodiments, the electrodes have a diameter or width between about 5 mm and one-quarter the circumference of the arm or wrist.

In some embodiments, the system has only three electrodes. In other embodiments, the system only has two electrodes.

In some embodiments, the polarity of the electrodes connected to the stimulator is switchable.

In some embodiments, a method of treating a patient suffering from tremor is provided. The method can include placing a band comprising a first electrode and a second electrode around the patient's arm or wrist in a configuration such that in the transverse cross-sectional plane of the arm or wrist there is a 90 degree to 180 degree angle between a line extending between a first nerve and the first electrode and a line extending between the first nerve and the second electrode, the first nerve selected from the patient's median, radial and ulnar nerves, wherein the first and second electrodes are spaced a predetermined distance apart; and delivering a first electrical stimulus from the electrodes to excite the first nerve to reduce the patient's tremor.

In some embodiments, the band includes a third electrode spaced a predetermined distance apart from the first and second electrodes such that there is a 90 degree to 180 degree angle between a line extending between a second nerve and the first electrode and a line extending between the second nerve and the third electrode, the second nerve selected from the patient's median, radial and ulnar nerves.

In some embodiments, the method further includes delivering a second electrical stimulus from the first electrode and the third electrode to excite the second nerve.

In some embodiments, first nerve is the median nerve and the second nerve is the radial nerve.

In some embodiments, the band is operatively connected to a housing enclosing a motion sensor, and the method further includes measuring one or more characteristics of the tremor with the motion sensor while the patient performs a tremor-invoking task.

In some embodiments, the tremor-invoking task is an instructed task or a kinetic activity.

In some embodiments, the instructed task is a postural hold and the kinetic activity is drawing or writing.

In some embodiments, the tremor-invoking task is a task the patient performs uninstructed as part of normal daily activities.

In some embodiments, the measured characteristics of the tremor include a frequency spectrum of the tremor.

In some embodiments, the method further includes determining a tremor frequency by determining a center frequency peak within a 4 to 12 Hz range in the frequency spectrum of the tremor.

In some embodiments, the measured characteristics of the tremor include an amplitude of the tremor.

In some embodiments, the method further includes temporally offsetting the first electrical stimulus from the second electrical stimulus by a period of time based on a period of the tremor.

In some embodiments, the period of time is a function of the period of the tremor divided by the number of nerves that are stimulated.

In some embodiments, the number of nerves that are stimulated is two.

In some embodiments, the first electrode is in electrical communication to a first contact of a stimulator and the second electrode is in electrical communication to a second contact of the stimulator, the stimulator configured to generate an electrical pulse between of the first electrode and the second electrode, the electrical pulse having a polarity.

In some embodiments, the method further comprises switching the first contact and the second contact of the stimulator such that the first electrode is in electrical communication with the second contact and the second electrode is in electrical communication with the first contact in order to change the polarity of the electrical pulse so that the first electrical stimulus is biphasic.

In some embodiments, the method further includes measuring motion of the patient; determining the energy, amplitude, frequency, and pattern of the measured motion; and separating non-tremor motion from tremor motion based in part on the determined energy, amplitude, frequency, and pattern of the measured motion.

In some embodiments, the method further includes determining a stimulation sensation threshold and a muscle contraction or discomfort threshold.

In some embodiments, the method further includes increasing an amplitude of the first electrical stimulus from the stimulation sensation threshold towards the muscle contraction or discomfort threshold.

In some embodiments, the step of increasing the amplitude of the first electrical stimulus includes increasing the amplitude linearly or exponentially.

In some embodiments, the step of increasing the amplitude of the first electrical stimulus includes increasing the amplitude in a series of progressively greater peak amplitudes separated by reductions in amplitude.

In some embodiments, the step of increasing the amplitude of the first electrical stimulus includes increasing the amplitude to a value greater than the muscle contraction or discomfort threshold and then reducing the amplitude to below the muscle contraction or discomfort threshold.

In some embodiments, the step of increasing the amplitude of the first electrical stimulus includes increasing the amplitude in a series of stepwise increments, where each increment in amplitude is held for a predetermined duration.

In some embodiments, each stepwise increment in amplitude is followed by a decrease in amplitude that is smaller in magnitude than the increase in each stepwise increment.

In some embodiments, the first electrical stimulus and the second electrical stimulus are delivered out of phase to the tremor.

In some embodiments, the method further includes determining the tremor frequency and phase by analyzing a signal from a motion sensor worn by the patient selected from the group consisting of an accelerometer, a gyroscope, a magnetometer, and a bend sensor.

In some embodiments, the step of using motion sensors to measure characteristics of the tremor during a tremor-invoking task and using these tremor characteristics to determine parameters of the stimulation waveform is done in real-time.

In some embodiments, the first electrical stimulus and/or the second electrical stimulus have a stochastic resonance electrical stimulation pattern.

In some embodiments, the method further includes determining an electrical stimulation level that is above a sensation threshold and below a muscle contraction threshold and the patient's pain tolerance threshold.

In some embodiments, the positioning of the band is verified by paresthesia in the patient's hand.

In some embodiments, the positioning of the band is based in part on a comparison of a shape of the housing with one or more anatomical features.

In some embodiments, the first electrical stimulus has a duration between about 20 and 60 minutes.

In some embodiments, the method further includes measuring motion of the patient's arm or wrist during a specific task; and determining characteristics of the tremor from the measured motion.

In some embodiments, the specific task is a postural, kinetic, or intentional movement.

In some embodiments, the characteristics of the tremor include tremor frequency; and the method further includes alternating a timing of burst patterns of the first electrical stimulus based on the tremor frequency.

In some embodiments, a method of treating a patient suffering from tremor is provided. The method can include determining a circumference of a patient's wrist; providing a band and housing having a predetermined circumferential spacing for a first electrode, a second electrode, and a third electrode, where the predetermined circumferential spacing is based on the determined circumference of the patient's wrist, where the housing encloses a pulse generator configured to be in electrical communication with the first electrode, the second electrode, and the third electrode, where the band and housing are configured to be positioned on the wrist such that the first electrode is positioned approximately along the midline of the dorsal side of the arm or wrist, the second electrode is positioned approximately along the midline of the ventral side of the arm or wrist, and the third electrode is positioned in between the first electrode and second electrode, where the first electrode and the second electrode form a first electrode pair and the first electrode and third electrode form a second electrode pair; stimulating a first nerve by delivering a first electrical stimulus between the first electrode pair; and stimulating a second nerve by delivering a second electrical stimulus between the second electrode pair.

In some embodiments, a method of treating a patient suffering from tremor is provided. The method can include determining a circumference of a patient's wrist; selecting a band and housing having a predetermined circumferential spacing for a first electrode, a second electrode, and a third electrode, where the predetermined circumferential spacing is based on the determined circumference of the patient's wrist, where the housing encloses a pulse generator configured to be in electrical communication with the first electrode, the second electrode, and the third electrode; positioning the band and housing on the wrist such that the first electrode is positioned approximately along the midline of the dorsal side of the arm or wrist, the second electrode is positioned approximately along the midline of the ventral side arm or wrist, and the third electrode is positioned in between the first electrode and second electrode, where the first electrode and the second electrode form a first electrode pair and the first electrode and third electrode form a second electrode pair; stimulating a first nerve by delivering a first electrical stimulus between the first electrode pair; and stimulating a second nerve by delivering a second electrical stimulus between the second electrode pair.

In some embodiments, one or more electrodes can be connected to a given stimulator lead at the same time.

In some embodiments, a device is provided. The device can include an adjustable array of electrodes configured to be adjustable to target one or more nerves of the subject; a skin interface in contact with the adjustable array of electrodes; an adjustable band in contact with the adjustable array of electrodes; and an electronics box in contact with the band.

In some embodiments, the electrodes are a linear array.

In some embodiments, the electrodes circumvent a limb of the subject.

In some embodiments, the limb is a wrist.

In some embodiments, electrodes on the dorsal side of the limb is the common electrode.

In some embodiments, electrodes on the ventral side of the limb are signal electrodes.

In some embodiments, the nerve is a nerve selected from the group consisting of: ulnar, median, and radial, or any combination thereof.

In some embodiments, the electronics is configured to switch current between electrodes in the array of electrodes.

In some embodiments, at least two electrodes in the array of electrodes are the same size.

In some embodiments, at least two electrodes in the array of electrodes are different sizes.

In some embodiments, the array of electrodes configured for the dorsal side of a limb are different sizes than the electrodes of the array configured for the ventral side of the limb.

In some embodiments, electrodes in the array of electrodes are configured to accept a maximum amount of current.

In some embodiments, an impedance value between two or more electrodes in the array of electrodes is from 20 nF to 120 nF.

In some embodiments, an impedance value between two or more electrodes in the array of electrodes is from 5 nF to 300 nF.

In some embodiments, the array of electrodes includes a material selected from the group consisting of: Ag/AgCl, Ag, Au, Stainless steel, and conductive rubber.

In some embodiments, the skin interface includes a material selected from the group consisting of: a hydrogel, a conductive fluid, a conductive gel, a conductive lotion, a fabric, or any combination thereof.

In some embodiments, the skin interface includes a hydrogel.

In some embodiments, the hydrogel has an impedance value that prevents current leakage between electrodes.

In some embodiments, an impedance value of the two or more electrodes is dependent on the spacing of the electrodes.

In some embodiments, the skin interface layer has ranges from above 1000 ohm-cm to 100 kohm-cm in volume resistivity In some embodiments, the device has some current leakage between an electrode in the array of electrodes and the skin interface.

In some embodiments, the leakage current is less than 50%.

In some embodiments, the leakage current is less than 30%.

In some embodiments, the leakage current is less than 10%.

In some embodiments, a method for fitting a subject with a tremor with a neuromodulation device is provided. The method can include contacting a limb of the subject with a device comprising an adjustable array of electrodes, configured to be adjustable to one or more nerves of the subject; determining a location of nerve response; and fitting the subject with the device based on the location of nerve response.

In some embodiments, the nerve response is paresthesia.

In some embodiments, the method of determining the nerve response includes stimulating electrodes in the array of electrodes.

In some embodiments, the location of nerve response is indicative of nerve activation.

In some embodiments, the method of determining nerve response includes contacting a different portion of the limb with a feedback device.

In some embodiments, the limb includes a wrist, and the different portion comprises a finger.

In some embodiments, the feedback device includes a measurement electrode.

In some embodiments, activation of the electrode indicates which nerve has been excited.

In some embodiments, the method of determining nerve response includes identifying positional movement of the limb.

In some embodiments, the fitting includes placing the device on the limb for activating a nerve in the limb with the device.

In some embodiments, the fitting includes selecting electrodes for activation that are necessary for the activation. In some embodiments, parameters can be stored in memory and referenced by the microcontroller in the device during treatment.

In some embodiments, the activating includes peripheral nerve stimulation.

In some embodiments, the activating treats a tremor in the subject.

Although many of the embodiments have been described having two or three electrodes, it should be understood that other embodiments may have additional electrodes, particularly if additional nerves are being target.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1E illustrate various views of an embodiment of a device and system that provides peripheral nerve stimulation, targeting individual nerves, to reduce tremor. FIG. 1E shows a schematic of a housing of the device that contains various components.

FIGS. 3A-3C illustrate various embodiments of electrodes on a wrist, including a common electrode on the back of the wrist to reduce the number of electrodes needed to stimulate multiple nerves and electrodes positioned on the circumference of the wrist to selectively stimulate the nerves targeted for excitation.

FIG. 4A illustrates that in line placement increases the size of the wrist banded needed. FIG. 4B illustrates that if the electrodes are placed along the circumference with a common electrode, the band width decreases.

DETAILED DESCRIPTION

Figure 1E:
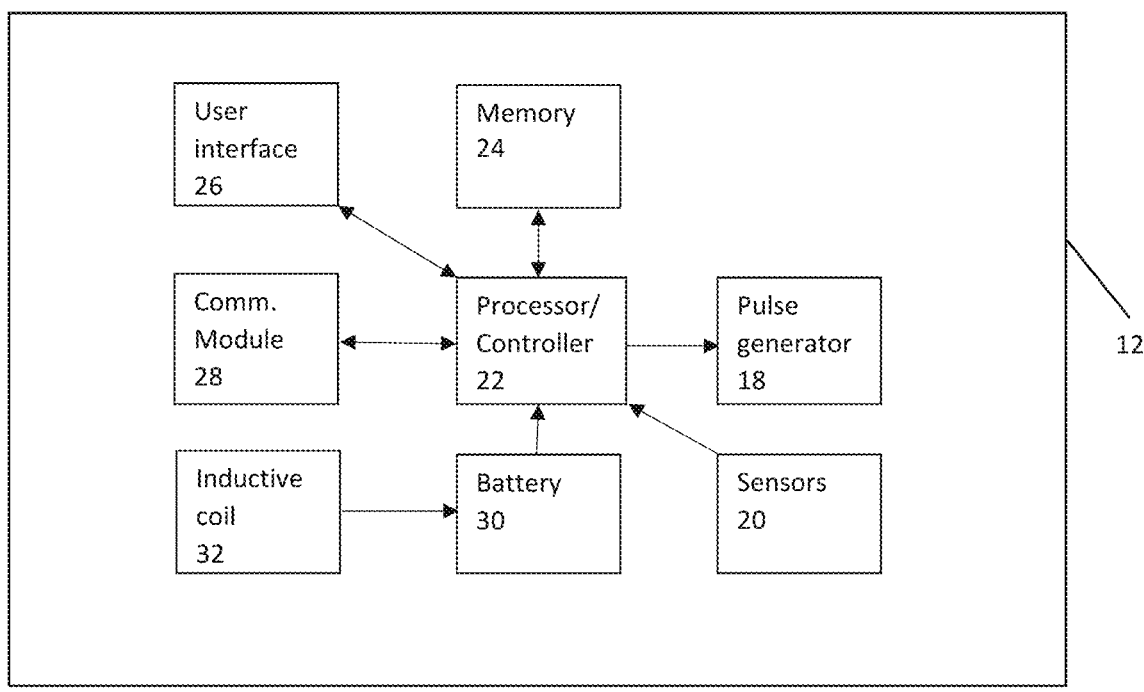

One aspect of this invention is a device and system that provides peripheral nerve stimulation, targeting individual nerves (FIG. A-1E). One aspect of this invention is a device and system 10 that allows customization and optimization of transcutaneous electrical treatment to an individual. In particular, the device 10 described is for electrical stimulation of the median, radial, or ulnar nerves in the wrist for treating tremors. Targeting those specific nerves and utilizing appropriately customized stimulation results in more effective therapy (e.g., reduced tremor).

FIGS. 1A-1E illustrate an embodiment of a device and system 10 that provides peripheral nerve stimulation, targeting individual nerves, to reduce tremor. In some embodiments, the device 10 is designed to be worn on the wrist or arm. In some embodiments, electronics located in a watch-like housing 12 measure tremor and also generate an electrical stimulation waveform. Electrical contacts in a band 14 and/or housing 12 transmit the stimulation waveform to the disposable electrodes 16. The location of the contacts in the band 12 is arranged such that specific nerves are targeted at the wrist, such as the median and radial nerves. The electronics housing 12 also can have a digital display screen to provide feedback about the stimulation and measured tremor characteristics and history to the wearer of the device.

In some embodiments, the treatment device 10 is a wristworn device consisting of 1) an array of electrodes 16 encircling the wrist, 2) a skin interface to ensure good electrical contact to the person, 3) an electronics box or housing 12 containing the stimulator or pulse generator 18, sensors 20, and other associated electronics such as a controller or processor 22 for executing instructions, memory 24 for storing instructions, a user interface 26 which can include a display and buttons, a communications module 28, a battery 30 that can be rechargeable, and optionally an inductive coil 32 for charging the battery 30, and the like, and 4) a band to hold all the components together and securely fasten the device around the wrist of an individual.

Figure 2A:
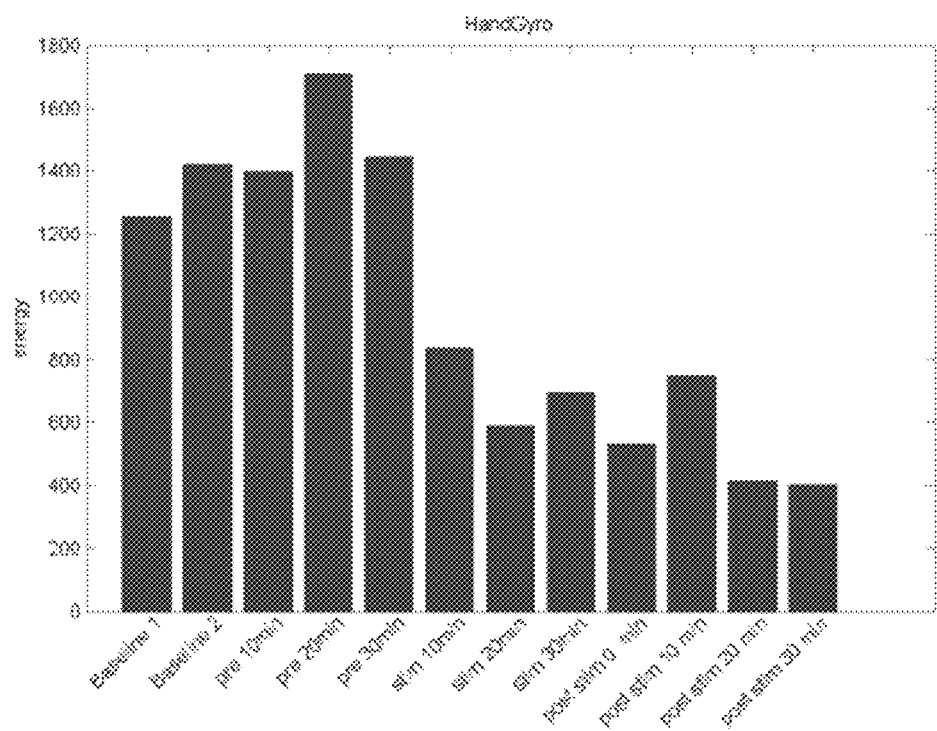
FIG. 2A illustrates a graph showing a reduction in tremor for a patient with a customized stimulation from an embodiment of the array concept.
Figure 2B:
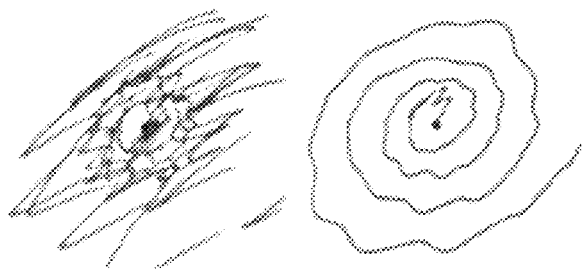
FIG. 2B demonstrates the improvement in a spiral drawn by a patient before stimulation (at left) and after stimulation (at right).

This system has shown dramatic tremor reduction after providing electrical stimulation to nerves in the patient's wrist in accordances to the embodiments described herein. FIG. 2A is an example of the tremor reduction detected using a gyroscope to measure the tremor energy during a postural hold. FIG. 2B is an example of the tremor reduction detected by having the patient draw a spiral.

Circumferential Space Electrodes

One aspect of our device is the use of only three electrodes to target two nerves (e.g., median and radial), with a shared or common electrode 300 placed on the dorsal side of the wrist (FIG. 3A). In some embodiments, the common electrode 300 can be placed approximately on the longitudinal midline of the dorsal side of the arm or wrist. In some embodiments, an additional electrode 302 can be placed approximately on the longitudinal midline of the ventral side of the arm or wrist to target the median nerve. In some embodiments, yet another electrode 304 can be placed in between the common electrode 300 and the ventrally placed electrode 302 to target the radial nerve. In some embodiments, yet another electrode can be placed to target the ulnar nerve. More generally, combining subsets of electrodes permits targeting N nerves with fewer than N electrodes.

FIGS. 3B and 3C illustrate the positions of the common electrode 300, the ventrally placed electrode 302, and the radial electrode 304 in relation to the median nerve 306 and the radial nerve 308 in a transverse cross-sectional plane of the patient's wrist or arm. The electrodes 300, 302, 304 are positioned such that in a projection into the transverse cross-sectional plane of the arm or wrist there is a 90 degree to 180 degree angle, al, between a line connecting the median nerve 306 and the center of the common electrode 300 and a line connecting the median nerve 306 and the center of the ventrally placed electrode 302, and there is a 90 degree to 180 degree angle, α2, between a line connecting the radial nerve 308 and the common electrode 300 and a line connecting the radial nerve 308 and the radial electrode 304. The angles α1 and α2 may each be in either a counter-clockwise direction (as al is shown in FIG. 3B) or in a clockwise direction (as al is shown in FIG. 3C). More generally, electrodes can be spaced apart by a predetermined distance such that when the electrodes are positioned circumferentially around a patient's wrist, one of the angles formed between each electrode pair and its target nerve is between about 90 degrees and 180 degrees. Such an orientation results in each electrode of the electrode pair being placed generally on opposite sides of the target nerve. In other words, the target nerve is positioned approximately between the electrode pair.

Figure 4A:
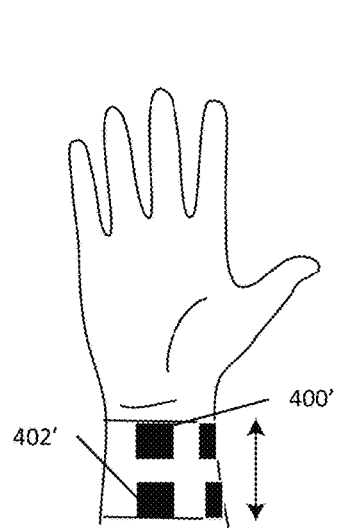
FIGS. 4A and 4B illustrate how in some embodiments the band width can vary depending on how the electrodes are arranged.
Figure 4B:
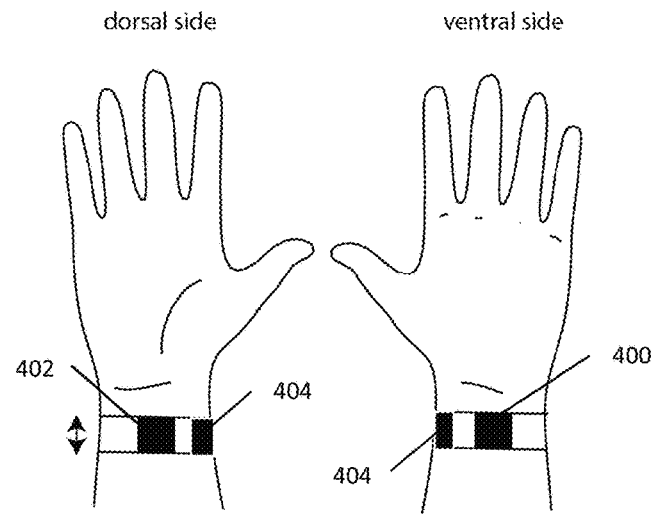

As shown in FIGS. 4A and 4B, three electrodes 400, 402, 404 placed circumferentially around the wrist allow: (1) a reduced band width compared to a typical arrangement where the two electrodes 400', 402' are longitudinally placed along the same nerve, and (2) targeting deeper into the tissue by having the pair of electrodes across from each other to target each nerve. Although the embodiments have been described with reference to three electrodes for the stimulation of two nerves, it is understood that alternative embodiments can utilize two electrodes to stimulate a single nerve, where the two electrodes can have a fixed spacing to allow the electrodes to stimulate the nerve from opposing sides of the nerve. Similarly, other embodiments can utilize more than three electrodes. For instance, an additional electrode can be added to target the ulnar nerve. In addition, different combination of electrodes can be used to target one or more nerves from the group of the median, radial, and ulnar nerves.

Mapping the nerves of a number of individuals with different wrist sizes by selectively stimulating circumferential locations on the wrist and verifying where the user feels paresthesia in order to identify the median, radial, and ulnar nerve showed the variability in nerve location relative to wrist size, as well as the high individual variable in physiology. Individual nerves can be targeted with electrodes positioned at the correct location, such as the positions shown in FIG. 3A or an array allowing selection of those individual nerves, as discussed below.

Table 1 presents data showing individuals' wrist sizes and the stimulation locations needed to excite the radial, median, and ulnar nerve. Notice that multiple locations can sometimes target the same nerve and also that indivuals of the same wrist circumference and width can often have very different responses. Zero is the centerline of each individual's wrist and numbers refer to elements to the left (negative) and to the right (positive) of the center element (0) when looking at the wrist with palm side up. All subjects in this table were right handed. U=Ulnar, M=medial, and R=Radial.

Figure 5A:
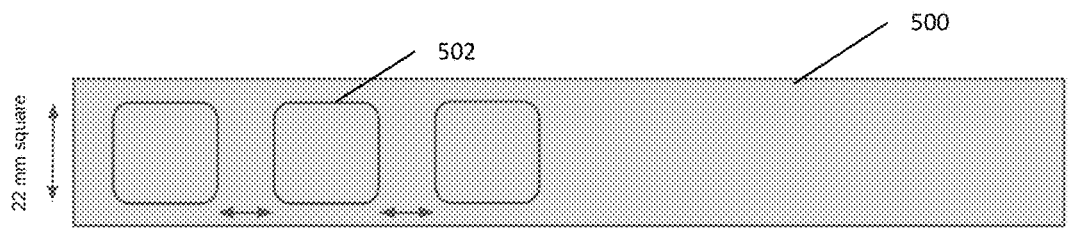
FIGS. 5A-5C illustrate various embodiments of different fixed spacings between the electrode pads that were able to successfully target predetermined nerves in patients with varying anatomy.
Figure 5B:
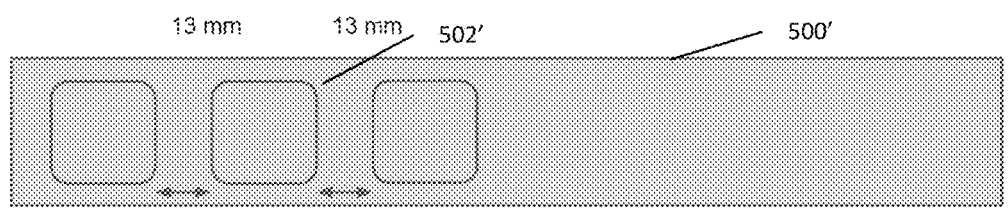
Figure 5C:
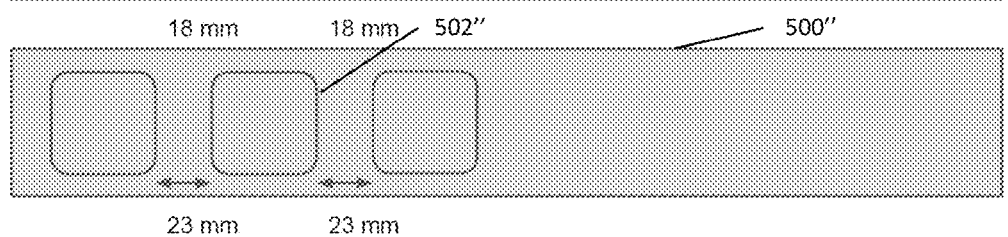

FIG. 5B illustrates an embodiment of a band 500' having three electrodes 502' spaced about 18 mm apart that can be used for wrists with a circumference between about 15.5 and 17.5 cm. FIG. 5C illustrates an embodiment of a band 500" having three electrodes 502" spaced about 23 mm apart that can be used for wrists with a circumference between about 17.5 and 19.5 cm.

Sizing of the electrode structure may be based upon a balance of patient comfort, device power consumption, and ability to target nerves. Small electrodes are advantageous because lower currents and power are needed to stimulate a nerve. However the smaller electrodes may have several disadvantages, including: (1) increased difficulty of nerve targeting, as the electrode has to be placed precisely at the right anatomical location; (2) intensified edge effects of the electrical field produced between electrodes, which reduces comfort of the patient; and (3) reduced surface area of the electrode in contact with the skin, which can cause small deviations in the electrode integrity and skin adhesion to reduce patient comfort. In contrast, larger electrodes are advantageous because they tend to be more comfortable for the patient because of the reduction of electrical field edge effects, reduction in sensitivity to small deviations in the electrodes, and reduction in sensitivity to the current amplitude step size on the stimulator device. In addition, less precise placement is needed for larger electrodes. However, a disadvantage of larger electrodes is the requirement of more current and power to achieve a specified current density.

In some embodiments, wrist circumference and nerve location are the primary anatomical factors that drive selection of electrode size. The median nerve is generally located on the centerline of the ventral side of the wrist. Therefore, as shown in FIG. 3 for example, an electrode 302, the median electrode, can be placed on the centerline of the ventral side of the wrist. To target deeper structures and minimize the width of a device, another electrode 300, the

TABLE 1

| Subject | Wrist Circ. | Wrist Width | -7 | -6 | -5 | -4 | -3 | -2 | -1 | 0 | 1 | 2 | 3 | 4 | 5 | 6 | 7 |
|---|---|---|---|---|---|---|---|---|---|---|---|---|---|---|---|---|---|
| 1 | 15.5 | 5.2 | | | | U | U | | | | M | R | R | R | | | |
| 2 | 17.6 | 6.4 | | U | | | | | | | M | | R | | | | |
| 3 | 17.5 | 5.7 | | | | U | | | | M | M | R | R | R | | | |
| 4 | 16.5 | 5.9 | | | | | U | | M | M | M | R | R | | | | |
| 5 | 18.7 | 6.6 | | | | U | U | M | M | | R | R | R | | | | |
| 6 | 15.5 | 5.2 | | | | | U | U | | M | R | R | | | | | |
| 7 | 16.3 | 5.3 | | | U | U | | | | M | | R | | | | | |
| 8 | 15.5 | 5.2 | | | | | U | U | | M | R | R | | | | | |
| 9 | 17.5 | 6.5 | | | | | U | U | | M | M | M | | R | R | | |
| 10 | 15.9 | 5.2 | | | | R | U | U | | M | M | M | R | R | | | |
| 11 | 15.2 | 5.1 | | | | | U | | M | M | R | | | | | | |
| 12 | 14.3 | 4.6 | | | | R | R | R | | M | M | U | U | | | | |

Figure 6:
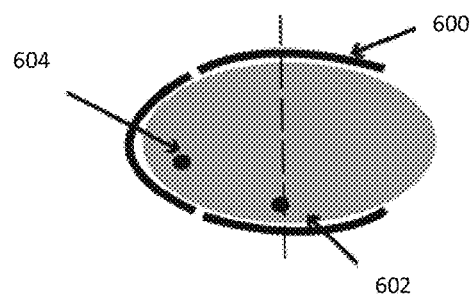
FIG. 6 illustrates a diagram showing how the maximum size of the electrodes can be calculated in some embodiments.

Some embodiments of the device have different fixed spacings between appropriately sized electrodes to target nerves in patients with varying physiology based on wrist circumference. The wrist circumference of 5th percentile female to 95th percentile male is 13.5-19.5 cm. Sizing diagrams are shown in FIGS. 5A-5C, which illustrate three band configurations using 22 mm square electrodes. FIG. 5A illustrates an embodiment of a band 500 having three electrodes 502 that are spaced about 13 mm apart that can be used for wrists with a circumference between about 13.5 cm to 15.5 cm. Since 22 mm electrodes were used, the spacing between the centers of the electrodes is 35 mm. The procedure for determining the spacing is further described below.

return electrode or common electrode, can be placed on the centerline of the opposite side, or dorsal side, of the wrist. In some embodiments, the median electrode may be offset from the centerline to be biased towards the thumb while the return electrode remains placed on the centerline of the dorsal side of the wrist. In some embodiments, the offset of the median electrode can be a predetermined distance, which is at maximum, about one-quarter of the circumference of the wrist. A third electrode, the radial electrode, can be placed in between the first and second electrode to target the radial nerve. Some embodiments can utilize more than three electrodes. For instance, an additional electrode can be added to target the ulnar nerve. In addition, different combination of electrodes can be used to target one or more nerves from the group of the median, radial, and ulnar nerves. In some embodiments, all electrodes can be the same size (i.e., area) for two reasons: (1) ease of manufacturability at large volumes, and (2) improved comfort by maintaining the same current density at any pair of electrodes. As shown in FIG. 6, these considerations may set an upper bound for the size of the electrodes 600 to stimulate the median nerve 602 and radial nerve 604 as one-quarter of the circumference of the smallest person's wrist (5th percentile female), or about 3.5 cm.

In some embodiments, the lower bound of the electrode size can be 5 mm, based on the smallest sizes found in literature of electrode arrays. Within these limits, a 22 mm by 22 mm size was chosen because it allowed a good balance between stimulator power and nerve targeting. The 22 mm size allowed a reasonable amount of misalignment for targeting the nerve (about 1 cm circumferential measured empirically), without consuming an unreasonable amount of power for a wearable device form factor. The 22 mm size is also a standard size for electrode manufacturing as it is used commercially in ECG devices. In some embodiments, the electrode size can be between 10 mm and 30 mm, or 15 mm and 25 mm, or 20 and 25 mm.

Based on electrode size and to accommodate variation in wrist size, the electrode spacing can be grouped into three sizes in some embodiments, in which each size spans a wrist circumference range of 2 cm. In each range, the middle wrist circumference in that 2 cm range was chosen and spacing of the electrodes was calculated based upon the wrist circumference. For example, in the smallest sized band, for wrist sizes 13.5 to 15.5 cm, calculations were based on a 14.5 cm wrist circumference. The center-to-center spacing of the median electrode and the return electrode on the back of the wrist should be roughly half the circumference of the wrist. Subtracting the size of the electrodes (22 mm) determines that the inter-electrode spacing should be around 13 mm.

Sizing calculations were also slightly biased such that placement of the median electrode erred towards the thumb, as this was more effective at stimulating the median nerve and would avoid stimulating the ulnar nerve, in case the electrodes were shifted or placed imprecisely. In some embodiments, ulnar nerve stimulation may be less preferable than radial nerve stimulation as it was found to cause an unpleasant sensation in early testing.

Test arrays were fabricated by affixing hydrogel electrodes to a liner at the desired distances. The common electrode was aligned to the center of the back of the wrist and the hydrogels were connected to a stimulation device. As shown in Table 2, all subjects were able to target the radial and median nerves using the appropriately selected bands. At a shift of 1 cm towards the thumb, most individuals experienced diminished median nerve excitation that could be accommodated with greater amplitude of stimulation. At a shift of 1 cm towards the pinky, many individuals gained ulnar sensation. After a large shift of about half an electrode pad size, most subjects were still able to feel the stimulation of the correct nerve, but occasionally required a greater amplitude of stimulation. These preliminary results demonstrated that the electrode spacing and size was sufficient.

TABLE 2

Data confirming that the electrode spacings successfully target the median and radial nerve of a number of individuals.

| Gender | Wrist Circumference (cm) | Hand Stimulated | Size | Radial | Median |
| --- | --- | --- | --- | --- | --- |
| M | 17.1 | R | L | Yes | Yes |
| M | 17.5 | R | L | Yes | Yes |
| M | 18.6 | R | L | Yes | Yes |
| M | 17.5 | R | L | Yes | Yes |
| M | 17.4 | L | L | Yes | Yes |
| M | 17.9 | R | M | Yes | Yes |
| F | 16.3 | R | M | Yes | Yes |
| M | 16.6 | R | M | Yes | Yes |
| M | 16.5 | R | M | Yes | Yes |
| F | 14.5 | R | S | Yes | Yes |
| F | 15.4 | R | S | Yes | Yes |
| F | 14.9 | R | S | Yes | Yes |
| F | 12.7 | R | S | Yes | Yes |
| F | 15.6 | R | S | Yes | Yes |

Figure 7A:
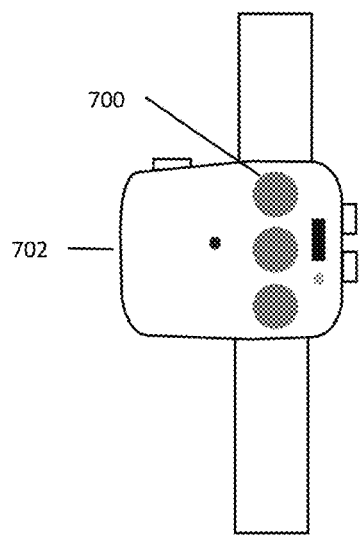
FIGS. 7A and 7B illustrate how the electrode connector can be moved out of the band and into the box to simplify the band.
Figure 7B:
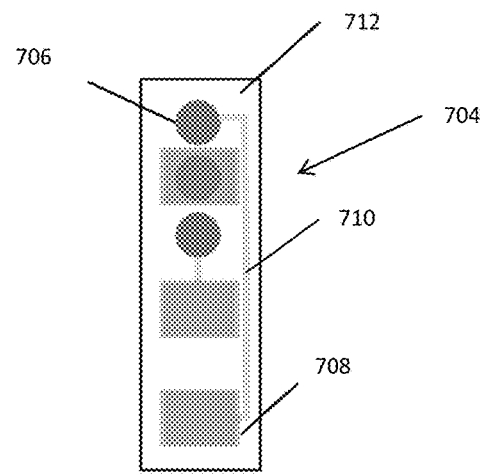

In one embodiment of the device, the electrode connections could be located on the underside of the electronics box, where one type of electrode connection could be a snap button. In FIGS. 7A and 7B, all three electrode connectors 700 are located on the underside of the electronics box 702. The connectors 700 on the electronics box 702 can interface with a flexible electrode system 704 which can have complementary connectors 706. The flexible electrode system 704 can also have three electrodes 708 that are electrically connected to the complementary connectors 706 using electrical traces 710. The components of the flexible electrode system 704 can be integrated onto a flexible liner 712. The advantage of this construction where the electrode connections are on the electronics box is that electronics are not needed in the band. The disadvantage of this construction is that the flexible traces 710 may require custom manufacturing and commensurate increased cost. Additionally, the flexible traces 710 may widen the band or contribute additional complexity and cost if constructed as a two-layer flex.

Other Electrode Array Configurations

Various types of electrode arrays can be used. In some embodiment as described above, a circumferential array of two or more electrodes, such as three electrodes, positioned circumferentially around patient's wrist or arm can be used. Other electrode array configurations can also be used, including two dimensional arrays. The electrode pairs formed in these electrode arrays can be designed such that each element is individually addressable and has limited current density. This array configuration is an improvement over conventional dual-element arrays. First, it limits current density spikes that can cause discomfort and that can increase the risk of burns with larger elements. Discomfort and burns can occur when, for example, hydrogels peel off or dry cloth electrodes have poor contact with the skin. Second, it enables selecting the optimal stimulation location for each patient's specific geometry or neurophysiology. The stimulation location may be targeted either by exciting a single set of electrodes or by steering the current using simultaneous excitation of multiple electrodes. Third, it permits shifting the stimulation location over time to reduce the overall current density applied to a certain patch of skin which can reduce skin irritation due to stimulation.

In some embodiments, an electrode array may have a defined pattern of electrical contacts arranged in a ring around the wrist. In order to stimulate electrically, current can be applied between two sets of contacts through the human skin. In this array, any number of electrodes can be connected to either set of contacts, making it very configurable. In most situations, a skin interface will need to be placed in between the electrode contacts and the person. In many cases, the mechanical and electrical properties of this skin interface coupled with the mechanical properties of the array will influence the performance and complexity of the device.

Figure 8A:
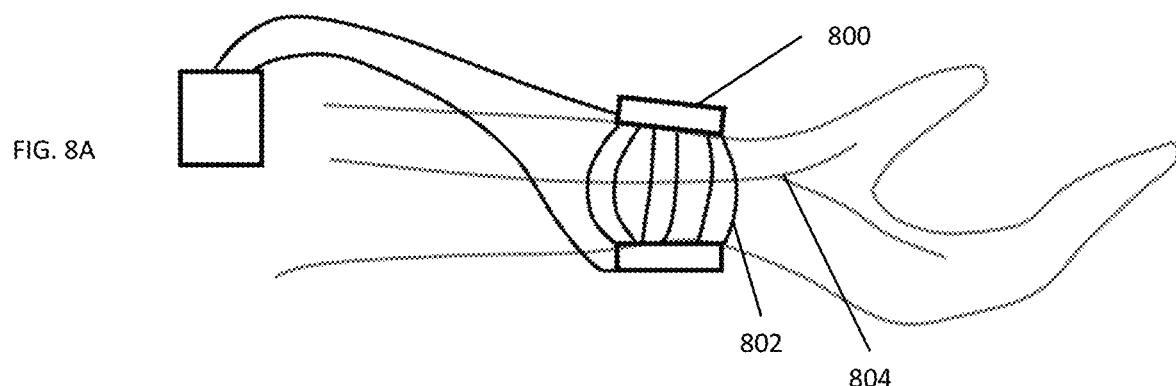
FIGS. 8A and 8B illustrate an embodiment of conventional median nerve excitation with electrodes longitudinally placed along the nerve (FIG. 8B) versus excitation by an array of electrodes circumferentially distributed around the wrist (FIG. 8A).
Figure 8B:
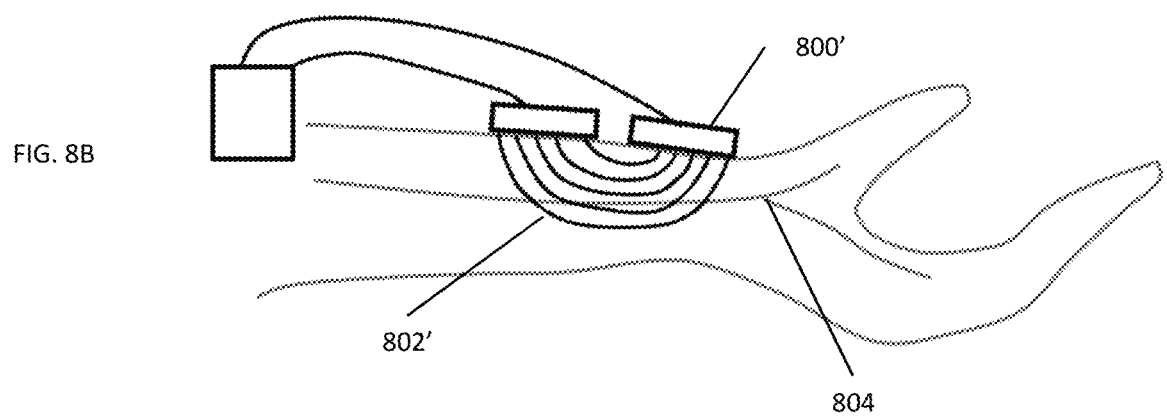

Typically for nerve excitation in the wrist, two electrodes 800' are placed longitudinally along the nerve with a reasonable spacing of at least 1 cm, as shown in FIG. 8B. The purpose of this positioning is to get the electric field 802' to penetrate into the tissue to depolarize the underlying nerve 804. With two adjacent electrodes 800', there is only a shallow penetration of the stimulating current. In contrast as shown in FIG. 8A, with electrodes 800 excited on opposite sides of the wrist, the electric field 802 extends through the wrist and this enables excitation of nerves 804 deeper in the tissue. As shown in FIGS. 4A and 4B, to achieve the same level of stimulation using longitudinally placed electrodes, would likely require a larger cuff Therefore, the circumferential array is compact and thus advantageous for wearable devices. The advantage of having the configurability of the array is that the same nerves can be reached, but in a more compact form factor than convential median nerve excitation.

Figure 9:
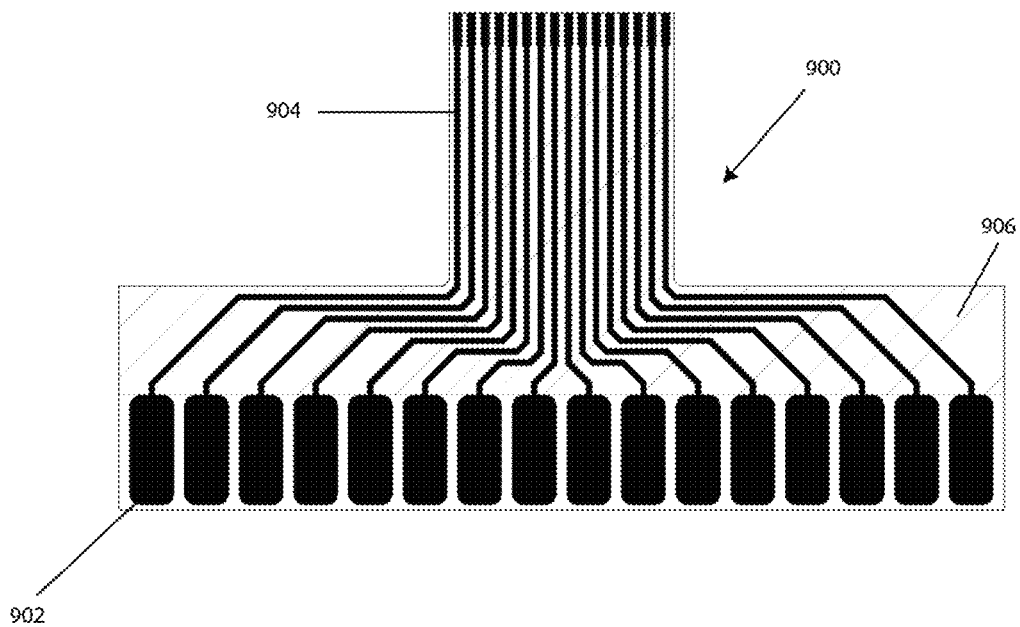
FIG. 9 illustrates an embodiment of a flexible circuit stimulation array. The substrate is flexible and able to wrap and conform around the wrist.

The circumferential array structure addresses issues of sizing. In some embodiments as shown in FIG. 9, the flexible array 900 of electrodes 902 could be made in a one-size-fits-all fashion and placed around any individuals wrist. However, electrodes 902 that are not used are simply not addressed by the stimulator. This allows one size to be customizable to a large population.

The array design is defined by the 1) center to center spacing, 2) the interelement spacing, and 3) the shape of the electrode, and 4) the electrical and mechanical properties of the skin interface, typically a hydrogel. In some embodiments, for wrist-worn treatment of tremors the array 900 has a center to center spacing of about 1 cm, an interelement spacing of about 2 mm, and rounded-corner rectangular elements such as 2 mm filet. Since the array 900 can conform to the body, the contacts can be fabricated as an electrically conductive Ag or Ag/AgCl trace 904 on a flexible polyester substrate 906, though other trace and substrates materials could be used such as gold plated copper on polyimide. A single strip of hydrogel with a reasonably high volume resistivity (~2500 ohm-cm) can be applied across the array and used to contact the skin. The selection of these parameters is determined by the desired range of anatomical sizes, electrical characteristics of the skin interface, sensation of stimulation, duration of stimulation, and permissible complexity of the electronics.

In some embodiments, the device is designed to minimize cross talk between elements/electrodes. Cross talk causes adjacent areas to be stimulated and can lead to draining power or increasing off-target side effects of the stimulation. Cross-talk can be minimized by selecting a hydrogel with a high volume resistivity to discourage current spread in the lateral direction and limit the effective area of stimulation. With lower volume resitivity, current spreading could prevent the ability to specifically target individual nerves. In addition, larger resistivity hydrogels tend to decrease edge effects and increase comfort of stimulation. However, a volume resistivity that is too large will consume more power, which increases demands on the electronics and the size of the battery. In some embodiments, an intermediate resistivity can be chosen in order to balance these competing needs. Additionally, a small amount of current spreading could also be beneficial to patient comfort as the current density will taper off more gradually.

Figure 10:
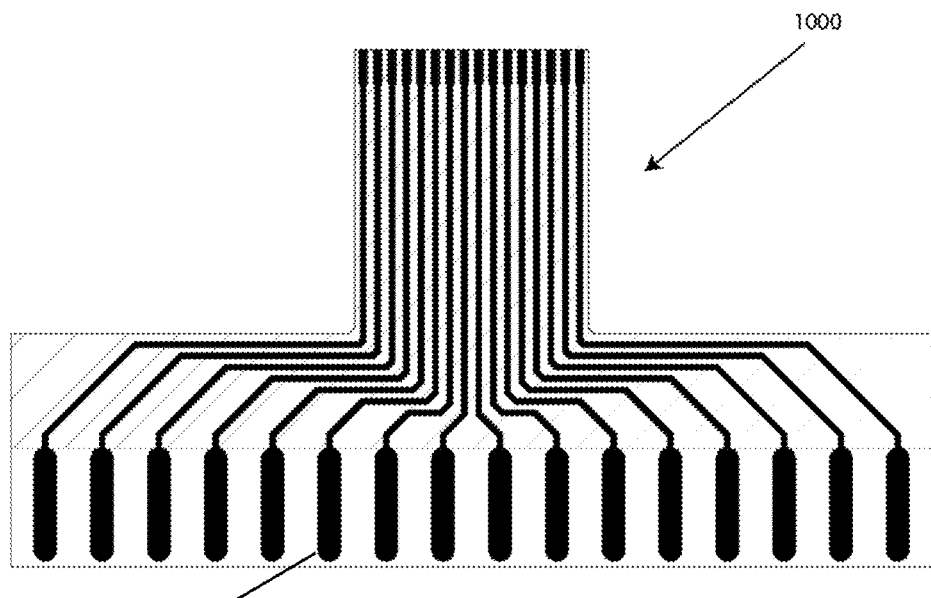
FIG. 10 illustrates an embodiment of a flexible circuit fabricated with smaller rectangular pads but similar interelement spacing as compared to FIG. 9 to reduce the effective area of stimulation and increase the sensitivity of the array to target a specific nerve.

Cross-talk could also be regulated by modifying the shape and the interelement spacing. For instance, decreasing the area of the electrodes 1002 (FIG. 10) in the array 1000 can help limit the excited area compared to FIG. 9. Modifying the center to center spacing can also limit the overlap area of neighboring elements/electrodes.

Figure 11:
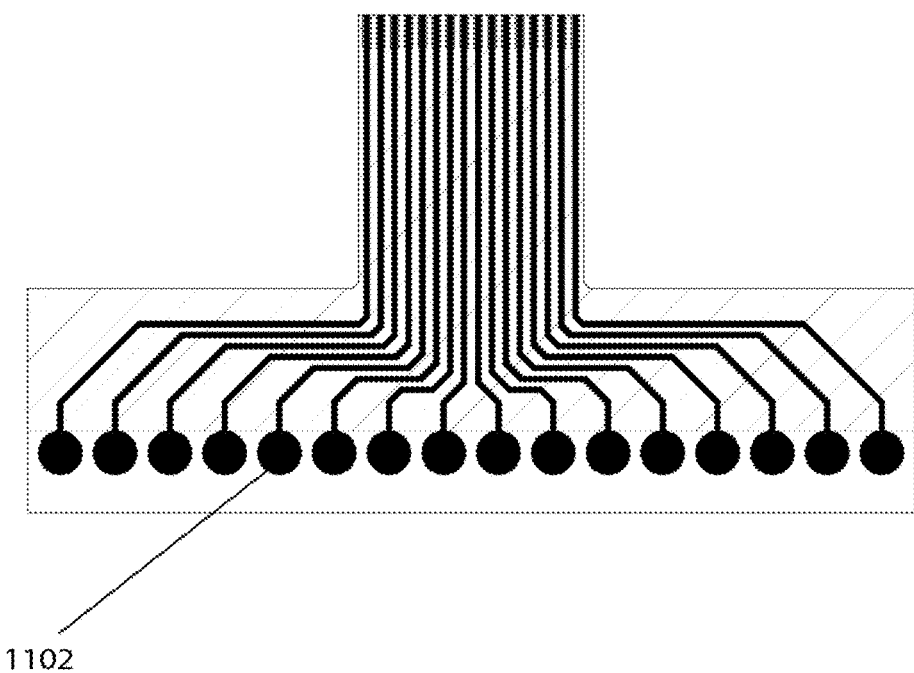
FIG. 11 illustrates an embodiment of a a flexible circuit fabricated with a circular electrode array.

Changing the electrode shape can also control the excitation in an area and make the stimulation more comfortable. In the case of rectangular elements, often the corners show an increase in current density, which can lead discomfort. In some embodiments, a circular element/electrode 1102 (FIG. 11) can be chosen to increase comfort.

A further approach to reducing cross-talk is to separate the hydrogel pieces and eliminate current flow from pad to pad. However, this increases the complexity of the manufacturing process.

Figure 12:
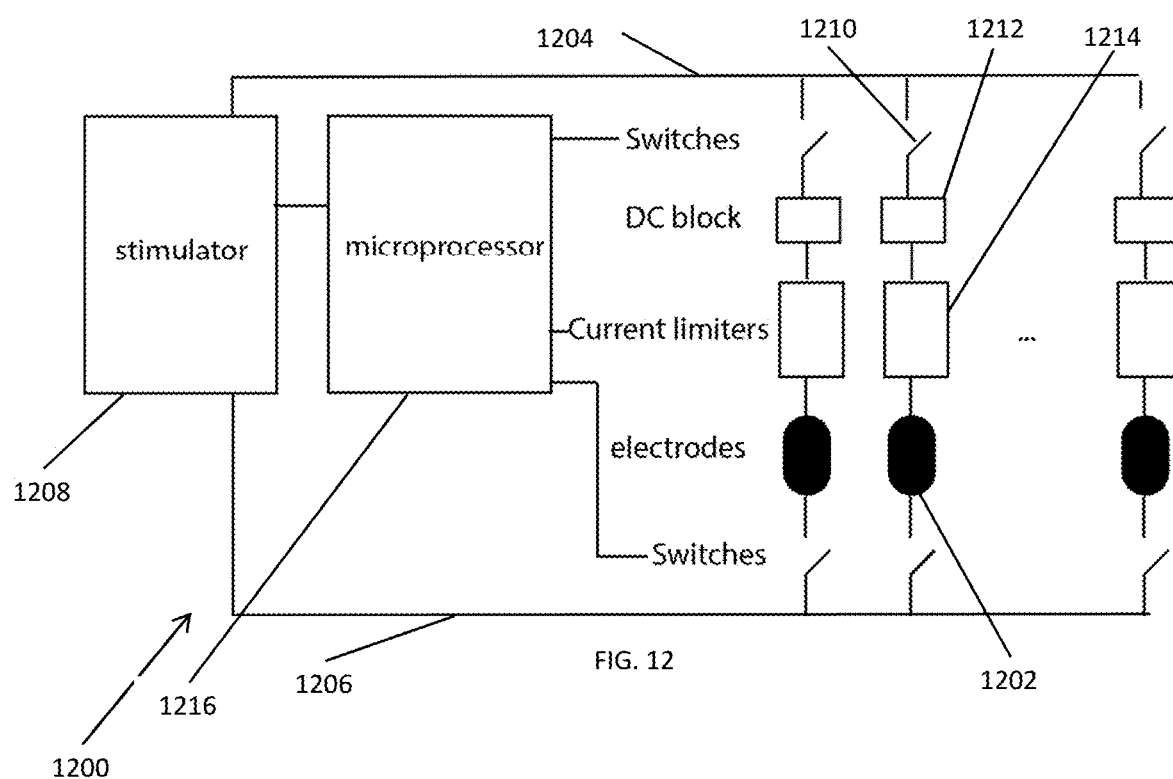
FIG. 12 illustrates an embodiment of a switching circuit that allows a single stimulator to address each electrode individually.

In some embodiments as shown in FIG. 12, the electronics and electrical circuit 1200 used to drive the array include an adaptable switch that allows each individual electrode 1202 to be connected to either one of the two contacts 1204, 1206 of the stimulator 1208 at a given time by opening or closing switches 1210 in each channel. Each channel can include a DC blocking circuit 1212, as charge balance is important to prevent skin irritation and burns, and also be individually current limited by current limiters 1214 in order to prevent current surges that could cause injury or discomfort. This current limitation can be set to a predetermined tolerability threshold for a particular patient or group of patients. There are many transistor circuits or components like polyfuses known in the art to limit or shutdown the current to a particular node. These circuits and its components, such as the stimulator, switches, and current limiters, can be controlled and/or be programmable by a microprocessor 1216 in real-time. The switch matrix allows multiple electrodes to be connected to the same stimulator contacts at a given time for maximum flexibility. In addition, electrodes can be switched between the positive and negative contacts of the stimulator to produce a bipolar pulse, as described below.

Another benefit of the array geometry is to map the physical layout of underlying neurophysiology. This could be used to tune the stimulation appropriately for each subject. For example, the array elements could be used to map the underlying muscle firing (electromyography) or the underlying nerve activity (electroneurography). This information may be used in a closed-loop system to monitor the tremor or optimize the stimulation over time.

Figure 13:
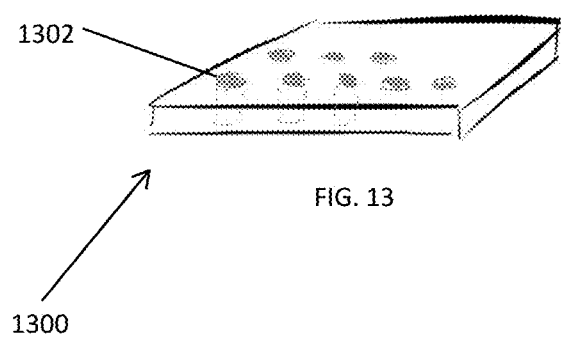
FIG. 13 illustrates and embodiment of a uni-directional conductive microarray of conductive elements in an electrically insulating carrier.

Expanding the underlying concept to the circumferential array described to a finer microarray offers significant advantages for stimulation. A structure that is a material with miniature, current-limited array elements would solve problems with current spikes or electrode peeling. Designing the microarray is a balance of a need for high lateral impedance to prevent crosstalk and low impedance for efficient power transfer from the stimulator. As shown in FIG. 13, such a microarray 1300 could be a woven fabric or a series of conductive elements 1302 in an insulating polymer to create a uni-axially conductive geometry.

Figure 14A:
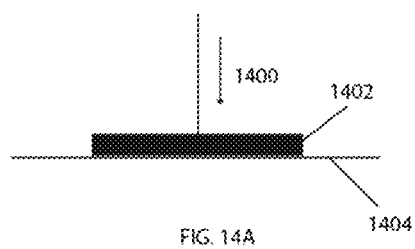
FIGS. 14A-14D illustrate the effect on current density when an electrode peels from the skin for a conventional electrode and array.
Figure 14B:
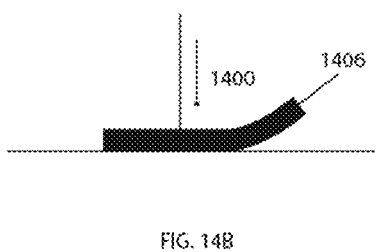

There are advantages to using a microarray instead of a conventional electrode system in order to maintain comfortable and safe stimulation in situations when the adhesion to the skin is compromised. Two situations generally cause pain and burns to a patient, electrode peeling and breakdown of electrode material; both are associated with increases of current density. In a conventional electrode system, as shown in FIG. 14A, current I 1400 is applied to a single electrode 1402 of area A attached to the skin 1404. The current density is then J=I/A. As the electrode peels 1406, as shown in FIG. 14B, the area A decreases, which increases the current density, J. The current density could increase to a point where the patient becomes uncomfortable or experiences side effects on the skin.

Figure 14C:
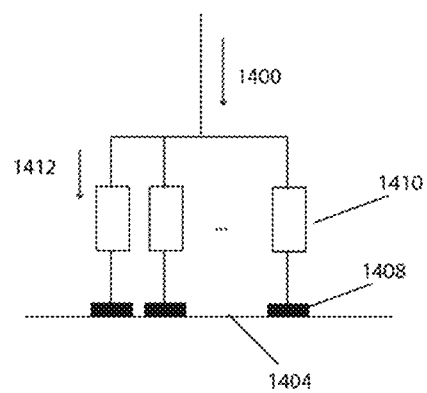
Figure 14D:
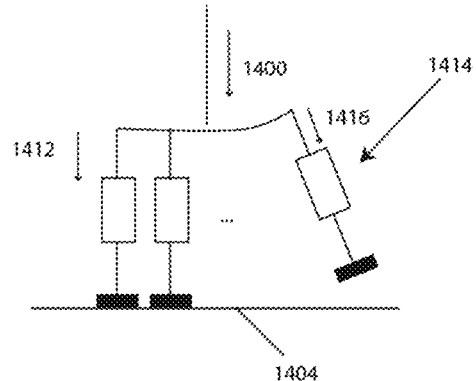

In a matrix array with regulated current density, however, the current density can be regulated to prevent discomfort. In FIG. 14C, the large electrode area is divided into an electrode array, with smaller elements 1408. Each element has an associated current limiting circuit 1410 that limits the current to a value that is comfortable 1412. Because these current limiters exist, in FIG. 14D, even when some of the array elements peel 1414 and zero current flows through those elements 1416, the current through all the rest of the elements 1412 is still limited to a level that is comfortable.

Figure 15A:
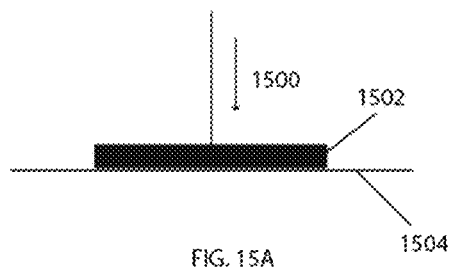
FIGS. 15A-15D illustrates the effect of an electrical short on current density for a conventional electrode and an array.
Figure 15B:
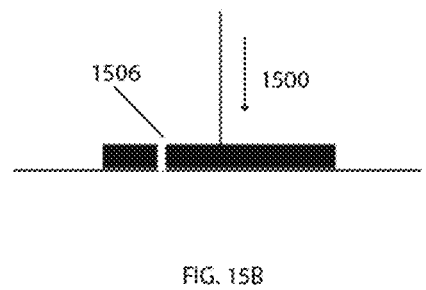
Figure 15C:
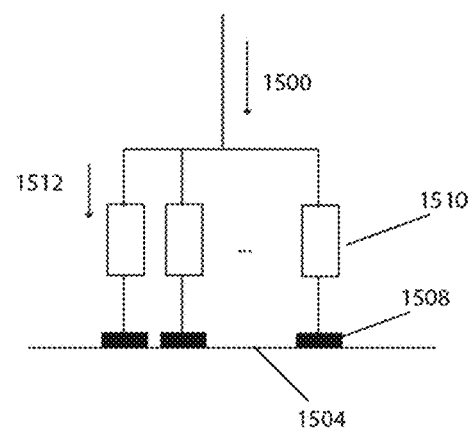
Figure 15D:
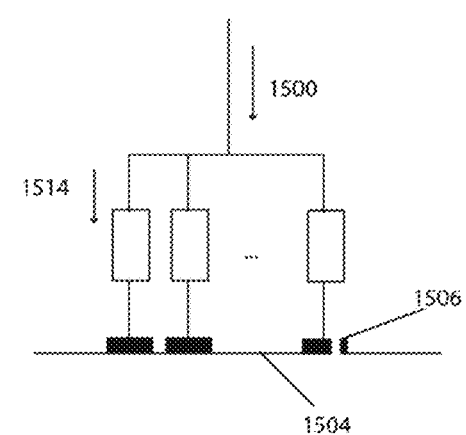

A second common situation where the microarray offers advantage over a conventional electrode system is when one area of the electrode is shorted due to a breakdown in the material or the mechanical nature of the material. In a conventional electrode system as shown in FIG. 15A, current I 1500 flows through an electrode 1502 on the skin 1504. In FIG. 15B, if a short circuit 1506 occurs in the electrode for example because of a defect or another reason, the whole current I 1500 flows through that single point, which could cause discomfort. In FIG. 15C, a multi element array has current limiters 1510 connected to each array element 1508. An example of such a current limiter is a very large resistor, R, much larger than that compared with the resistance, r, of the electrode itself 1508 (i.e., R>>r). In this case, the current through each element is roughly the total current divided by the number of elements. In the case where a short 1506 occurs in one element, since R>>r, the current through each element 1514 is still roughly equal to the total current divided by the number of elements.

Figure 16:
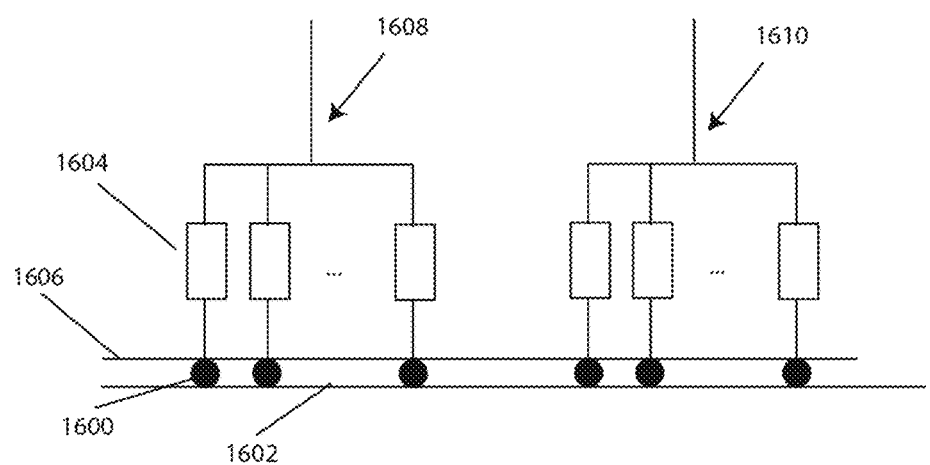
FIG. 16 illustrates an embodiment of a potential construction for an electrode array.

The two situations described would be particularly problematic for non-adhesive electrode configurations. For example, conductive fabrics may intermittently only contact one small region of the skin and cause all the all the current to flow through a small area at high current density. One solution to this problem is the embodiment of a non-adhesive array depicted in FIG. 16. This embodiment uses a series of fine pins or balls 1600 connected to a flexible substrate 1606, like cloth, to form the microarray of electrodes. Another material like a conductive foam or a comfortable layer 1602 can be added between the balls and the skin to address any discomfort, providing that the lateral resistivity is relatively higher compared to the through resistivity. This solutions minimizes the cross talk between the contacts. Such a microarray of elements/electrodes can be constructed as a matrix of multiple electrodes mechanically connected and each having their own current limiting circuit 1604. Electrodes in the matrix could be grouped into larger subgroups of elements that are individually controlled 1608 and 1610. Another option is to use a woven fabric where the resistance of each wire limits the current.

Patterned Stimulation Alternating Between Nerves

Figure 17:
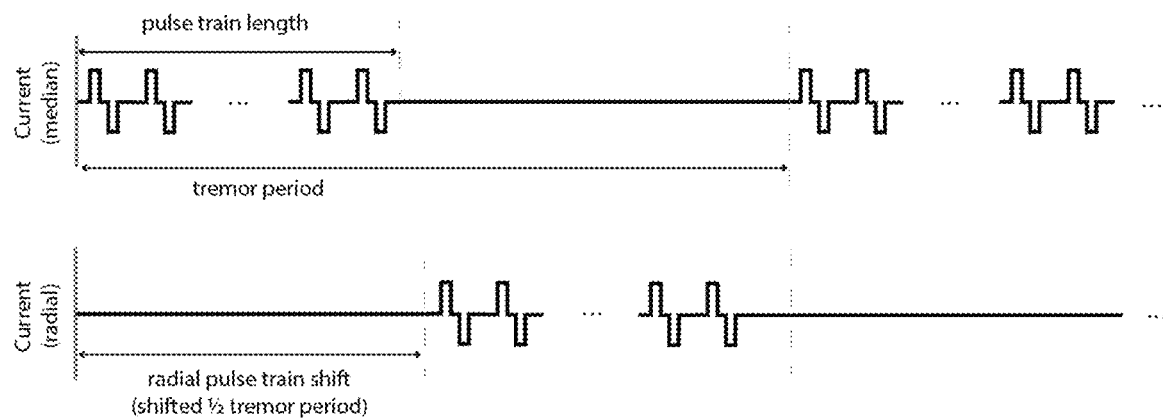
FIG. 17 illustrates a typical patterned waveform between median and radial nerve used to treat essential tremor.

One aspect of the device is the patterned waveform used to stimulate multiple nerves. This waveform uses alternating bursts of higher frequency stimulation (typically 50 Hz-2 kHz) and 50 µS-1 mS pulse width on peripheral nerves that map to adjacent locations in the brain. This type of stimulation may desynchronize the neuronal populations and restore normal function. These burst patterns match certain tremor characteristics of the patient, including the phase, frequency and amplitude of the tremor. In one implementation, where the median and radial nerves are used to treat tremor, pulse trains at 150 Hz frequency and 300 µS pulse width) are a length that is just under half of the tremor period and alternating between the two nerves. FIG. 17 illustrates a typical patterned waveform stimulating median and radial nerve used to treat tremor. Each burst is formed from pulses at a higher frequency and an appropriate pulse width for targeting the right types of nerves. The bursts alternate with timing relating to the patient's tremor frequency. Each burst is up to half of the tremor period such that the bursts are non-overlapping and the bursts are time-shifted by half the tremor period such that the alternating cycle is repeated with each tremor period.

Figure 18:
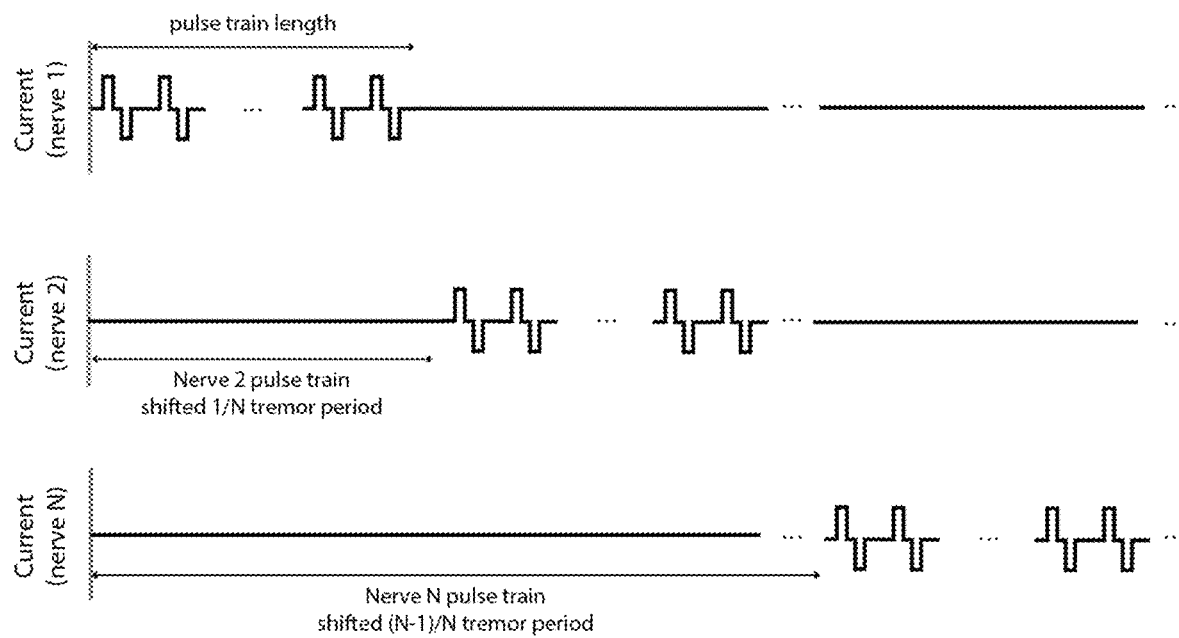
FIG. 18 illustrates a patterned waveform with N different nerves. The duration of each burst is equal to the period of tremor divided by N. Each nerve is excited by a burst and the whole pattern repeats in a time equal to the tremor period.
Figure 19:
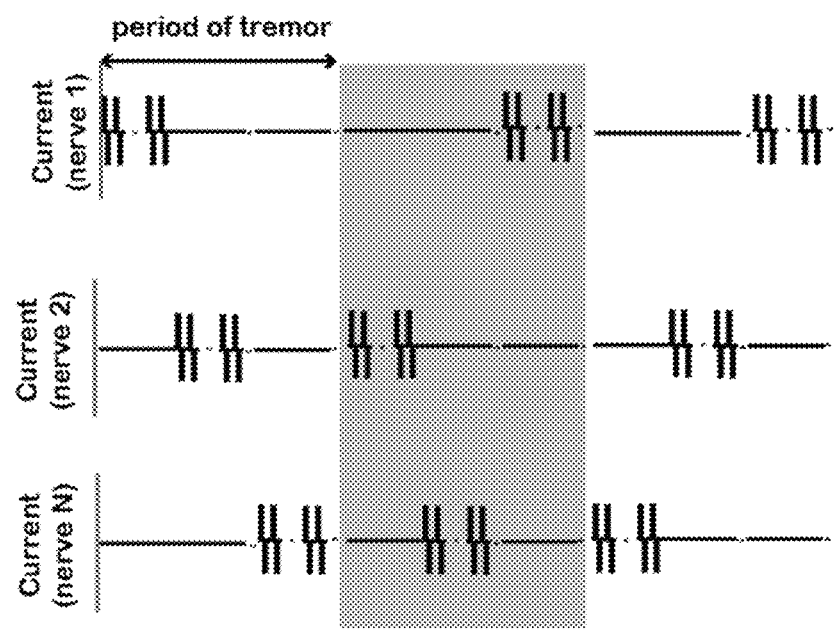
FIG. 19 illustrates an embodiment where the order of the pulse trains on different nerves are randomized.

There are several variations on this stimulation, including stimulating more than two nerves as shown in FIG. 18 and changing the ordering of pulse trains as shown in FIG. 19. If the number of stimulated nerves is increased to N, the maximum burst length of each pulse train will be 1/N times the tremor period such that the bursts are non-overlapping. The burst on the second nerve will shifted 1/N times, the burst on the third nerve will be shifted 2/N times, up to the final nerve N that is shifted (N−1)/N times the tremor period.

The order of the pulse trains on different nerves can be randomized as shown in FIG. 19. The upper limit on the length of the bursts is 1/N times the tremor period and the order of the bursts on the three nerves is randomized. However, all three nerves still experience a single burst of stimulation within a length of time equal to the tremor period, as illustrated by each white or gray section. In subsequent intervals of time equal to the tremor period, the order of the burst pattern on the nerves is again randomized.

Figure 20:
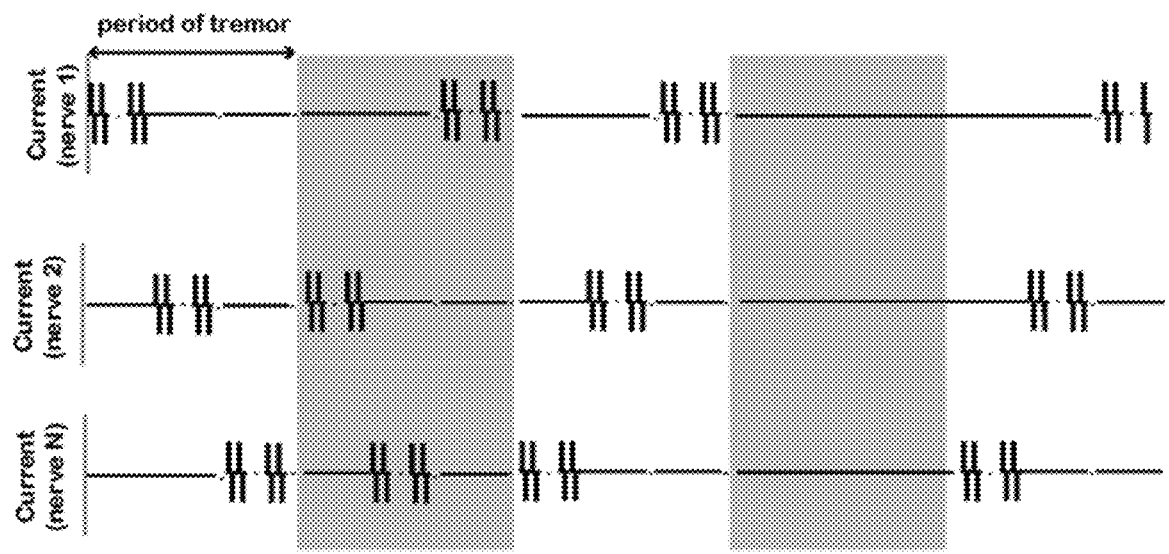
FIG. 20 illustrates a patterned waveform showing pauses in the stimulation.

There can be pauses at different times in the sequence. These pauses can be regular or occur at random times. The pauses may help with the desynchronization and also have the side effect of increasing the tolerability of stimulation because less power is generally transmitted to the hand. Less power transmission also reduces the power consumption from the battery and can help reduce the overall size of the wearable device. FIG. 20 illustrates a waveform pattern showing pauses in the stimulation. Each group of stimulation bursts is grouped in time intervals equal to the period of tremor. At regular times, stimulation can be stopped or paused for one or more segments equal in length to the period of the tremor.

While the embodiments described above have used constant 150 Hz stimulation as an example, the waveform within each burst can vary in amplitude, timing, or shape. For instance, in some cases, radial and median nerve amplitudes need to be changed since one nerve may be more easily excited than the other based physiology or hand position. The amplitude during the burst can also be varied, for example sinusoidally. The pulse width and frequency inside a particular burst pattern can also vary, for example, a stochastic resonance electrical stimulation pattern could be used to choose a random distribution of the pulse width and frequency of a certain square pulse. Stochastic resonance has been shown to enhance sensory perception and feed back into the central nervous system.

The electronics implementation of this alternating waveform is advantageous because only one stimulator is needed since only one nerve is stimulated at any given time. This is enabled by the switch matrix design described above and illustrated in FIG. 12. The advantage of the switch matrix design is that it helps achieve a safe design that reduces the size and cost of the device, characteristics essential for a wearable device. The specific advantages include:

Utilization of only one stimulator since only one nerve is excited at a time. This reduces the size and cost of the device by reducing the amount of electronic components required, compared to other techniques that need multichannel stimulators.

The switch matrix allows every electrode in an electrode pair to be associated with its own protection circuitry. This protects against any single point failure in the matrix. For instance, if a DC blocking capacitor is associated with every electrode, even if one of the capacitors failed, the patient would still be protected from DC currents from the second capacitor, as shown in FIG. 12.

Figure 21:
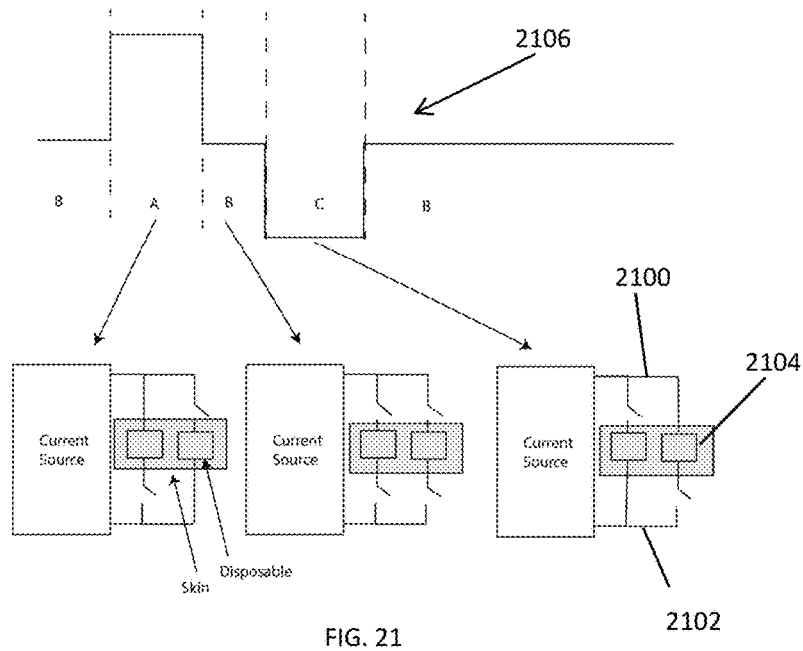
FIG. 21 illustrates how a switch matrix can be used to produce a biphasic waveform.

Additionally, the switch matrix minimizes or reduces the number of high voltage rails needed for biphasic stimulation, which reduces the number of components in the device. Instead of creating both negative and positive rails, a single voltage rail and ground rail are created. By connecting alternating electrodes to the ground rail or the high voltage rail, the biphasic waveform can be created as shown in FIG. 21. As shown in FIG. 21, two voltage lines, a high voltage line 2100 and a ground line 2102 are created, and electrodes 2104 are alternately connected to each voltage line to produce the biphasic waveform 2106. Reducing the number of components translates to space and cost savings that are critical to a wearable device.

Device Fitting for Electrode Arrays:

In some embodiments, a manual fitting procedure can be used. In a manual fitting procedure, the device can be placed on the patient's arm. Each individual electrode can be switched on and stimulation applied. The location of paresthesia can be noted for each electrode location and correlated to a particular nerve by using information found in literature. For example, if a particular array element causes paresthesia in the thumb, index, and third finger, then that electrode stimulated the median nerve. Ulnar and radial nerves can be found in similar ways. The operator can then program those nerve locations and corresponding associated electrodes into the patient's device. The device can recall these locations to provide consistent therapy to a particular individual, provided that the band and electrodes are consistently placed on the patient's wrist at the same location and orientation. To aid repeatable placement on the wrist, visual or mechanical markers that line up with anatomical features can be employed. One example is to curve the box to fit the curve of the wrist. A second example is to make the device watch-like, with intuitive preferred orientation. A final example is to provide visible indicators, like marks or lines that can line up with corresponding anatomy, like the tendons of the wrist or the bones on the hand and wrist, such as the ulnar styloid process.

Figure 22:
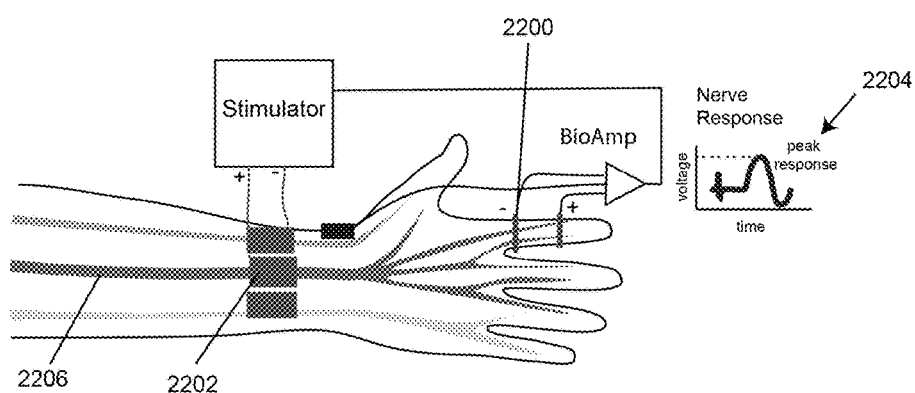
FIG. 22 illustrates how measurements of nerve conduction can be used to automatically determine which electrodes stimulate a target nerve.

In some embodiments, the fitting procedure can be automated using feedback from on-board sensors. For instance, one may use ring receiving electrodes 2200 on the fingers similar to those used in carpal tunnel nerve conduction studies. These receiving electrodes 2200 can be used to measure whether stimulation of a particular electrode 2202 placed circumferentially on the wrist or arm causes a measurable response 2204 in a target nerve 2206, such as the median, radial, or ulnar nerve, as shown in FIG. 22. This can also be used in some embodiments to confirm that a particular nerve, such as the ulnar nerve for example, is not stimulated, which can be accomplished by placing a electrode at a finger or other location that is innervated by that nerve. When the correct electrode(s) are stimulated, a response can be measured by the ring electrode on the finger or another electrode placed at known locations where the target nerve innervates.

In some embodiments, fitting can be determined by measuring the response to stimulation. For instance, if stimulation at a particular location leads to greater tremor reduction than stimulation at another location the device will be directed to stimulate the more effective location.

In some embodiments, during the fitting procedure, the search for the correct set of electrodes does not have to be done in a linear fashion. Depending on the person's wrist and width size, there can be a priori knowledge to the approximate locations of certain nerves. For instance, the median nerve is generally located close to the center line of the ventral side of the wrist, and therefore electrodes at that location can be preferentially tested.

Figures 23A, 23B:
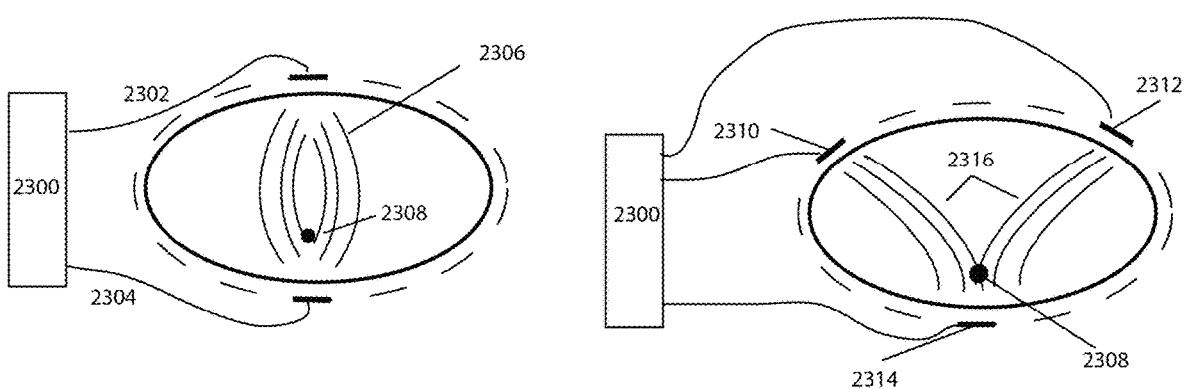
FIGS. 23A and 23B illustrate how changing the electrode selection or position affects the electric current field shape and density in the wrist.

While selecting individual elements is the most direct way of selecting a single nerve, more complex current patterns can be used to shape the current density through the limb. The combination of which electrodes to be used to excite a particular nerve can be straight forward or more complex in order to current steer for the purpose of improving comfort. For example, in FIG. 23A a simple configuration is achieved by connecting electrodes 2302 and 2304, on opposite sides of the wrist, to a stimulator 2300. Field lines 2306 excite nerve 2308. Another way of exciting nerve 2308 can be seen in FIG. 23B. Electrodes 2310, 2312, and 2314 are selected and connected to the stimulator. The amount of current passed through each electrode can be different in order to steer the field lines 2316. In other configurations, the current density could be reduced in order to make stimulation more comfortable.

A circumferential array is advantageous because array elements can be dynamically selected to change stimulation as necessary. For instance, in some cases, as the position of a person's limb moves around, the position of a nerve can change. In this situation, a different set of electrodes than the original pair may target the nerve more precisely or efficiently and it is advantageous to apply an algorithm to change the set of electrodes used for stimulation.

Dynamic Stimulation Algorithms

In addition to the effective positioning of the electrodes around the patient's arm or wrist, in some embodiments the electrical stimulus delivered to the nerves through the electrodes can be improved in various ways, including for example determining various characteristics of the tremor and using this data as feedback to modify, adjust and set various stimulation parameters as shown in FIGS. 24A-24F and described in more detail below.

Dynamic algorithms can also help stimulation comfort and reduce redness or rash. If multiple elements target specific nerve or nerves of interest, the signal can be switched between these different elements in real-time. This may alleviate the irritation at a particular location of the skin by reducing the time of stimulation at a particular location. However, the total net effect of therapy will be the same.

Figure 24A:
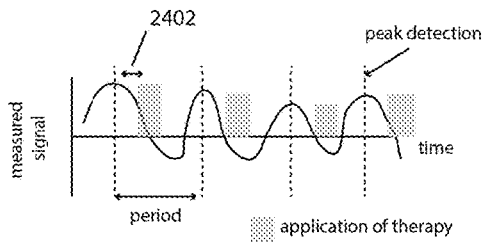
FIGS. 24A-24F illustrate how various characteristics of the tremor can be used as feedback to adapt stimulation delivered to the patient. In addition, predictive adaptation based on information gathered from the patient's calendar, for example, can be used to trigger stimulation.

Tremor Phase Feedback:

In some embodiments as shown in FIG. 24A, the tremor signal, measured by accelerometers, gyros, or other means like EMG, can be used for direct feedback. For example, using the gyroscope signal allows the angular speed of the hand to be measured, and thus the angle of the hand can be calculated. It has been shown that responding out of phase to the tremor can be effective in reducing tremor. Detecting and responding to the phase delay 2402 can be accomplished in hardware or software.

To utilize tremor phase feedback, the signal from the motion sensor can be integrated, or a combination of sensors can be used to form a signal that is reflective of hand position. For example, position and orientation can be determined by integrating accelerometer or gyroscope signals, or by combining the accelerometer, gyro, and magnetometer data to produce a quaternion showing the orientation of the hand. By combining the positions in one or more axes, it is possible to produce a signal used for dynamic feedback.

One algorithm of calculating the triggers for the stimulation identifies where the derivative of the signal changes sign to find peaks in the signal. The signal may be noisy, so a filter or threshold may be required to eliminate noise oscillations. Finally, peaks usually do not occur faster than the typical tremor frequencies (4-12 Hz), so points that are too close together can be eliminated. From the peaks, the instantaneous frequency of the tremor can be calculated by looking at the difference in time between the two peaks. Then, using this frequency, the appropriate time delay needed to stimulate out of phase can be calculated, accounting for the delay in the neural signal from the peripheral nerve to the brain. The calculation is done and real-time and can be adapted to the instantaneous frequency and phase of the signal.

An alternative approach would be to detect zero crossings or any other repeated value in the position or biological signal. However, zero detection can be challenging due to the tendency for noise around zero.

An alternative approach to detecting phase is to use the real-time Hilbert transform. The Hilbert transform will calculate the envelope and phase from a real-time signal. The instantaneous phase can therefore be used to time the stimulation appropriately. However, the Hilbert transform is complex and challenging to implement on a standard microcontroller.

Figure 24B:
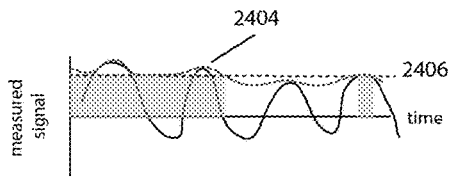
Figure 24C:
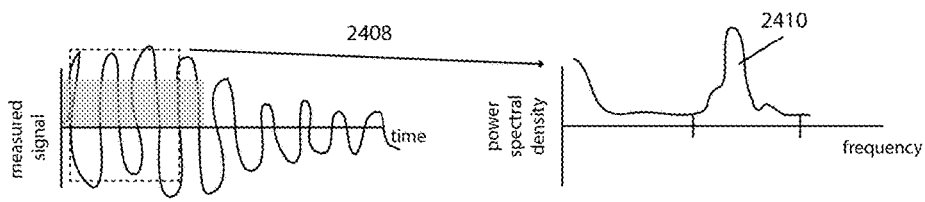

Tremor Amplitude Feedback:

In some embodiments, tremor amplitude feedback modulates the duty cycle of the treatment based upon tremor severity. Tremor amplitude can be defined and determined in a number of ways as shown in FIGS. 24B and 24C, including: (1) maximum or root-mean-square flexion extension/position, velocity, acceleration, or jerk of the hand motion; or (2) the spectral power at a frequency or spectral energy in the 4-12 Hz band. Determining maximum hand motion can become computationally expensive because of the three-dimensionality. In some embodiments, the signals from all axes in the gyroscope or accelerometer can be integrated and the axis with the largest amplitude can be taken to define the amount of flexion and extension. An alternative implementation is to calculate the orientation of the hand from a combination of sensor inputs, and the axis-angle rotation from the neutral position of the hand at an instantaneous point in time can be calculated to specify the degree of flexion/extension. If the envelope 2404 of this oscillatory signal is larger than a threshold 2406, therapy can be applied.

This approach may be computationally intensive and it may be preferable to calculate the spectral energy in the 4-12 Hz band for a short time signal. If a multi-axis accelerometer, gyroscope, or other motion sensor is available, the spectral density can be calculated individually for each axis and then the L2 norm can be found. The L2 norm could also be calculated prior to finding the spectral density depending on the sensors used. The spectral density can be calculated using a variety of numerical approaches 2408 taking the signal from the time domain to frequency domain, including FF 1', welch or periodograms, or using a more microcontroller friendly Goertzel tone detection algorithm, all of which are well known in literature. If the energy under the curve 2410 is larger than a threshold, therapy can be applied.

One difficulty of this feedback mechanism is determining the threshold at which therapy should be applied. In some embodiments, the threshold can be set based upon the actual angle of the hand; surveys and patient tests can determine the acceptable angle ranges for performing daily tasks, like drinking or holding a spoon. The same can be done for spectral density. In some embodiments, this threshold can be set as universal across all patients In some embodiments, the threshold may be individualized to a particular patient or group of similar patients. This could be done by monitoring the patient's tremor level (e.g., energy or position) over time and determining the maximum and minimum values for the person in a normal situation. These values could also be recorded over time. Alternatively, the tremor threshold can be defined as a fraction of the minimum value of the tremor.

In some cases, including Parkinsonian tremor, there may be a habituation to stimulation and the tremor will start to increase again after a short period. Detection of an increase in tremor severity can be used to modify amplitude, phase, frequency, waveform, or pulse train of the stimulation to improve efficacy and durability.

Tremor Frequency Feedback

Figure 24D:
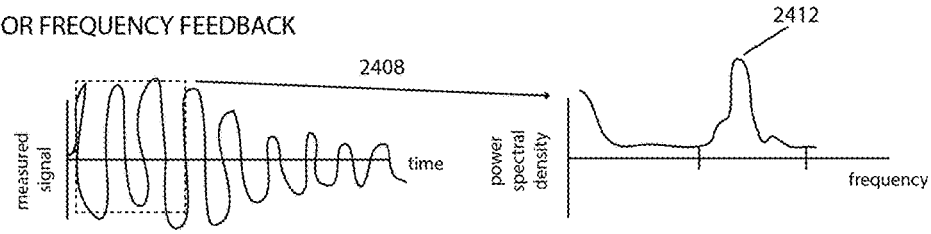

In some therapies as shown in FIG. 24D, the frequency of the tremor is used to set the cycle of nerve excitation. For example N units in the same neural cluster innervated by N peripheral nerves should be stimulated at a time separation equal to the period of the tremor divided by the N. Since the frequency of the tremor does not change rapidly, as described below in the section on TREMOR DETECTION, sampling at minute intervals should be sufficient for tracking the tracking. The spectral density as a function of frequency will need to be calculated using the numerical approaches 2408 described above. If there are multiple axes, their spectral densities can be combined, for example, using an L2 norm. The peak frequency 2412 in the spectral density curve can then be used to time alternating bursts of stimulation between the nerves.

Predictive Adaptation

Figure 24E:
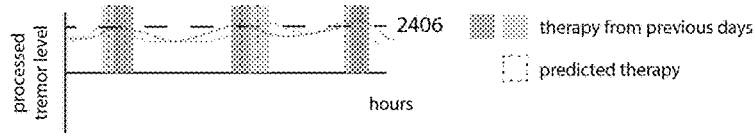
Figure 24F:
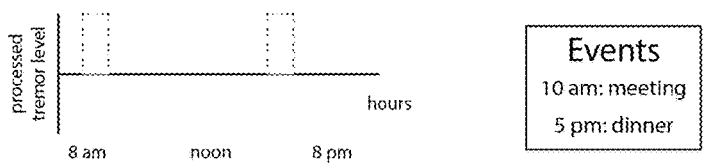

A patient's tremor amplitude and frequency can have daily patterns. In some embodiments as shown in FIGS. 24E and 24F, understanding historical tremor measurements and the time therapy was applied can inform therapy needed on successive days. Neural networks, Kalman filters, and other such predictive algorithms can be used to predict when tremor will increase and apply pre-emptive treatment.

In addition, long term data collection over the span of months or years can provide information on disease progress and the need to adapt therapy. For instance if a person's tremor has been getting worse with the same degree of therapy, and if increasing amounts of therapy are needed to maintain the same overall effect, it may be desirable to modify treatment.

Often a user has external information that can be used to prevent tremor. For instance, tremor is often brought on by stressful events, such as presentations and meetings. Since many patients with tremor already schedule these events, for example in a calendar, the calendar can be used to inform prediction of when treatment may be needed. For instance, if a patient has a meeting scheduled for 1:00 pm, the device may pre-emptively start stimulation at 12:40 pm. A patient could also activate the therapy using a button if suddenly stressed.

Big Data Approaches

Figure 25A:
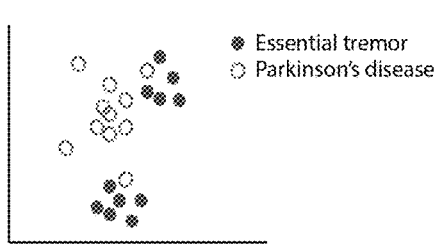
FIG. 25A-25C illustrate how big data compiled from large populations combined can improve disease and tremor classification, which allows recommendations of treatments as well as long-term monitoring of tremor.
Figure 25B:
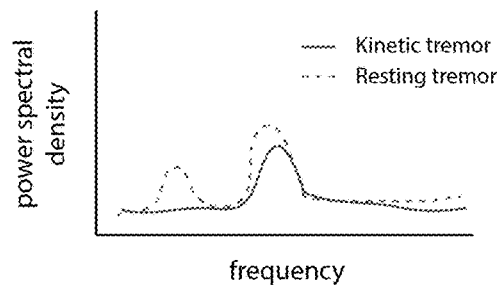
Figure 25C:
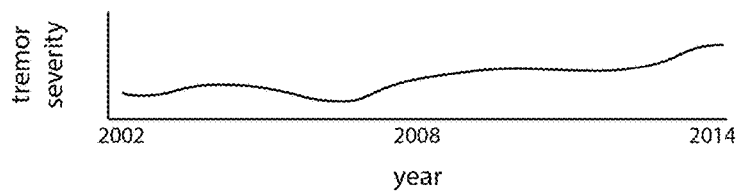

As shown in FIGS. 25A-25C, treatment modification can also be determined through the use of big data analytics which can utilize long-term monitoring of broad populations. Demographic information about each individual as well as tremor characteristics (e.g., the degree of postural, resting, and kinetic tremors) can be used to categorize people into different subtypes. FIGS. 25A and 25B depict the disease segmentation by separating kinetic tremor characteristics of essential tremor from resting tremor characteristics of Parkinson's disease. FIG. 25C depicts the long-term tracking of changes in an individual's tremor severity. Recommendations on different types of treatment can be made to new patients in the subgroups, similar to Netflix's approach of recommending movies based on the user's similarity to other users. This technique could be implemented using principal components analysis, k-means clustering, or other well-known numerical segmentation approaches.

Figure 26:
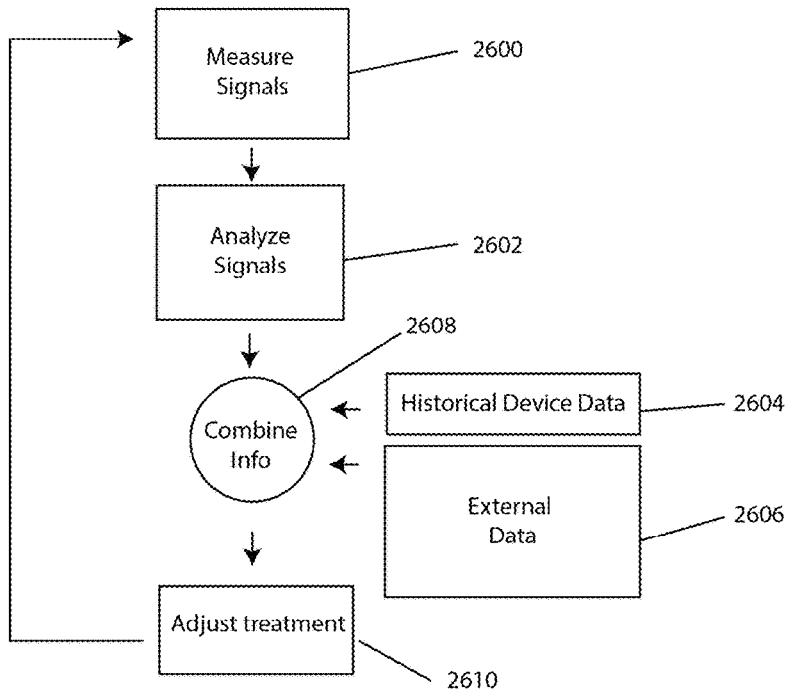
FIG. 26 illustrates a flow chart that shows how tremor feedback, long-term monitoring data, external data, and predictive adaptation can be used to adjust treatment.

All the above forms of adaptation, feedback, and external information, like cloud data, can be integrated together to enhance treatment. FIG. 26 shows a flow chart of such a system. In step 2600, sensors can be used to detect motion, position or other biological signals over time. In step 2602, a processor can receive the sensor data and calculate various metrics, such as tremor amplitude, phase or frequency. In step 2604, the method and system can obtain past history data, and in step 2606, external information, such as data from the cloud, can be sent to the processor of the device; cloud data can include population derived data, calendar data, and input entered into the device. The processor can combine all this data in step 2608 and can adjust the stimulation treatment and parameters in step 2610 based on this combined data. The method and system can then loop back to step 2600.

Amplitude Setting

One aspect of the design is the method of how optimum amplitude of stimulation is identified and reached during a session. This method is important towards the comfort and efficacy of the treatment. The perception of stimulation differs among patients and circumstances. For instance, an instantaneous increase in amplitude directly from 0 mA to the optimum stimulation level can cause an uncomfortable sensation. A slower increase of stimulation can be more comfortable, but a wearer's perception of the amplitude of stimulation may not be linear with applied current amplitude. If there is a long period where the wearer has no perception of stimulation, for instance if the device ramps linearly from zero amplitude, the wearer may even think the device is broken.

Two subjects were studied in an experiment to understand the perception of stimulation level. Electrodes were positioned to target the median and radial nerves separately. During the session, the stimulation was ramped slowly at 0.1 mA increments to identify the sensation threshold, muscle contraction threshold, and discomfort/pain threshold. After these points were identified, the subject was allowed to rest for several minutes until the sensation of tingling went away. Then, the current amplitude was ramped from the sensation threshold to 85-90% of the stimulation threshold of muscle contraction or discomfort/pain, whichever occurred at the lower amplitude. At each step, subjects were asked to shade a drawing to see where the paresthesia was felt and also mark on a visual analog scale (VAS) how intense they felt the stimulation compared to the maximum level they felt previously. The distance of their marks on the VAS were then tabulated and normalized to the length of the VAS marker.

Both subjects reached a muscle contraction threshold (i.e., when they felt their hands were heavy and difficult to move) before severe discomfort. Results are shown in Table 3. This result suggests that amplitude for median and radial nerves are different and potentially should be adjusted separately to achieve optimum stimulation for both nerves. In both subjects, the radial nerve could have been stimulated at much higher amplitudes to achieve a greater effect.

TABLE 3

Results of stimulation thresholds for two subjects to understand the relationship between sensation and stimulation amplitude.

| | Radial sensation threshold (mA) | Radial muscle action threshold (mA) | Median sensation threshold (mA) | Median muscle action threshold (mA) |
|---|---|---|---|---|
| Individual 1 | 2.5 | 4.7 | 3.1 | 5.4 |
| Individual 2 | 2.2 | 5.4 | 2 | 4.7 |

Figure 27A:
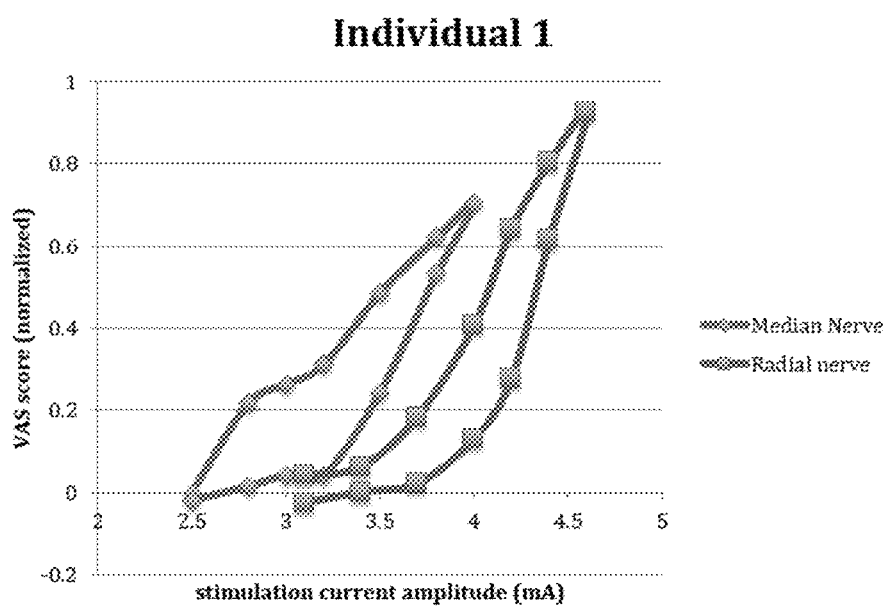
FIGS. 27A and 27B present results from two subjects that show the relationship between patient sensation and stimulation amplitude.
Figure 27B:
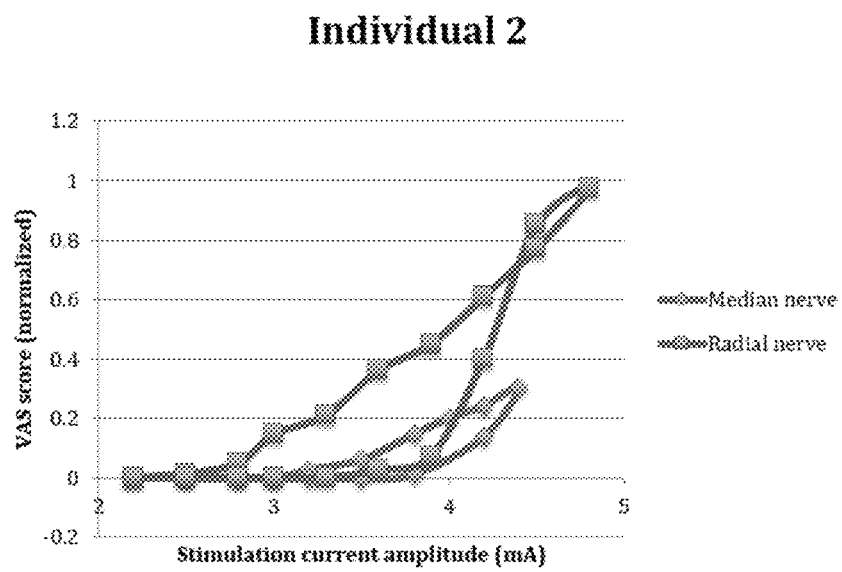

A great degree of habituation and hysteresis were observed in the sensation of stimulation, as shown in FIGS. 27A and 27B, which show the relationship between patient sensation and stimulation amplitude for two subjects. When increasing stimulation towards the 85-90% level of the maximum sensation threshold, the individual showed a steep, nearly-linear rise between the level of first sensation and the maximum level. However, when stimulation was decreased, perception of the stimulation intensity had a slope that dropped more rapidly than during the increase in amplitude.

Figure 28A:
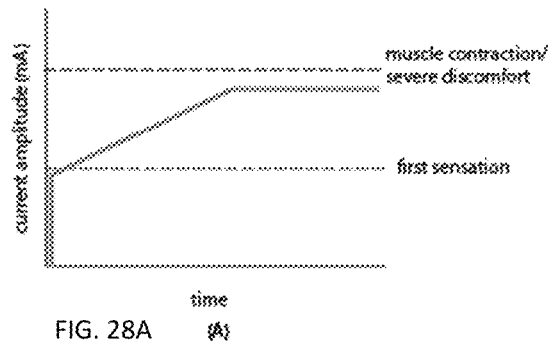
FIGS. 28A-28D illustrate various ramp types.
Figure 28B:
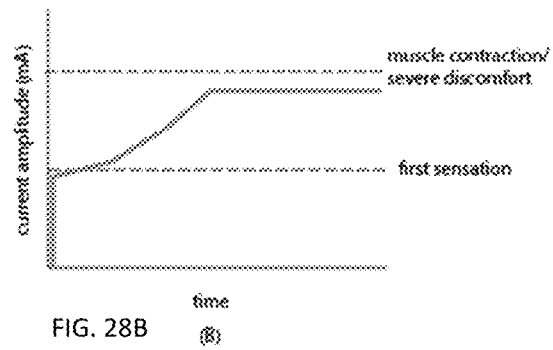
Figure 28C:
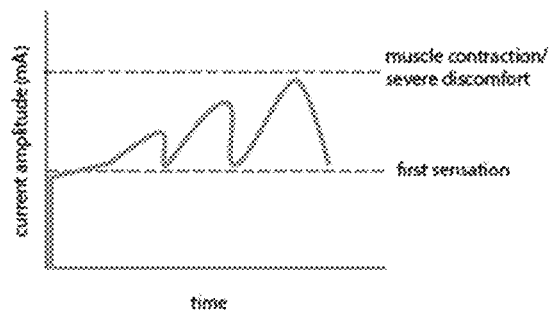
Figure 28D:
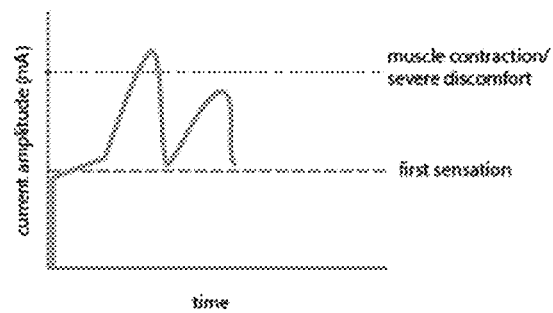

This result indicates that the stimulation ramp could be fairly linear between the threshold of first perception and 85-90% of the max stimulation level (from discomfort or muscle contraction). Me ramp should not start linearly from zero, because the first perception occurred at amplitudes half of the max threshold. Thus, if the ramp is slow and linear from 0, for half the time of the ramp, the patient may feel no sensation. Another stimulation could be exponential to reflect the exponential appearance of the radial nerve measurement for Individual 1. FIGS. 28A-28D illustrate various ramp types. FIG. 28A shows that the measured data suggests a linear ramp rate between the first sensation and max motor contraction/discomfort threshold would work in terms of constant perception of the amplitude. FIG. 28B shows an exponential increase, which could have to occur if the patient becomes habituated to the stimulation. FIG. 28C illustrates a periodic waveform showing the amplitude ramping up and down to different maximum amplitudes. A patient may become more habituated as the waveform amplitude is gradually increased, so a higher treatment amplitude may be tolerated by the patient. FIG. 28D illustrates another method for achieving higher treatment amplitude, which is to surpass or actually reach the level of discomfort on the first ramp up; in this way the patient could become immediately or rapidly habituated and be able to withstand higher stimulation during the treatment time.

Figure 29A:
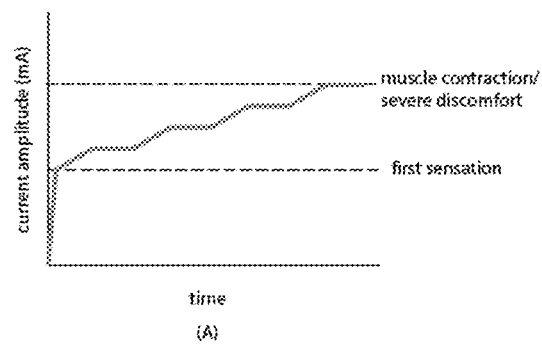
FIGS. 29A and 29B illustrate a series of small ramps that increase stimulation level, with either pauses or a small decrease in level between each ramp.
Figure 29B:
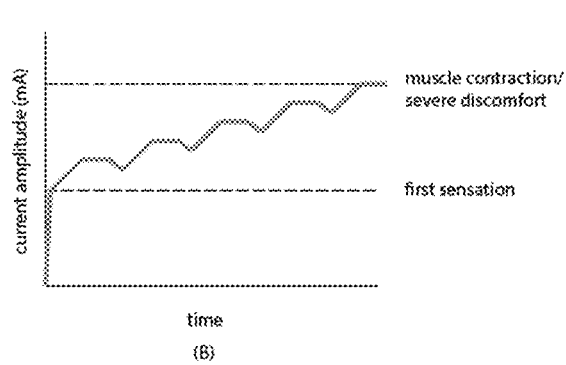

Also, because of habituation and hysteresis, if a higher stimulation level affords greater efficacy, in some embodiments, the waveform can be a series of smaller ramps that increase stimulation level, with either pauses or a small decrease in level between each ramp as illustrated in FIGS. 29A and 29B, which will allow an individual to have a higher stimulation amplitude with less discomfort.

Tremor Detection

Figure 30:
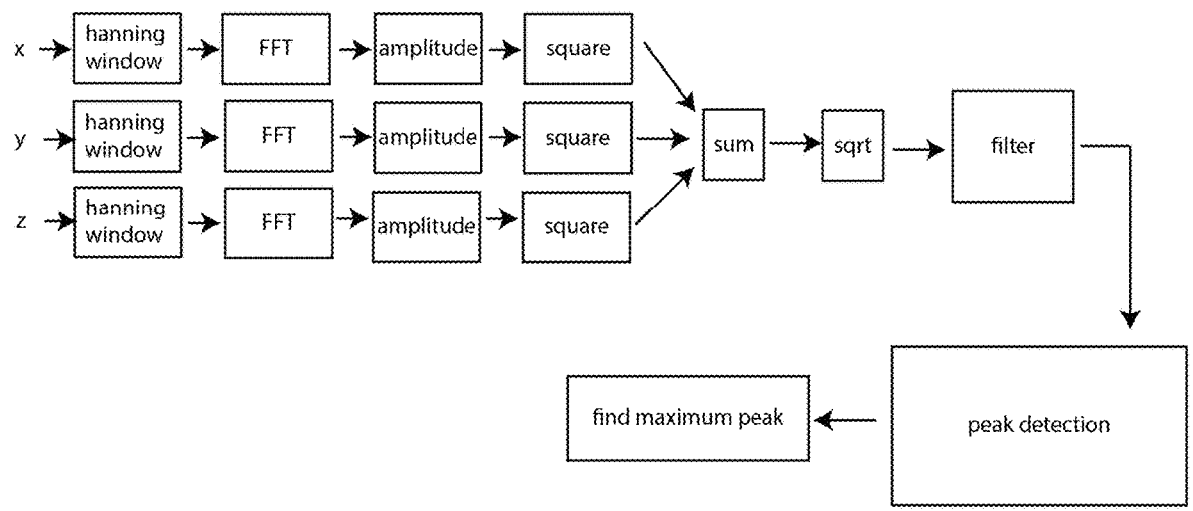
FIG. 30 is a flow chart of how tremor frequency can be calculated from 3-axis sensors.
Figure 31A:
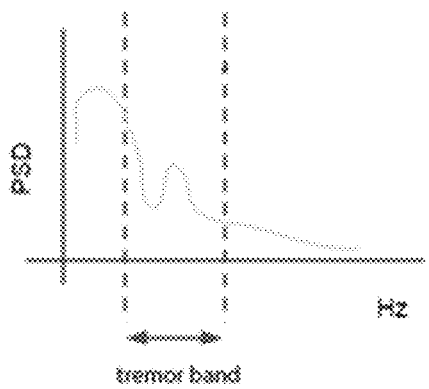
FIGS. 31A and 31B illustrate how a false or inaccurate peak in tremor frequency can be detected.
Figure 31B:
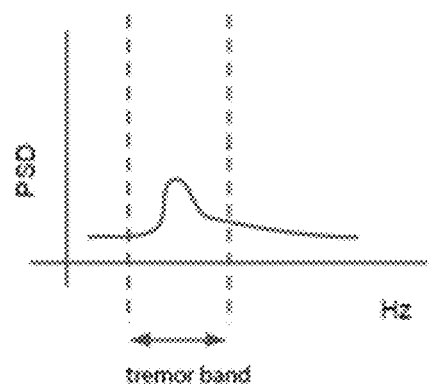

As discussed above, adaptively modifying the stimulation may require detecting tremor characteristics by processing one or more motion sensors, such as different multi-axis sensors. FIG. 30 is a flow chart of how tremor frequency can be calculated from motion sensors. It is advantageous to use multi-axis motions sensors over single-axis since tremor motion does not always occur along the same direction, especially if different actions are being performed. For instance a 3-axis gyroscope can be used to measure the tremor from the wrist. Each axis is then individually windowed and the Fourier transform is applied. The magnitude of each axis is then calculated and the square root of the sum of the squares of the axes are calculated as a function of frequency. The summed spectrum is then smoothed with a box car filter or other low pass filter, and the peak frequency in the 4-12 Hz range is identified. The frequency may be detected by determining the frequency at the maximum value in the 4-12 Hz range. However, as depicted in FIG. 31A, in some cases the boundary artifacts from processing may be falsely interpreted as a signal maximum. One approach shown in FIG. 31B is to first do an aggressive band pass filter from the 4-12 Hz band prior to taking the FFT. A second approach is differentiate the curve and find the zero crossing points, then from that subset of zero crossing points find the frequency value with the maximum spectral amplitude. Gyroscopes are generally preferred for spectral analysis since they typically do not have the DC offset of accelerometers.

Figure 32:
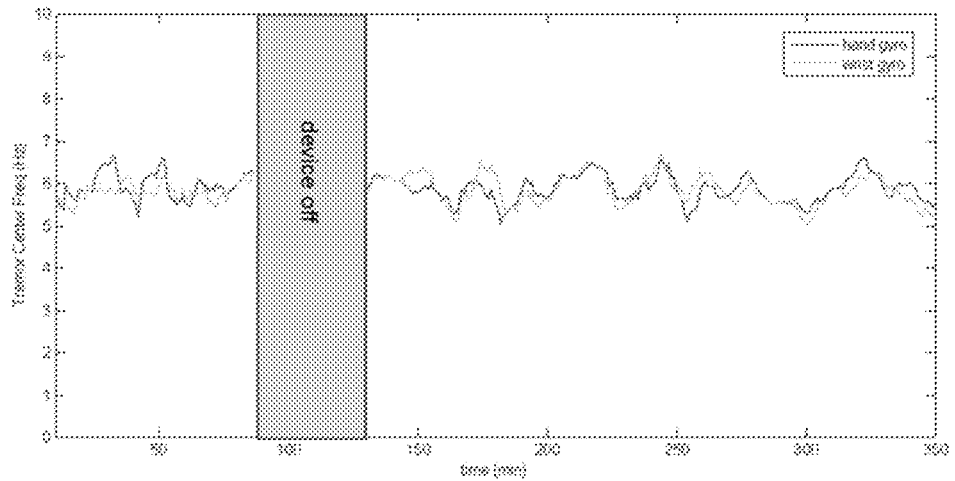
FIG. 32 illustrates how the tremor frequency varies over the course of a day.

In some embodiments, the frequency can be updated sporadically (versus continuously) because the timescale of frequency shifts is long. This a major advantage over devices requiring real-time responsiveness as it is a significant simplification that leads to smaller battery sizes, improved form factor, and the ability to measure tremor from high quality sporadic data instead of requiring continuously high quality tremor extraction from real-time data. FIG. 32 shows data from an individual with tremor wearing an inertial measurement unit (IMU) over a day, where the tremor frequency does not vary dramatically. The mean frequency was 5.86 Hz and spread of frequency varied over 1.6 Hz.

In some embodiments, the frequency of the tremor is measured from the wrist. While tremors are typically measured at the hands, as shown in FIG. 32 the wrist and hand gyro frequencies track each other well and are well correlated. The average difference between the hand and wrist gyroscope was 0.076 Hz with a maximum deviation of 0.8 Hz, which is well within the spread of frequency variations within the day. Measuring tremor from the wrist has major advantages over devices requiring measurement on the hand as it can be done with watch-like form factors. In a device targeting the median, radial or ulnar nerves in a circumferential band on the wrist it implies that the sensors for measuring tremor can be on-board the same device used for stimulation.

In some embodiments, the tremor period can be measured from mechanical inputs using gyroscopes, accelerometers, bend sensors, pressure sensors, etc. from the back of the hand, wrist, or any part of the limb that exhibits tremor In some embodiments, the tremor can be measured via EMG or other electrical signals.

In some embodiments, the tremor frequency can be measured at all times and then used to update the stimulation in real time.

Figure 33:
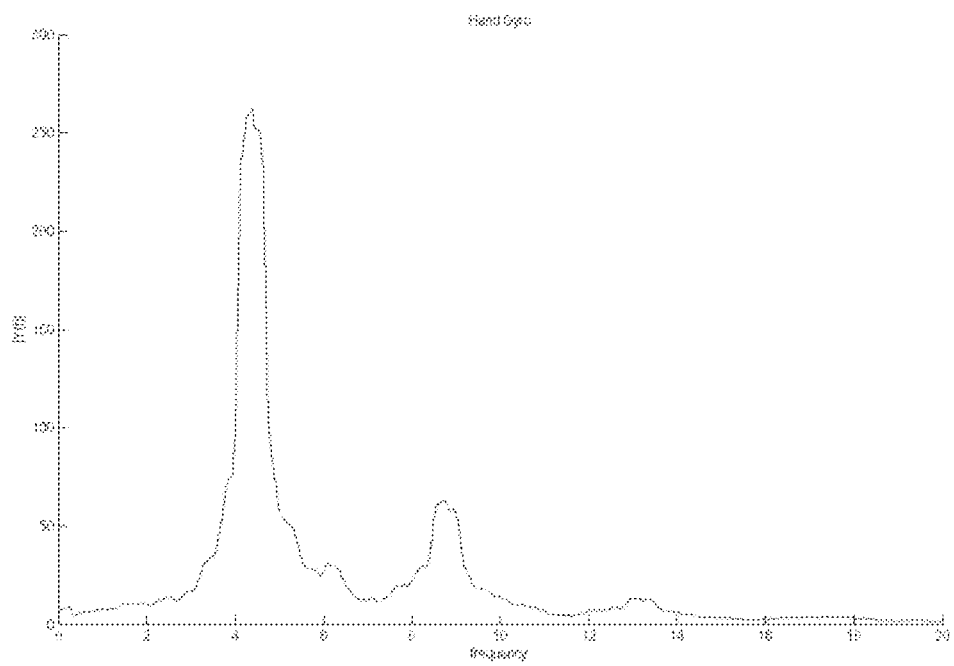
FIG. 33 illustrates how other physical activities could be mistaken for tremor.

In some embodiments, the tremor frequency can be calculated only in situations where it is appropriate. For instance, looking at the band of lower frequencies or other patterns in the spectrum, certain measurements can be eliminated due to confounding voluntary activity. For example, FIG. 33 illustrates frequency'spectrum analysis from a person with no tremor while jumping. The results of this analysis could clearly be mistaken for tremor, but patterns of high frequencies can be identified and used to eliminate certain activities or combined with sensor measurements to predict behavior.

Figure 34:
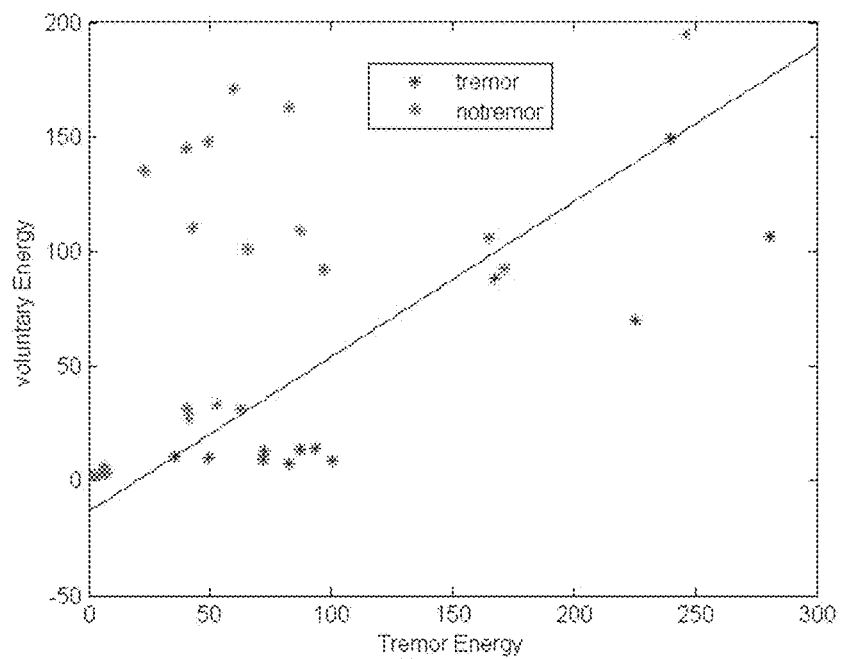
FIG. 34 illustrates a regression model of tremor versus non-tremor activities as an example of how to identify activities from which to calculate the center frequency of tremor.

One aspect of the system and method is differentiating tremor movement from non-tremor (or voluntary) movements, or detecting activites known to produce tremor to selectively measure tremor. FIG. 34 shows an analysis of 32 activities performed with and without tremor. Using the energy in the voluntary band (0.1-3 Hz) and tremor band (4-12 Hz), a logistic regression model was created that could segregate tremor versus non-tremor activities.

Band

Figure 35:
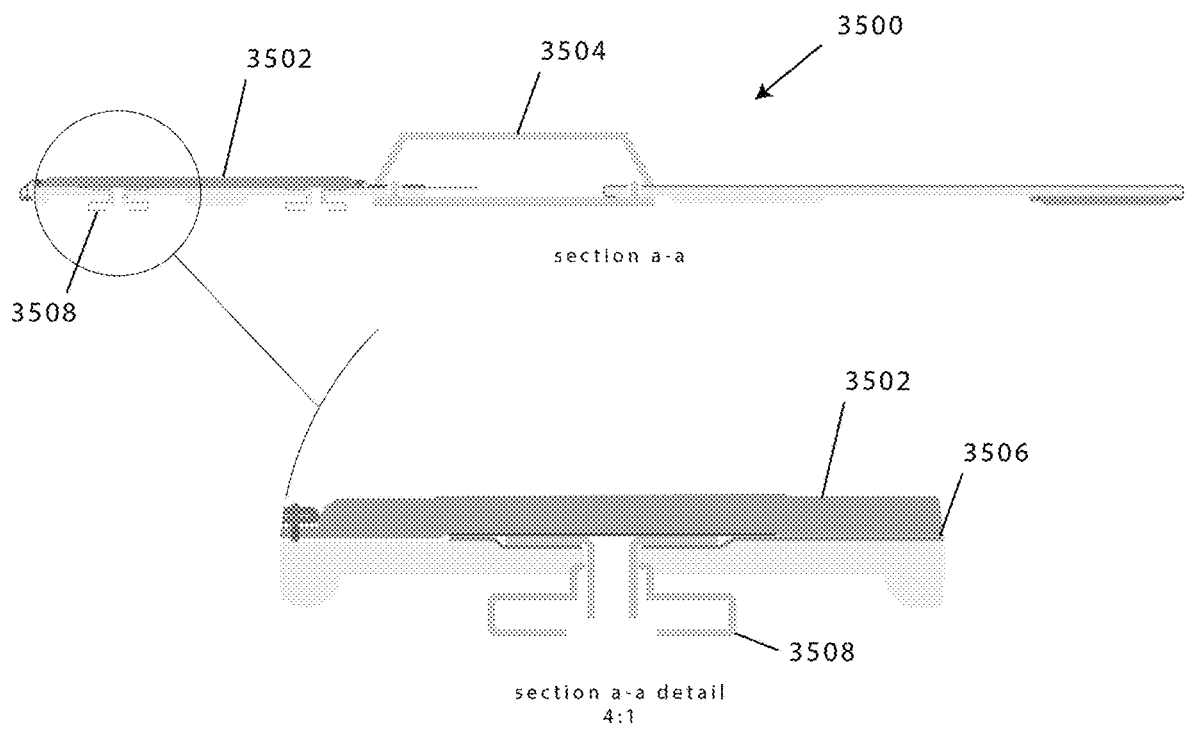
FIG. 35 illustrates a cross-sectional view of electrode snaps recessed into compressed neoprene to create a comfortable seal between the band and skin.

As shown in FIG. 35, one aspect of the device 3500 is a band 3502 to secure the stimulation device to the wrist. The band also connects two electrodes back to the device housing 3504 via a flexible circuit 3506. In other embodiments, the band may connect more than two electrodes back to the device housing.

In some embodiments, the electrodes (not shown) are removably recessed into pressed and perforated neoprene 3508 using a snap socket 3508 to create a comfortable seal between the band and skin, as drawn in FIG. 35. This seal also preserves the disposable hydrogels electrodes that connect to the patient's skin. The band can be vented by perforating the neoprene.

In some embodiments, the band lengths can be designed such that the first side fully houses and connects the electrodes that are positioned to target the median and radial nerves. The band length of the opposite side can be between about 10-13 cm to make it easier to fasten the device to the wrist for wrist sizes of 5 percentile female to 95 percentile male.

In some embodiments, the band is flexible to comfortably conform to the wearer's wrist, and allows the band to lie flat on a surface to make installation and removal of electrodes more convenient.

Riveting the electrical flex circuit to the band using an electrically conductive eyelet and snap is a process that secures the circuit in place and provides an electrical connection for the removable hydrogel electrodes.

In some embodiments, the band can be made of foam and neoprene and can accommodate three single electrodes. Recessed electrodes allow for a more comfortable fit and a more compact form factor.

Figure 36B:
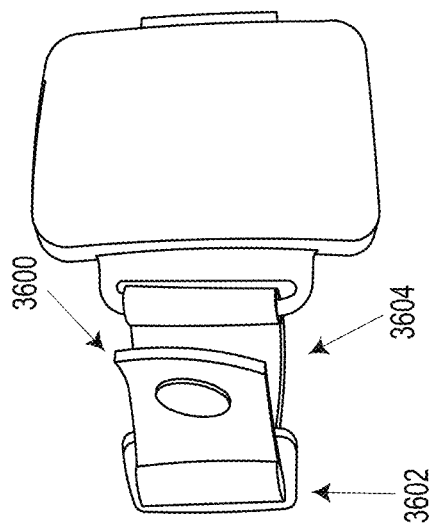
FIGS. 36A-36C illustrate various views of an adjustable buckle in combination with a snap or button fastener, which allows the wearer to adjust the tension of the armband after it has been fastened and secured to their arm/wrist.
Figure 36A:
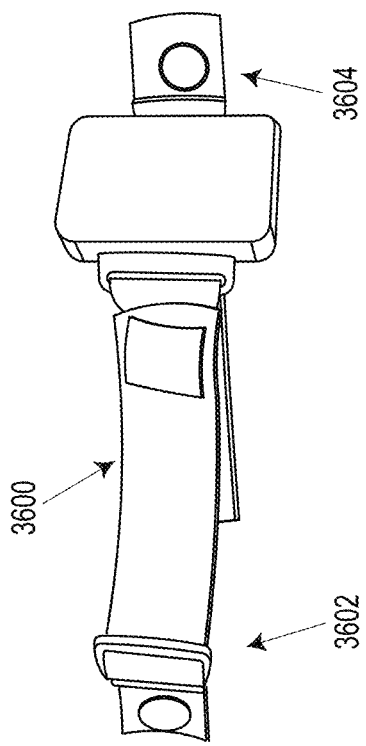
Figure 36C:
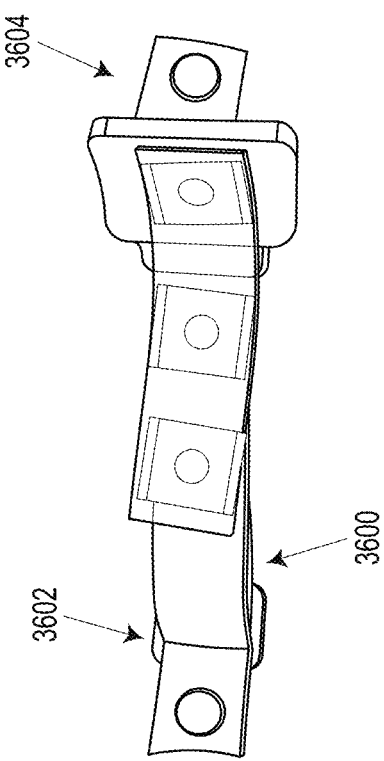

As shown in FIGS. 36A-36C, one embodiment for the band 3600 incorporates an adjustable ring or buckle 3602 in combination with a snap or button fastener 3604, which allows the wearer to adjust the tension of the band 3600 after it has been secured to their arm/wrist.

One aspect of the device are removable hydrogel coated electrodes that snap into the band and electronics housing. These electrodes a placed directly on the wearer's skin for a secure, robust electrical connection to prevent loosening or peeling during normal usage, which can cause pain or discomfort.

Figure 37A:
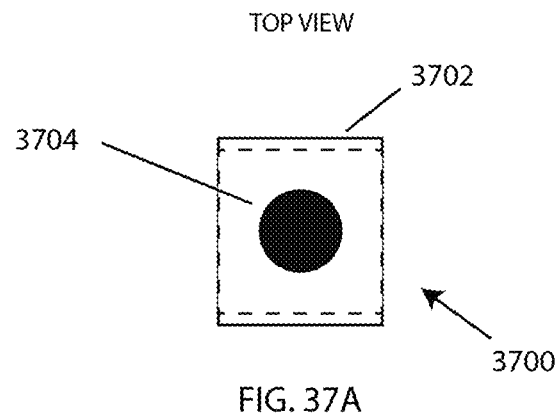
FIGS. 37A and 37B illustrate an embodiment of an electrode with a non-sticky pull tab.
Figure 37B:
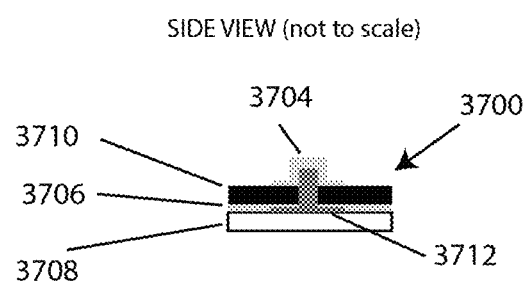

One embodiment of the electrodes 3700 has tabs 3702 that are not sticky to allow for easier installation and removal of the electrodes from the liner during installation and then from the band and housing during removal, as shown in FIGS. 37A and 37B. As an example, the non-sticky tabs may be approximately 1/16 inch on a 7/8 inch square electrode to minimize wasted space while enabling easy grasping. The electrodes 3700 can have a snap fitting 3704 than can be inserted into a snap socket in the band. The electrically conductive film 3706, which can function to spread current, and the stimulation gel 3708, such as an electrically conductive hydrogel, can coat the skin facing side of the electrode. A foam or cloth backing 3710 could be used to provide a non-sticky side for easy handling by the patient. In other embodiments, the double-sided stickness of the hydrogel is used to adhere directly to the band. In some embodiments, the connector 3712 may include a conductive eyelet and snap, wire, or other standard connector.

Figure 38:
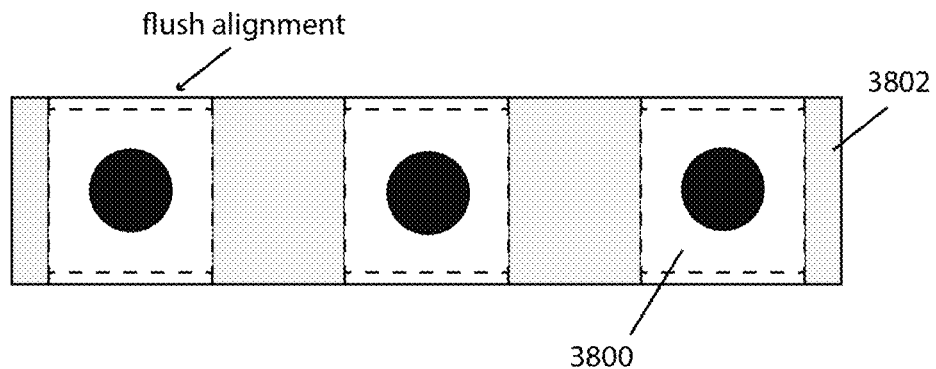
FIG. 38 illustrates electrodes that are appropriately spaced on a thin film liner for easier installation into the device.

One embodiment of the electrodes has three electrodes 3800 spaced on a thin, plastic liner 3802 with a spacing that corresponds to the electrical snaps on the band and housing, which allows for easier and quicker installation, as shown in FIG. 38.

Figure 39A:
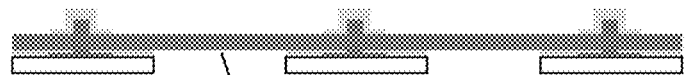
FIGS. 39A-39C illustrate electrodes connected by a single foam backing, including a concept for a serpentine connection.
Figure 39B:
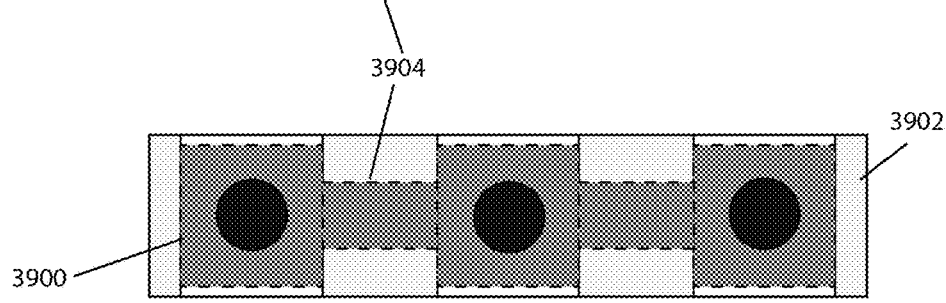
Figure 39C:
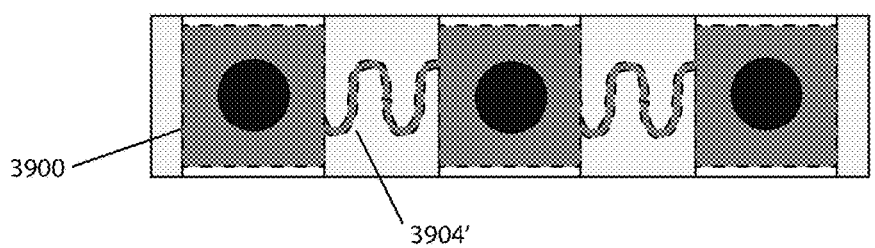

One embodiment of the electrodes has a backing made of a neoprene foam, which provides an a stiffer, non sticky surface to enable easier removal from the backing liner during installation. One embodiment of the electrodes has three electrodes 3900 spaced on a thin liner 3902 all connected with a single foam backing 3904 to make it easier to remove and discard the electrode after wearing, as shown in FIGS. 39A and 39B. In another embodiment, the foam backing 3904' connecting the electrodes 3900 is serpentine shaped to allow small movement between the electrodes, as shown in FIG. 40C.

Figure 40A:
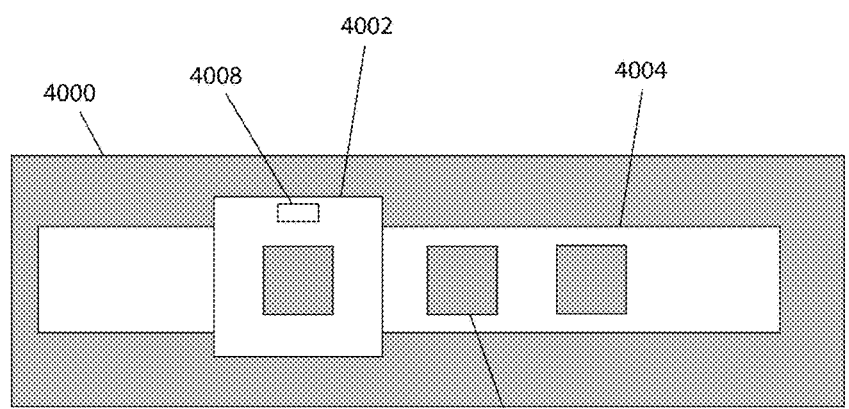
FIGS. 40A and 40B illustrate an embodiment of a cradle used to support the device when installing and removing the electrodes.
Figure 40B:
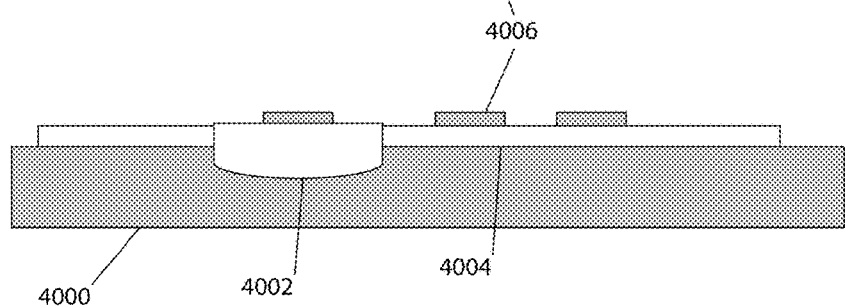

As shown in FIGS. 40A and 40B, one aspect of the device is a cradle 4000 or support mechanism in the packaging that holds the electronics housing 4002 and band 4004 so that it is easier to install and remove the electrodes 4006 and plug into the USB charger 4008. Since the housing of the device is curved, the cradle makes it easier for the device to be stable during these activities.

Figure 41:
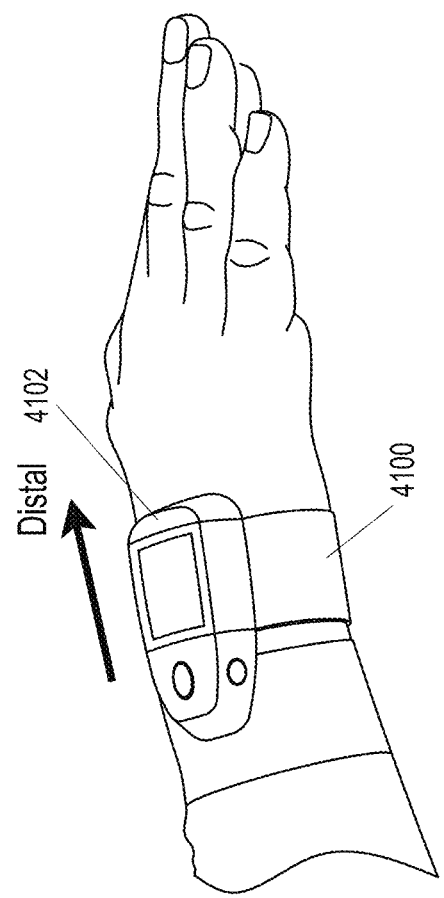
FIG. 41 illustrates an embodiment of the wearable stimulator where the electrodes are shifted distally with respect to the electronics housing to more easily target nerves distally on the wrist.

One aspect of the design is the location of the electrodes relative to the electronic housing to better target nerves at the wrist. The electrode and band 4100 in the housing box 4102 are shifted off-center distally (i.e., towards the hand) to allow for better targeting of the nerves. By moving the electrode placement distally on the arm the stimulation will more likely activate nerves instead of muscles, as shown in FIG. 41.

Figure 42B:
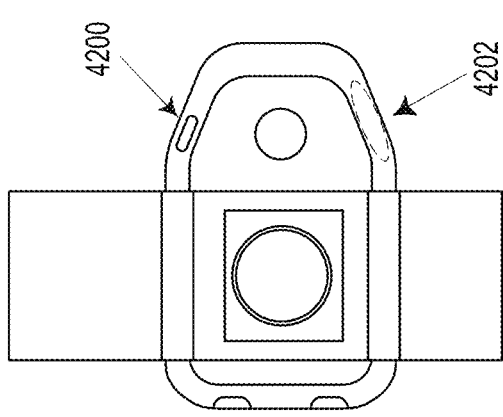
FIGS. 42A-42D illustrate various ways of locating buttons on the housing opposite a bracing surface.
Figure 42D:
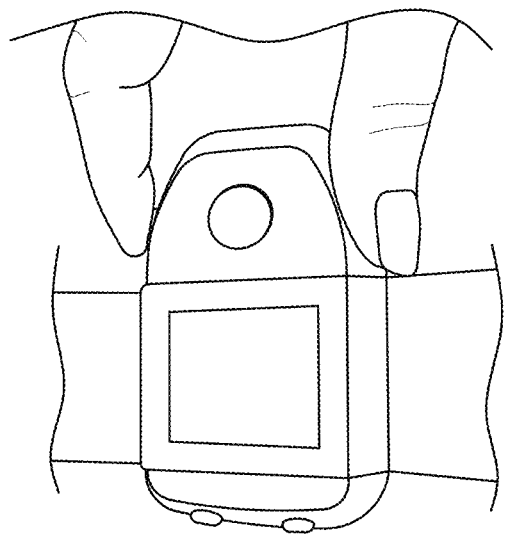
Figure 42A:
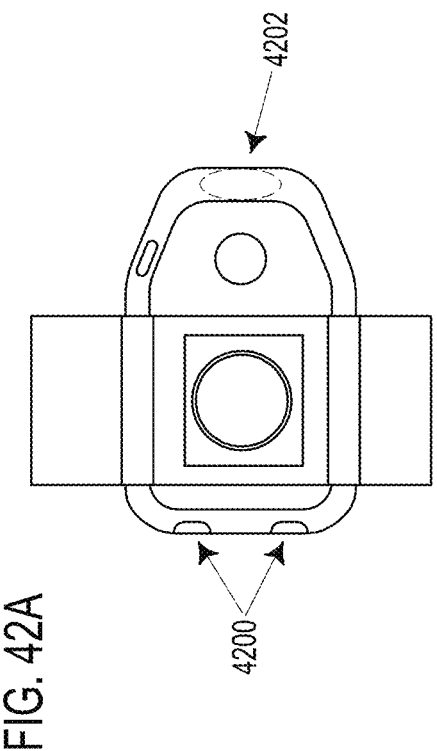
Figure 42C:
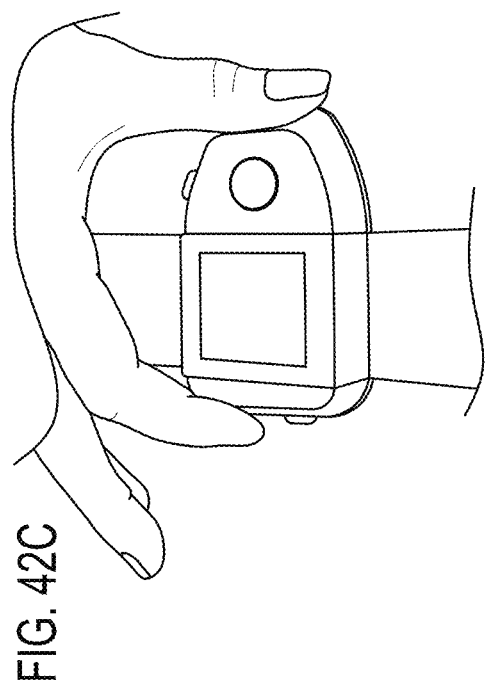

One aspect of the design has button locations that allow the wearer to more securely brace their hand when pressing a button 4200 by designing the housing with broad, flat surfaces 4202 on the opposite side of each button 4200, as shown in FIGS. 42A-42D. FIG. 42A shows a bracing location for targeting buttons at distal end of the device, FIG. 42B shows a bracing location for targeting button on side of the device, FIG. 42C shows a user bracing and targeting a distal button, and FIG. 42D shows a user bracing and targeting a side button. This aspect of the design is important to improve usability of the device for a wearer with tremor that have difficulty with targeting tasks.

One aspect of the design is a curved electronics housing that follows the shape of the arm and wrist, which allows for more consistent and easier positioning of the device when being applied by the wearer.

Alternative Form Factors

Figure 43:
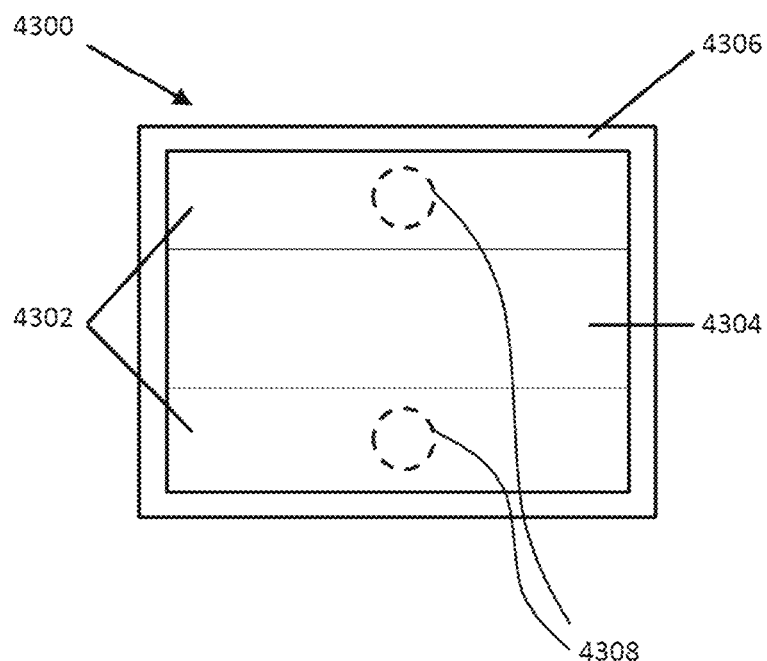
FIG. 43 illustrates one embodiment of an electrode with round snaps.

One concept for simplifying the process of placing the device is to combine the electrodes into one adhesive patch. In order to target any of the nerves, the electrodes have been lengthened to fit the width of most adults. FIG. 43 shows one embodiment of such an electrode 4300. On the skin side, two conductive regions that may have a carbon or silver backing to improve conductivity have a conductive hydrogel layer 4302 used to adhere and form a good contact with the skin. There is a nonconductive region 4304 in the center which may have no adhesive or some nonconductive adhesive. Note that around the hydrogel is an acrylic adhesive 4306, for example, used to maintain contact with the skin and provide shear strength. The adhesive also maintains a seal to prevent the hydrogels from drying out. The hacking of the electrode is preferrably a breathable material, like a nonwoven mesh. The backside of the electrode attaches with connectors 4308 to the device or hand to allow the electrical stimulation device to be interfaced to the hydrogels. This interface could be done in multiple ways, including using an adhesive with conductive lines to interface wth metal contacts on the band or device, or using snaps on the electrodes that can be snapped in to a conductive mating piece on the band or device.

If multiple nerves are targetted with the approach above, the band may require multiple interfaces to the electrode to accommodate varying nerve positions. Using snaps may require sliding components to accommodate individual differences in the nerve spacing, which may be addressed using conductive lines. An alternative approach would be to integrate multiple electrodes into one patch and offer patches with a wide variety of dimensions to accommodate different hand sizes and nerve positions.

Figure 44C:
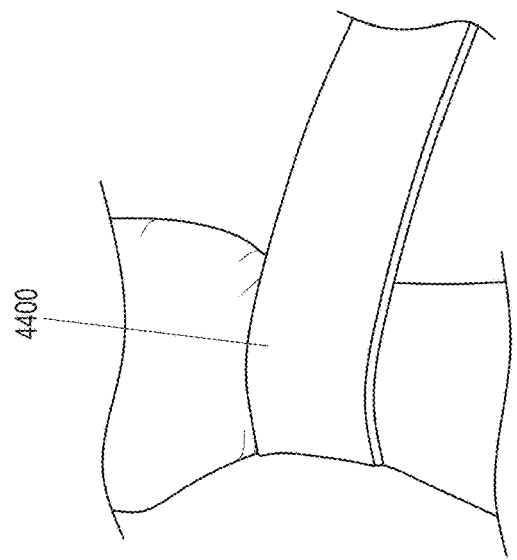
FIGS. 44A-44C illustrate an embodiment of a band that can be fastened to the user's wrist or arm using only a single hand.
Figure 44B:
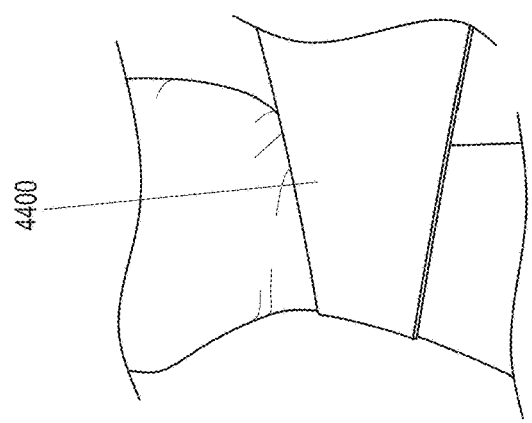
Figure 44A:
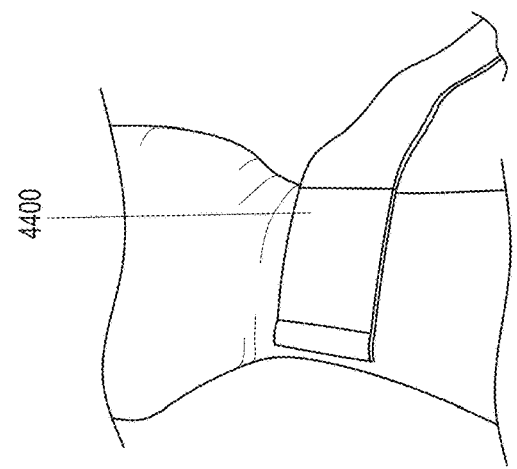

FIGS. 44A-44C demonstrate embodiments that simplify the band 4400 by using the stickiness of the hydrogels to facilitate placement. Instead of having a watch-like interface, where both straps are floppy and difficult to place, the adhesiveness of the electrode can be used to enable one-handed fastening. This approach may be particularly advantageous in subjects who have limited dexterity due to their hand tremors. Once the electrodes are placed on the wrist or arm, the adhesive electrode holds one end of the band to the wrist or arm and the patient can wrap the band around and fasten it. A further advantage to this deisgn is that the length of the band only needs to be altered at the end that does not interface with the electrode. As an example, FIG. 44A depicts placing the hand palm side up to visualize the electrodes placement and affix the end of the band. FIG. 44B depicts wrapping the band around the wrist while the band is held in place by the electrode adhesion. FIG. 44C depicts overlaying the closure mechanism, such as velcro or a magnetic clasp.

Figure 45A:
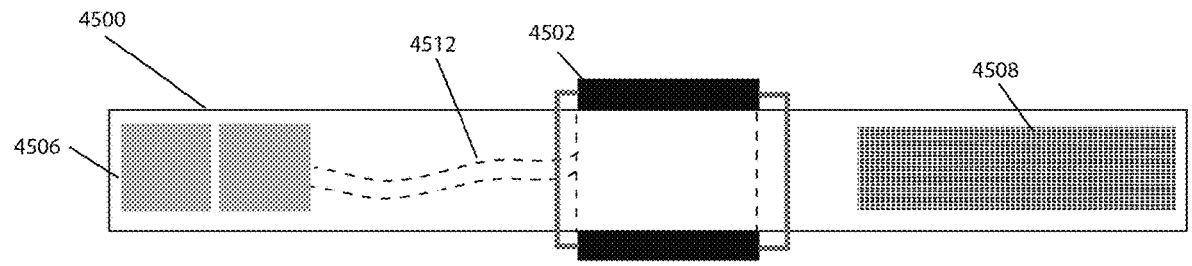
FIGS. 45A and 45B illustrate an embodiment of a band and its electronics.
Figure 45B:
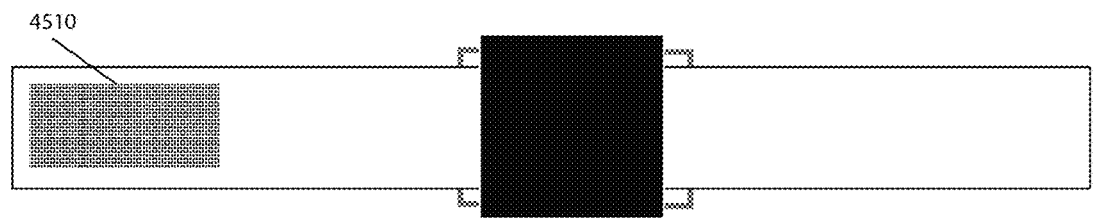

For optimal efficacy and comfort, the device should be aligned on the arm such that it targets the nerves for stimulation and positions the housing on the dorsal surface of the wrist. There are many ways to accomplish this through device design. One embodiment depicted in FIG. 45A (bottom view) and FIG. 45B (top view) is to use a band 4500 with a slidahie electronics housing 4502. The side of the band with the electrode(s) 4506 is placed and aligned with the ventral side of the wrists using anatomical landmarks with or without other visual indicators. The device can then be wrapped around the hand in one motion and secured with a fastener, in this case a velcro loop 4508 and a hook 3410. The position of the electronics housing 4502 is slideable and has a connection to the electrodes through the band that is accomplished by an accordian flex circuit or cables 4512 that can slide freely and tuck into the band.

Figure 46:
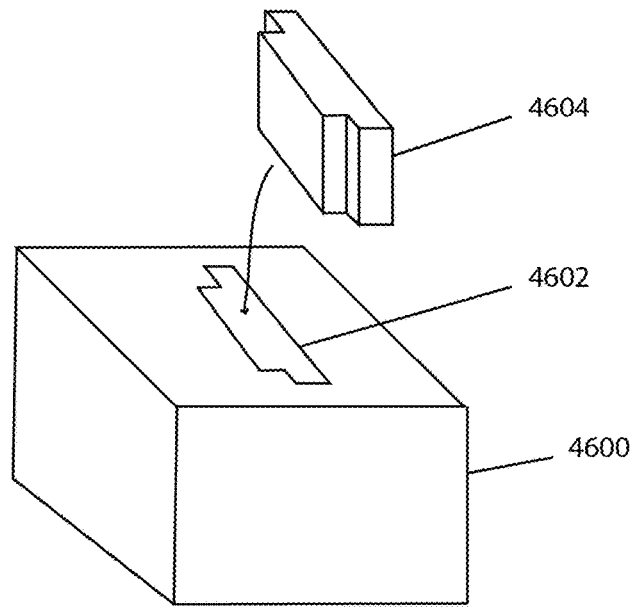
FIG. 46 illustrates an embodiment of a charging block with a keyed shape that can help in alignment and plugging of the device into a base station.

For patients with tremor, plugging in small cables like a USB can be difficult. Therefore, it would be desirable to provide easier interfaces to charge the device. One such way is to use an inductive coil in the device. When placed in the proximity of a charging pad, the device charges with no cables. This also enables and helps the device to be waterproof. However, it does have the disadvantage of being slower to charge and could add to the size of the device. A second possibility is to make a keyed hole 4602, so that patients can easily slide the device 4604 into the charger 4600, as shown in FIG. 46. In addition, the patients then have some structure to brace themselves against. The keyed hole can also be tapered such that the end that device is inserted into is much larger than the device and tapers down to fit the device at the plug. The tapering also helps placement of the device in the base station.

Figure 47A:
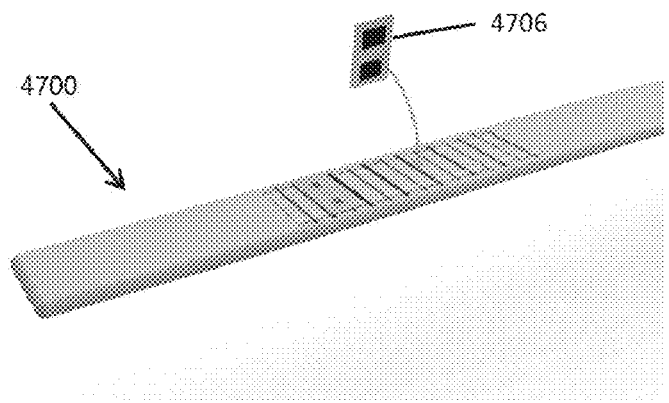
FIGS. 47A-47C illustrate another embodiment of a band and an inductive charger.
Figure 47B:
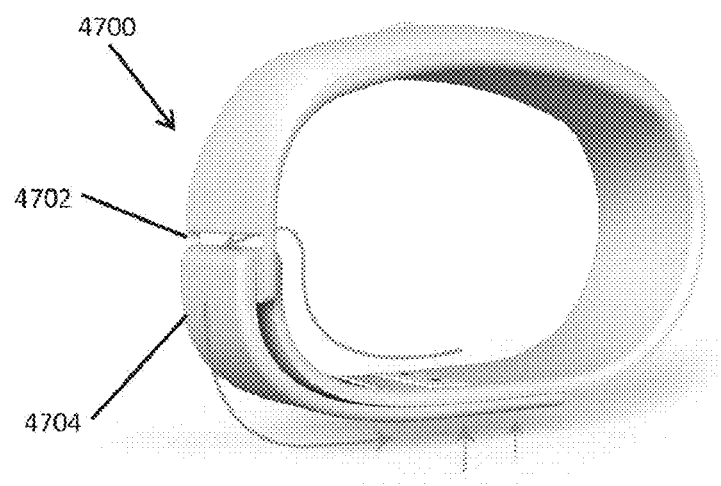
Figure 47C:
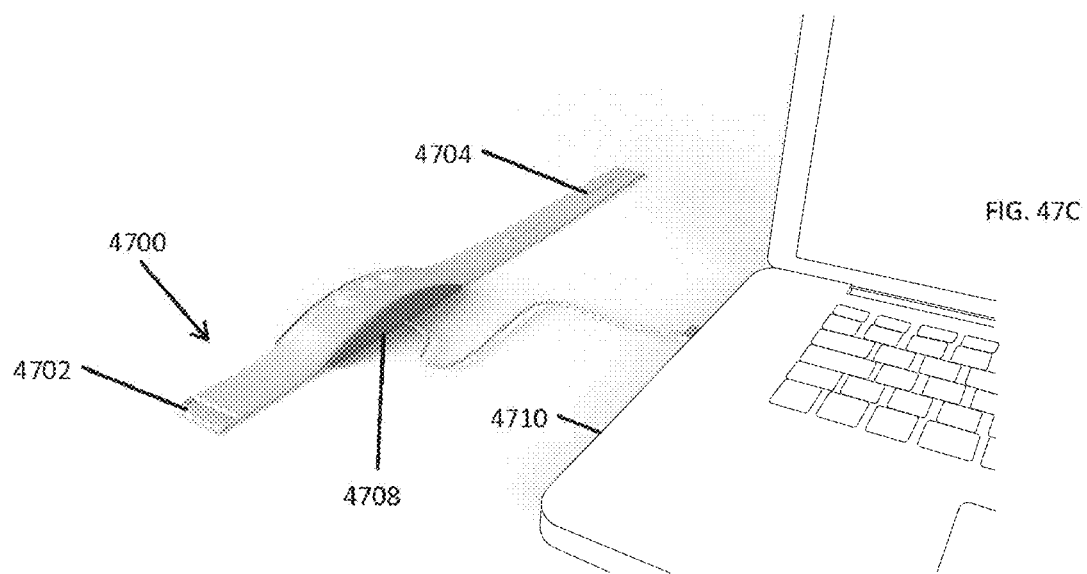

Another design possibility is a band 4700 with a D-ring 4702 and cinching strap 4704 as shown in FIGS. 47A-47C. Such a device can be laid flat for application of the electrodes 4706 and inductive charging. The cinching strap allows tightening and positing of the band with one hand. FIG. 47A shows the band 4700 opened to place the disposable electrode pairs 4706—multiple spaces are provided to customize the spacing for different sizes of wrists. FIG. 47B shows the closure mechanism, and FIG. 47C shows an inductive charger 4708 hooked up to laptop 4710.

Figure 48A:
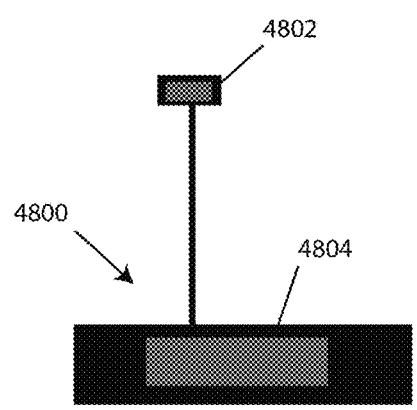
FIGS. 48A-48C illustrate an embodiment of a one-fingered glove with fasteners and electrodes.
Figure 48B:
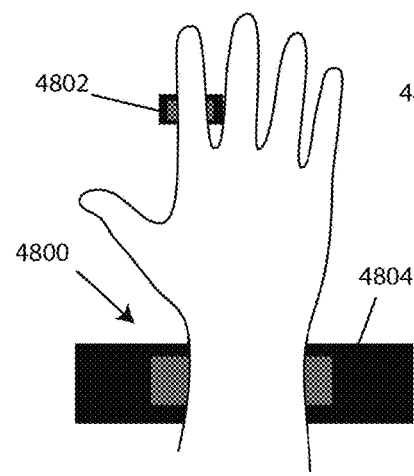
Figure 48C:
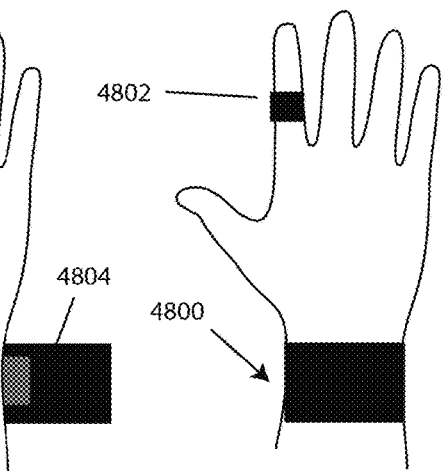

Another embodiment shown in FIGS. 48A-48C includes a one or multi-fingered glove 4800 where one electrode 4802 is a ring around the finger and a second electrode 4804 is located at the wrist with the electronics. A major advantage of this design is that it does not require any precise positioning due to the nerve location and accessibility in the fingers. The one fingered glove can be made out of flexible materials, such as a glove.

The terms "about" and "approximately" can mean within 5%, 10%, 15%, or 20%, or can mean within 5 degrees or 10 degrees.

It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

What is claimed is:

1. A transcutaneous method of stimulating at least one nerve in an arm or wrist of a patient, the method comprising:
   placing a circumferential band comprising a first electrode and a second electrode around the patient's arm or wrist in a configuration such that in a transverse cross-sectional plane of the arm or wrist there is a 90 degree to 180 degree angle between a line extending between a first nerve and the first electrode and a line extending between the first nerve and the second electrode, wherein the first and second electrodes are spaced a predetermined distance apart, wherein the first electrode and the second electrode comprise a carbon material, and
   delivering a first electrical stimulus between the first and second electrodes to preferentially stimulate the first nerve, the first electrical stimulus generated from a pulse generator, wherein the first electrical stimulus comprises a burst stimulus.

2. The method of claim 1, further comprising:
   delivering a second electrical stimulus from the first electrode and a third electrode to excite a second nerve, the second electrical stimulus generated from the pulse generator;
   measuring one or more physiologic characteristics of the patient using a sensor;
   temporally offsetting the first electrical stimulus from the second electrical stimulus by a period of time; and
   adjusting the first electrical stimulus based upon the measured one or more physiologic characteristics,
   wherein the first electrical stimulus and the second electrical stimulus comprise burst stimuli,
   wherein the band comprises a third electrode spaced a predetermined distance apart from the first and second electrodes such that there is a 90 degree to 180 degree angle between a line extending between a second nerve and the first electrode and a line extending between the second nerve and the third electrode.

3. The method of claim 1, wherein the band comprises a third electrode spaced a predetermined distance apart from the first and second electrodes such that there is a 90 degree to 180 degree angle between a line extending between a second nerve and the first electrode and a line extending between the second nerve and the third electrode.

4. The method of claim 3, further comprising delivering a second electrical stimulus from the first electrode and the third electrode to stimulate the second nerve, the second electrical stimulus generated from the pulse generator.

5. The method of claim 4, further comprising temporally offsetting the first electrical stimulus from the second electrical stimulus by a preset period of time.

6. The method of claim 4, wherein the first electrical stimulus and the second electrical stimulus comprise patterned stimuli.

7. The method of claim 6, wherein the first electrical stimulus and the second electrical stimulus comprise burst stimuli.

8. The method of claim 7, wherein the burst stimuli are non-overlapping.

9. The method of claim 4, wherein the first electrical stimulus and the second electrical stimulus comprise waveforms with ramped amplitudes.

10. The method of claim 1, further comprising measuring one or more physiologic characteristics of the patient via a sensor operably connected to the band.

11. The method of claim 10, further comprising adjusting the first electrical stimulus based upon the one or more measured physiologic characteristics.

12. The method of claim 1, wherein the first electrical stimulus has a duration between 20 and 60 minutes.

13. A transcutaneous method of stimulating at least one nerve in an upper extremity of a patient, the method comprising:
    placing a band comprising a first electrode and a second electrode circumferentially around the patient's upper extremity in a configuration such that in a transverse cross-sectional plane of the arm or wrist there is a 90 degree to 180 degree angle between a line extending between a first nerve in the patient's upper extremity and the first electrode and a line extending between the first nerve and the second electrode, wherein the first and second electrodes are spaced a predetermined distance apart; and
    delivering a first electrical stimulus from the first and second electrodes to excite the first nerve, the first electrical stimulus generated from the pulse generator.

14. The method of claim 13,
wherein the first electrical stimulus and a second electrical stimulus comprise patterned stimuli,
wherein the band comprises a third electrode spaced a predetermined distance apart from the first and second electrodes such that there is a 90 degree to 180 degree angle between a line extending between a second nerve and the first electrode and a line extending between the second nerve and a third electrode, wherein the method further comprises:
delivering a second electrical stimulus from the first electrode and the third electrode to excite the second nerve, the second electrical stimulus generated from the pulse generator;
measuring one or more physiologic characteristics of the patient using a sensor;
temporally offsetting the first electrical stimulus from the second electrical stimulus by a period of time; and
adjusting the first electrical stimulus based upon the one or more measured physiologic characteristics.

15. The method of claim 13, wherein the band comprises a third electrode spaced a predetermined distance apart from the first and second electrodes such that there is a 90 degree to 180 degree angle between a line extending between a second nerve and the first electrode and a line extending between the second nerve and the third electrode, the second nerve selected from the patient's median, radial and ulnar nerves.

16. The method of claim 15, wherein the first electrical stimulus and the second electrical stimulus comprise burst stimuli.

17. The method of claim 15, wherein the first electrical stimulus and the second electrical stimulus comprise waveforms with ramped amplitudes.

18. A transcutaneous method of stimulating at least one nerve in the upper extremity of a patient, the method comprising:
providing a band and housing having a predetermined circumferential spacing for a first electrode, a second electrode, and a third electrode, wherein the predetermined circumferential spacing is based on the determined circumference of the patient's wrist, wherein the housing encloses a pulse generator configured to be in electrical communication with the first electrode, the second electrode, and the third electrode, wherein the band and housing are configured to be positioned on the upper extremity such that the first electrode is positioned along the midline of the dorsal side of the upper extremity, the second electrode is positioned approximately along the midline of the ventral side of the upper extremity, and the third electrode is positioned in between the first electrode and second electrode, wherein the first electrode and the second electrode form a first electrode pair and the first electrode and third electrode form a second electrode pair;
stimulating a first nerve by delivering a first electrical stimulus between the first electrode pair; and
stimulating a second nerve by delivering a second electrical stimulus between the second electrode pair.

19. The method of claim 18, further comprising:
temporally offsetting the first electrical stimulus from the second electrical stimulus by a period of time; and
adjusting the first electrical stimulus based upon a measured physiologic characteristic,
wherein the first electrical stimulus and the second electrical stimulus comprise patterned stimuli,
wherein stimulating the first nerve further comprises signaling the pulse generator via a controller to deliver the electrical stimuli to preferentially stimulate the first nerve via the first electrode pair to the patient, and
wherein stimulating the second nerve further comprises signaling the pulse generator via the controller to deliver the electrical stimuli to preferentially stimulate the second nerve via the second electrode pair to the patient,
wherein the band further comprises an adjustable ring or buckle.

* * * * *